US011116740B2

(12) United States Patent
Venn-Watson

(10) Patent No.: US 11,116,740 B2
(45) Date of Patent: *Sep. 14, 2021

(54) METHODS FOR USE IN SUPPORT OF PLANNED SUPPLEMENT AND FOOD INGREDIENT PRODUCTS FOR DIAGNOSIS AND TREATMENT OF METABOLIC SYNDROME

(71) Applicant: The United States of America as represented by the Secretary of the Navy, San Diego, CA (US)

(72) Inventor: Stephanie Venn-Watson, San Diego, CA (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/534,382

(22) Filed: Aug. 7, 2019

(65) Prior Publication Data

US 2019/0358183 A1 Nov. 28, 2019

Related U.S. Application Data

(63) Continuation of application No. 16/018,922, filed on Jun. 26, 2018, now Pat. No. 10,449,171, which is a continuation of application No. 15/582,433, filed on Apr. 28, 2017, now Pat. No. 10,022,347, which is a continuation of application No. 15/030,031, filed as application No. PCT/US2015/067172 on Apr. 15, 2016, now Pat. No. 9,662,306, which is a continuation-in-part of application No. 14/591,660, filed on Jan. 7, 2015, now Pat. No. 9,561,206.

(51) Int. Cl.

| | | |
|---|---|---|
| *A61P 15/08* | (2006.01) |
| *A61P 15/00* | (2006.01) |
| *A61P 3/06* | (2006.01) |
| *A61P 3/04* | (2006.01) |
| *A61P 3/00* | (2006.01) |
| *A61P 3/10* | (2006.01) |
| *A61P 7/00* | (2006.01) |
| *A61P 7/02* | (2006.01) |
| *A61P 25/00* | (2006.01) |
| *A61P 25/20* | (2006.01) |
| *A61P 29/00* | (2006.01) |
| *A61P 1/16* | (2006.01) |
| *A61P 9/12* | (2006.01) |
| *A61P 9/00* | (2006.01) |
| *A61P 35/00* | (2006.01) |
| *A61P 11/06* | (2006.01) |
| *A61K 31/20* | (2006.01) |
| *A61K 31/202* | (2006.01) |
| *A61K 31/201* | (2006.01) |
| *G01N 33/92* | (2006.01) |

(52) U.S. Cl.
CPC ............ *A61K 31/20* (2013.01); *A61K 31/201* (2013.01); *A61K 31/202* (2013.01); *G01N 33/92* (2013.01); *G01N 2405/00* (2013.01); *G01N 2800/04* (2013.01); *G01N 2800/042* (2013.01); *G01N 2800/22* (2013.01); *G01N 2800/50* (2013.01)

(58) Field of Classification Search
CPC .. A61P 15/08; A61P 15/00; A61P 3/06; A61P 3/04; A61P 3/00; A61P 3/10; A61P 7/00; A61P 7/02; A61P 25/00; A61P 25/20; A61P 29/00; A61P 11/06; A61P 1/16; A61P 9/12; A61P 9/00; A61P 35/00; A61K 31/20; A61K 31/202; A61K 31/201; G01N 33/92

See application file for complete search history.

(56) References Cited

U.S. PATENT DOCUMENTS

| 9,561,206 B2 * | 2/2017 | Venn-Watson | ............ A61P 3/10 |
| 9,662,306 B2 * | 5/2017 | Venn-Watson | ......... G01N 33/92 |
| 10,022,347 B2 * | 7/2018 | Venn-Watson | ......... A61K 31/20 |
| 10,449,171 B2 * | 10/2019 | Venn-Watson | ......... A61K 31/20 |
| 2011/0201558 A1 * | 8/2011 | Roe | ........................ A61P 25/16 |
| | | | 514/17.8 |

\* cited by examiner

*Primary Examiner* — Sun Jae Yoo
(74) *Attorney, Agent, or Firm* — Naval Information Warfare Center, Pacific; Kyle Eppele; Susanna J. Torke

(57) ABSTRACT

Compositions including an odd chain fatty acid, and salts and derivatives thereof, and methods for metabolic syndrome treatment and prophylaxis are provided, including compositions and methods for treating diabetes, obesity, hyperferritinemia, elevated insulin, glucose intolerance, dyslipidemia and related conditions. Methods for the diagnosis and monitoring of metabolic syndrome are also provided.

6 Claims, 16 Drawing Sheets

METHODS FOR USE IN SUPPORT OF PLANNED SUPPLEMENT AND FOOD INGREDIENT PRODUCTS FOR DIAGNOSIS AND TREATMENT OF METABOLIC SYNDROME

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation application of U.S. application Ser. No. 16/018,922, which is a further continuation of U.S. application Ser. No. 15/582,433, which is further a continuation application of U.S. application Ser. No. 15/030,031, which is the national phase under 35 U.S.C. § 371 of prior PCT International Application No. PCT/US2015/067172, which has an International Filing Date of Dec. 21, 2015, which designates the United States of America, and which further claims priority to U.S. application Ser. No. 14/591,660, filed Jan. 7, 2015. Each of the aforementioned applications are incorporated by reference herein in their entirety, and are hereby expressly made a part of this specification.

STATEMENT REGARDING FEDERALLY SPONSORED R&D

The United States Government has ownership rights in this invention, pursuant to passing of title to a Subject Invention under Federal Grant N00014-12-1-0294 (National Marine Mammal Foundation).

FIELD OF THE INVENTION

Compositions including an odd chain fatty acid, and salts and derivatives thereof, and methods for metabolic syndrome treatment and prophylaxis are provided, including compositions and methods for treating diabetes, obesity, hyperferritinemia, elevated insulin, glucose intolerance, dyslipidemia and related conditions. Methods for the diagnosis and monitoring of metabolic syndrome are also provided.

BACKGROUND OF THE INVENTION

Metabolic syndrome is an underlying disorder of energy utilization and storage. Metabolic syndrome affects a substantial proportion of the population of developed countries, including the United States. It is associated with the risk of developing cardiovascular disease, diabetes (especially type 2 diabetes), and other conditions such as polycystic ovary syndrome, fatty liver disease, cholesterol gallstones, asthma, sleep disturbances, and some forms of cancer. Metabolic syndrome is characterized by abdominal (central) obesity, elevated blood pressure, elevated insulin, elevated fasting plasma glucose, elevated serum triglycerides, decreased high-density lipoprotein (HDL) levels, proinflammatory state (recognized clinically by elevations of C-reactive protein (CRP)), and a prothrombotic state.

High serum ferritin that is not associated with known genetic mutations has been observed. Ferritin is a measure of total iron body stores. High ferritin in the blood (i.e., hyperferritinemia) and associated iron overload have been associated with metabolic syndrome and related disorders in humans. Metabolic syndrome is also correlated with hyperferritinemia (with or without iron overload), which is itself associated with impaired adiponectin production. Until now, serum ferritin has not been routinely tested in human subjects. The mechanism by which high ferritin levels increase the risk of diabetes is not fully understood, but proposed mechanisms include direct injury to the liver and pancreas from excessive deposition or indirect injury from increased oxidative radicals.

Metabolic syndrome is alternatively known as Syndrome X, prediabetes, cardiometabolic syndrome, insulin resistance syndrome, Reaven's syndrome, and CHAOS. A number of risk factors for metabolic syndrome have been identified, which include but are not limited to obesity, advancing age, high stress, and poor diet. Metabolic syndrome can also arise due to genetic disorders or other in-born errors of metabolism.

Treatment of metabolic syndrome generally targets the indices named above. Often treatment focuses on conditions associated with more advanced stages of metabolic syndrome, such as cardiovascular disease and diabetes. For diabetes, administration of metformin, insulin, or an insulin analog is sometimes indicated, as is administration of other medicaments such as statins, fibrates, and niacin. However, these medicaments may lead to undesirable side effects. Early stage treatment and prevention of metabolic syndrome is generally limited to recommendation of a low saturated fat diet with increased daily exercise. Some subjects are unable to effectively comply with, or unresponsive to, these regimens.

SUMMARY OF THE INVENTION

Compositions and methods for treatment and prevention of metabolic syndrome, and treating associated conditions are provided. These compositions comprise one or more odd chain fatty acids, derivatives of odd chain fatty acids, and salts thereof, which may be administered in combination with other medicaments or as part of various treatment regimens. The provided compositions are effective for modulating markers associated with metabolic syndrome, serum hyperferritinemia, elevated insulin, glucose intolerance, dyslipidemia and fatty liver. Methods are provided for administering the compositions.

Accordingly, in a generally applicable first aspect (i.e., independently combinable with any of the aspects or embodiments identified herein), a pharmaceutical composition is provided, comprising: one or more odd chain fatty acids or pharmaceutically acceptable salts thereof; and a pharmaceutically acceptable carrier.

In an embodiment of the first aspect (i.e., independently combinable with any of the aspects or embodiments identified herein), the one or more odd chain fatty acids is heptadecanoic acid.

In an embodiment of the first aspect (i.e., independently combinable with any of the aspects or embodiments identified herein), the composition is substantially free from even chain fatty acids.

In an embodiment of the first aspect (i.e., independently combinable with any of the aspects or embodiments identified herein), the composition comprises a plurality of odd chain fatty acids.

In an embodiment of the first aspect (i.e., independently combinable with any of the aspects or embodiments identified herein), the composition is in a unit dosage form.

In an embodiment of the first aspect (i.e., independently combinable with any of the aspects or embodiments identified herein), the pharmaceutical composition is configured for administration of from 2.5 mg to 11 mg, per 1 kg of body weight, of the one or more odd chain fatty acids or pharmaceutically acceptable salts thereof to a patient.

In an embodiment of the first aspect (i.e., independently combinable with any of the aspects or embodiments identified herein), the pharmaceutical composition is configured for administration once per day.

In an embodiment of the first aspect (i.e., independently combinable with any of the aspects or embodiments identified herein), the pharmaceutical composition comprises from 0.01 mg to 10000 mg of the one or more odd chain fatty acids or pharmaceutically acceptable salts thereof.

In a generally applicable second aspect (i.e., independently combinable with any of the aspects or embodiments identified herein), use is provided of a pharmaceutical composition of the first aspect or any of its embodiments, in the manufacture of a medicament for treatment or prophylaxis of metabolic syndrome, cardiovascular disease, diabetes, type 2 diabetes, polycystic ovary syndrome, fatty liver, cholesterol gallstones, asthma, sleep disturbance, cancer, abdominal obesity, elevated blood pressure, elevated fasting plasma glucose, elevated serum triglycerides, decreased high-density lipoprotein levels, proinflammatory state, elevation of C-reactive protein, a prothrombotic state, hyperferritinemia, hyperferritinemia with iron overload, and hyperferritinemia without iron overload.

In an embodiment of the second aspect (i.e., independently combinable with any of the aspects or embodiments identified herein), the use is in the manufacture of a medicament for treatment or prophylaxis of hyperferritinemia.

In an embodiment of the second aspect (i.e., independently combinable with any of the aspects or embodiments identified herein), the use is in the manufacture of a medicament for treatment or prophylaxis of metabolic syndrome.

In an embodiment of the second aspect (i.e., independently combinable with any of the aspects or embodiments identified herein), the pharmaceutical composition is configured to modulate a marker of metabolic syndrome or a symptom of metabolic syndrome. The, marker of metabolic syndrome can optionally be selected from the group consisting of odd chain fatty acid percentage, serum concentration of an odd chain fatty acid, red blood cell membrane concentration of an odd chain fatty acid, serum total odd chain fatty acids, red blood cell membrane total odd chain fatty acids, serum ferritin, serum iron, transferritin saturation, serum glucose, serum triglycerides, blood pressure, adiponectin, HDL cholesterol, urine microalbumin, CRP, IL-6, TNFα, c-Jun N-terminal kinase, ATM and monocyte-chemoattractant protein-1.

In an embodiment of the second aspect (i.e., independently combinable with any of the aspects or embodiments identified herein), the pharmaceutical composition is configured to increase a serum concentration or a red blood cell membrane concentration of the one or more odd chain fatty acids by at least about $0.01 \times 10^{-4}$ M above a pretreatment value.

In a generally applicable third aspect (i.e., independently combinable with any of the aspects or embodiments identified herein), a method is provided for the treatment or prophylaxis of metabolic syndrome, cardiovascular disease, diabetes, type 2 diabetes, polycystic ovary syndrome, fatty liver, cholesterol gallstones, asthma, sleep disturbance, cancer, abdominal obesity, elevated blood pressure, elevated fasting plasma glucose, elevated serum triglycerides, decreased high-density lipoprotein levels, proinflammatory state, elevation of C-reactive protein, a prothrombotic state, hyperferritinemia, hyperferritinemia with iron overload, and hyperferritinemia without iron overload, comprising: administering to a patient in need thereof, an effective amount of one or more odd chain fatty acids or pharmaceutically acceptable salts thereof.

In an embodiment of the third aspect (i.e., independently combinable with any of the aspects or embodiments identified herein), the one or more odd chain fatty acids or pharmaceutically acceptable salts thereof is provided as a pharmaceutical composition in a unit dosage form comprising the one or more odd chain fatty acids or pharmaceutically acceptable salts thereof and a pharmaceutically acceptable carrier.

In an embodiment of the third aspect (i.e., independently combinable with any of the aspects or embodiments identified herein), the unit dosage form comprises from 0.01 mg to 10000 mg of the one or more odd chain fatty acids or pharmaceutically acceptable salts thereof.

In an embodiment of the third aspect (i.e., independently combinable with any of the aspects or embodiments identified herein), the one or more odd chain fatty acids is heptadecanoic acid.

In an embodiment of the third aspect (i.e., independently combinable with any of the aspects or embodiments identified herein), the pharmaceutical composition is substantially free from even chain fatty acids.

In an embodiment of the third aspect (i.e., independently combinable with any of the aspects or embodiments identified herein), the pharmaceutical composition comprises a plurality of odd chain fatty acids.

In an embodiment of the third aspect (i.e., independently combinable with any of the aspects or embodiments identified herein), from 2.5 mg to 11 mg of the one or more odd chain fatty acids or pharmaceutically acceptable salts thereof is administered to the patient, per 1 kg of body weight, per day.

In an embodiment of the third aspect (i.e., independently combinable with any of the aspects or embodiments identified herein), the one or more odd chain fatty acids or pharmaceutically acceptable salts thereof is administered to the patient once per day.

In an embodiment of the third aspect (i.e., independently combinable with any of the aspects or embodiments identified herein), a serum concentration or a red blood cell membrane concentration of the one or more odd chain fatty acids is increased by at least about $0.01 \times 10^{-4}$ M above a pretreatment value.

Any of the features of an embodiment of the first through third aspects is applicable to all aspects and embodiments identified herein. Moreover, any of the features of an embodiment of the first through third aspects is independently combinable, partly or wholly with other embodiments described herein in any way, e.g., one, two, or three or more embodiments may be combinable in whole or in part. Further, any of the features of an embodiment of the first through third aspects may be made optional to other aspects or embodiments. Any aspect or embodiment of a method can be performed by a system or apparatus of another aspect or embodiment, and any aspect or embodiment of a system can be configured to perform a method of another aspect or embodiment.

DETAILED DESCRIPTION

Figure 1:
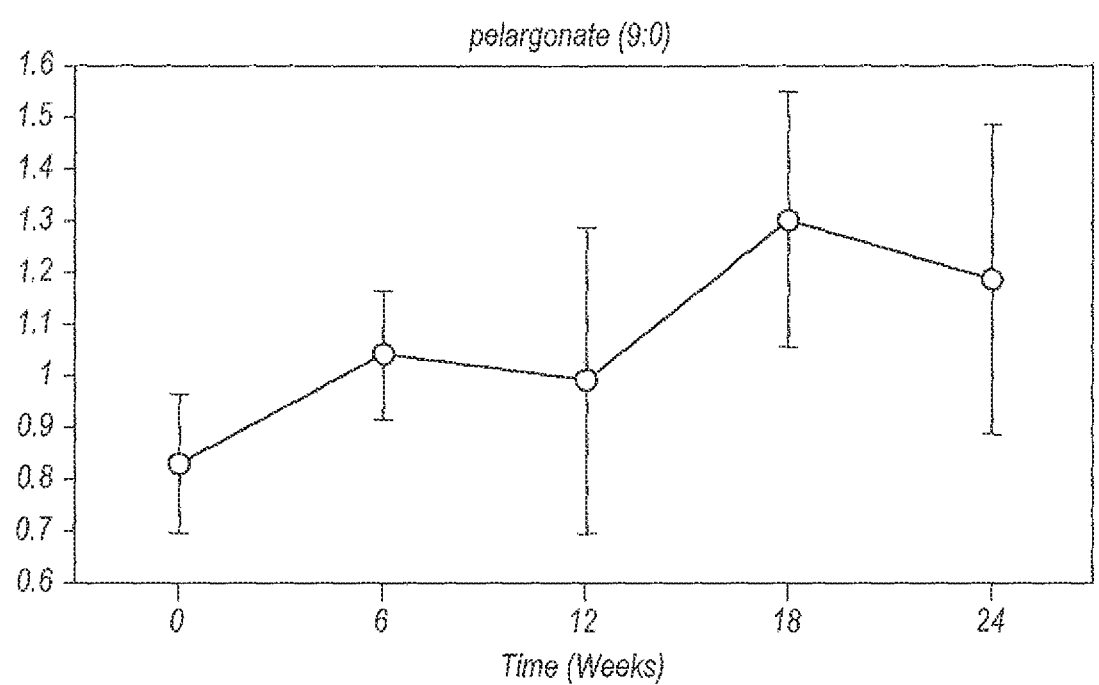
FIG. 1 provides data for pelargonate for Group A dolphins in an embodiment according to Example 1.
Figure 2A:
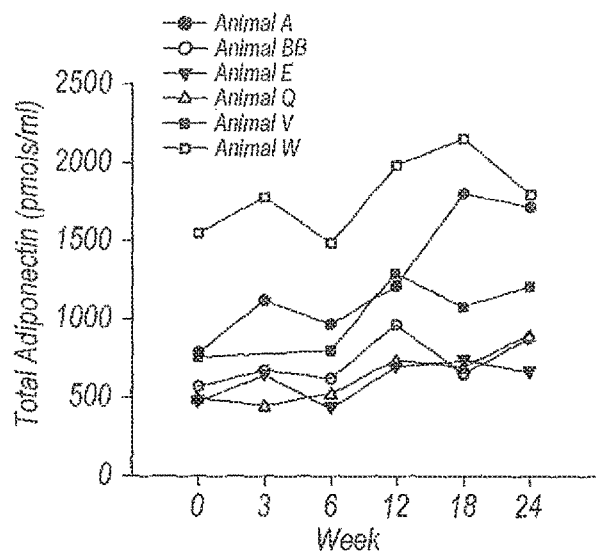
FIG. 2A provides data for total serum adiponectin and percent unmodified adiponectin in an embodiment according to Example 1, where symbols and lines correspond to the measured values of total adiponectin (pmol/ml)
Figure 2B:
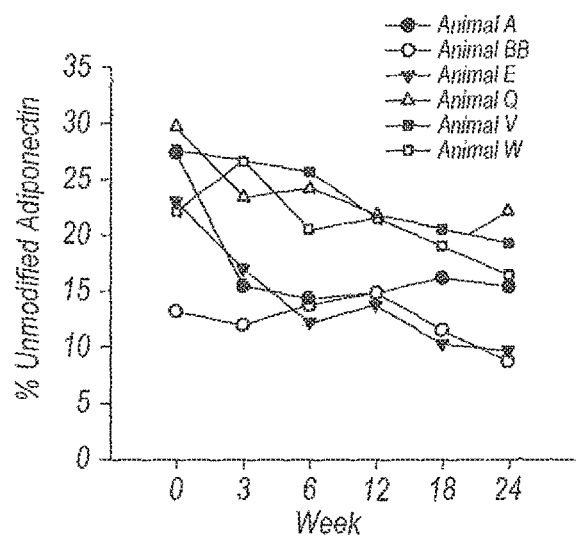
FIG. 2B provides data for total serum adiponectin and percent unmodified adiponectin in an embodiment according to Example 1. Symbols and lines correspond to the measured values of percent unmodified adiponectin in each dolphin from time 0 to week 24.
Figure 2C:
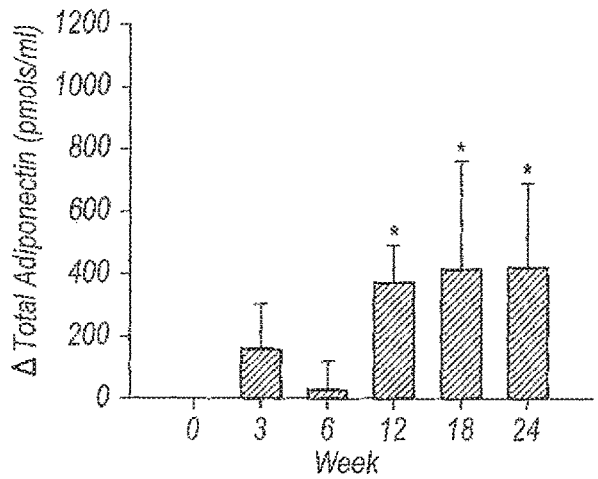
FIG. 2C provides data for total serum adiponectin and percent unmodified adiponectin in an embodiment according to Example 1. Symbols and lines correspond to the measured values of mean change in total adiponectin; and, FIG. 2D provides data for total serum adiponectin and percent unmodified adiponectin in an embodiment according to Example 1. Symbols and lines correspond to the measured values of mean percent change in percent unmodified adiponectin for the 6 dolphins at each time point over the 24 week study (n=6; except for week 3, n=5) (*denotes $P<0.05$).
Figure 2D:
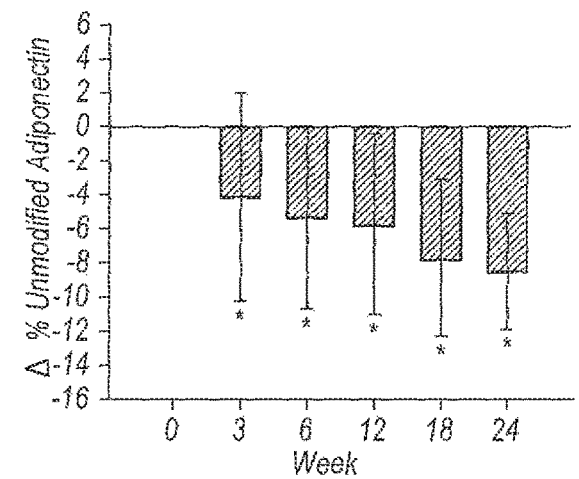
Figure 3A:
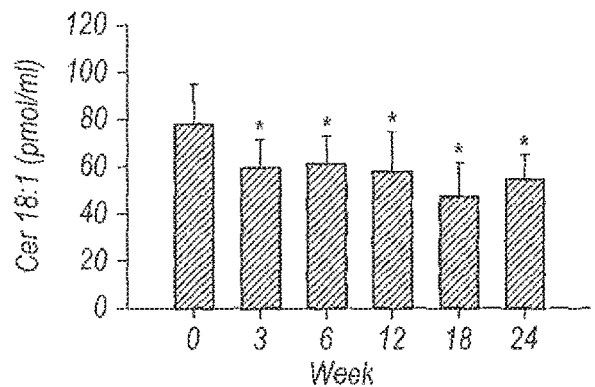
FIG. 3A provides data for serum ceramide 18:1 levels in an embodiment according to Example 1 (*=denotes $P<0.05$)
Figure 3B:
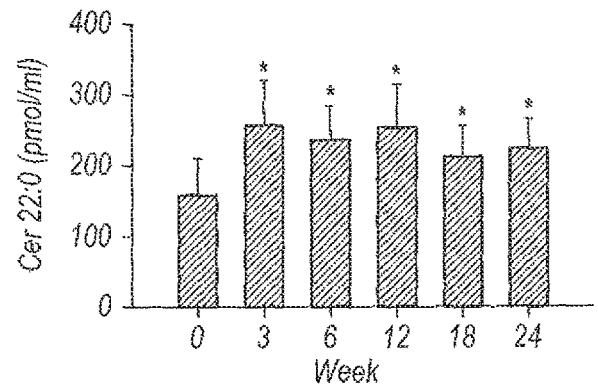
FIG. 3B provides data for serum ceramide 22:0 levels in an embodiment according to Example 1 (*=denotes $P<0.05$)
Figure 3C:
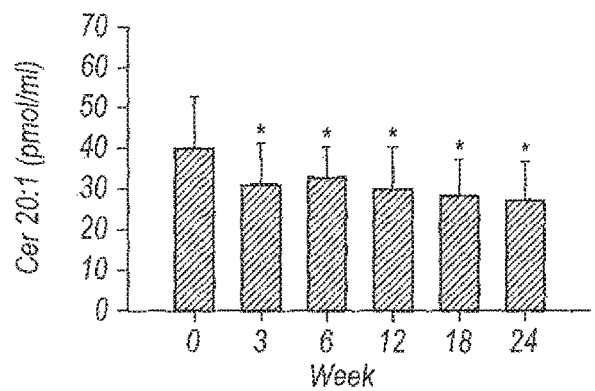
FIG. 3C provides provide data for serum ceramide 20:1 levels in an embodiment according to Example 1 (*=denotes $P<0.05$)
Figure 3D:
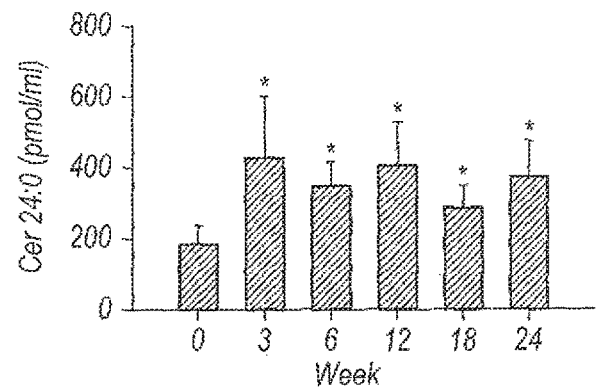
FIG. 3D provides data for serum ceramide 24:0 levels in an embodiment according to Example 1 (*=denotes $P<0.05$)
Figure 3E:
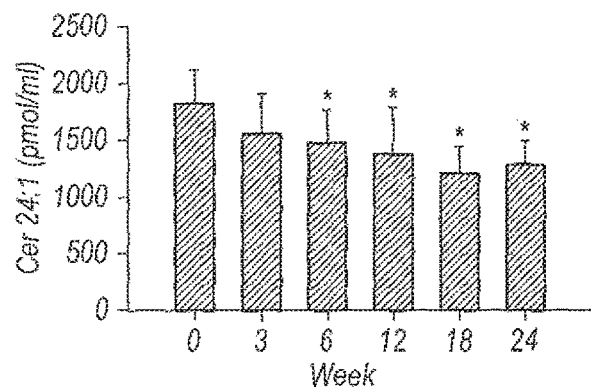
FIG. 3E provides data for serum ceramide 24:1 levels in an embodiment according to Example 1 (*=denotes $P<0.05$); and, FIG. 3F provides data for serum ceramide 26:0 levels in an embodiment according to Example 1 (*=denotes $P<0.05$).
Figure 3F:
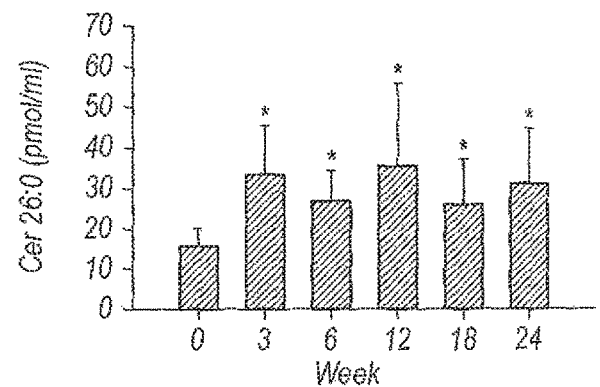
Figure 4A:
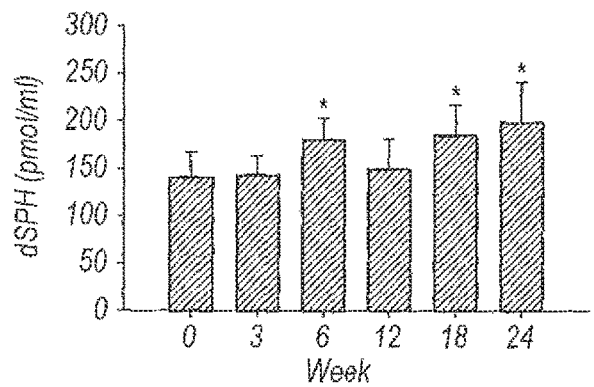
FIG. 4A provides data for serum sphingolipid dihydrosphingosine (dSPH) levels in an embodiment according to Example 1.
Figure 4B:
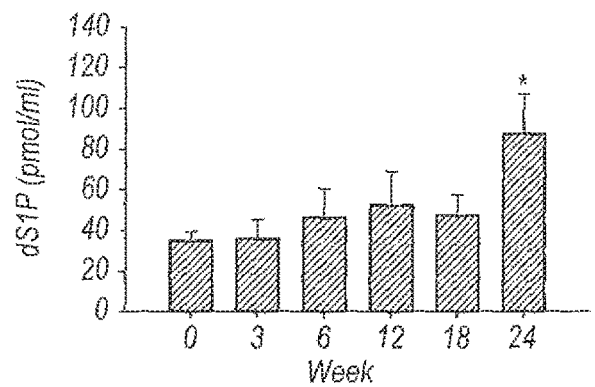
FIG. 4B provides data for serum dihydrosphingosine 1-phosphoste (dS1P) levels in an embodiment according to Example 1.
Figure 4C:
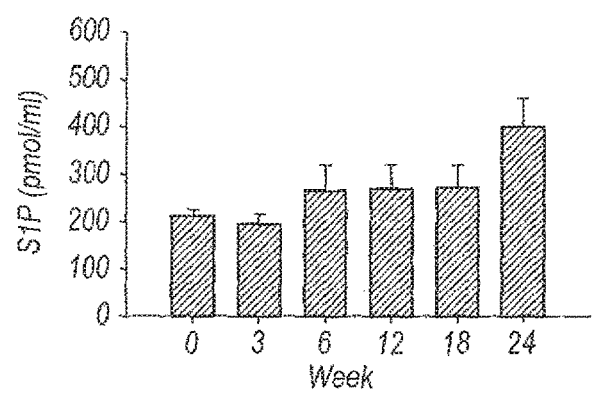
FIG. 4C provides data for sphingosine 1-phosphate (SIP) levels in an embodiment according to Example 1; and, FIG. 4D provides total ceramides and total sphingonsines represented as the sum of dSPH, dS1P, sphingosine, and S1P (*=denotes $P<0.05$), in an embodiment according to Example 1, where data are reported as mean±SD.
Figure 4D:
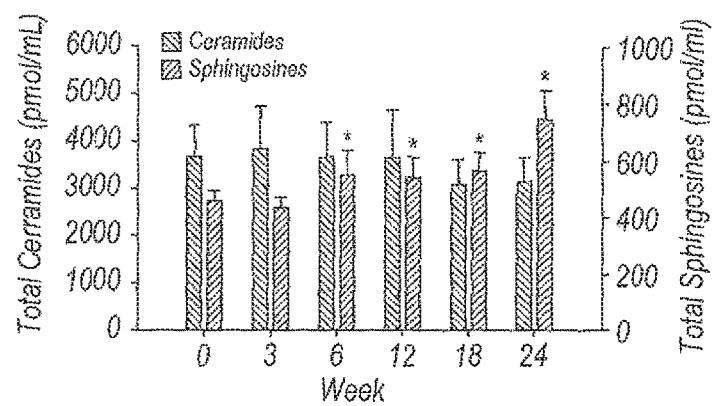

Compositions including one or more odd chain fatty acid, and associated methods for treatment of metabolic syndrome are provided.

It is an object of certain of the embodiments to provide a method for detecting protective and risk factors against and for metabolic syndrome and hyperferritinemia in mammal subjects such as dolphins and humans. An object of certain of the embodiments is to provide a method for treating metabolic syndrome and/or hyperferritinemia in mammal subjects, such as dolphins and humans. An object of certain of the embodiments is to provide a method for detecting metabolic syndrome and/or hyperferritinemia in mammal subjects, such as for dolphins and humans that increases the level of heptadecanoic acid of the subject sera. An object of certain of the embodiments is to provide a method for detecting and treating hyperferritinemia without resorting to phlebotomy. An object of certain of the embodiments is to provide a heptadecanoic acid supplement for detecting and treating metabolic syndrome and hyperferritinemia. An object of certain of the embodiments is to provide a method for detecting and treating metabolic syndrome and/or hyperferritinemia in mammal subjects, such as dolphins and humans that is easy to accomplish in a cost-effective manner. An object of certain of the embodiments is to provide a method for modulating markers of metabolic syndrome in a subject. An object of certain of the embodiments is to provide a method for detecting metabolic syndrome in a subject. An object of certain of the embodiments is to provide a method for treatment of metabolic syndrome in a subject. An object of certain of the embodiments is to provide a method for prophylaxis of metabolic syndrome in a subject. An object of certain of the embodiments is to provide a method for increasing an odd chain fatty acid in the sera of a subject. An object of certain of the embodiments is to provide a method for detecting or treating hyperferritinemia. An object of certain of the embodiments is to provide an odd chain fatty acid substantially free from other fatty acids. An object of certain of the embodiments is to provide one or more odd chain fatty acids substantially free from even chain fatty acids.

One or more than one of the aforementioned objects is provided by or achieved by the various compositions, methods, and uses as described herein.

Definitions

The term "alcohol" as used herein is a broad term, and is to be given its ordinary and customary meaning to a person of ordinary skill in the art (and is not to be limited to a special or customized meaning), and refers without limitation to any compound as described herein incorporating one or more hydroxy groups, or being substituted by or functionalized to include one or more hydroxy groups.

The term "derivative" as used herein is a broad term, and is to be given its ordinary and customary meaning to a person of ordinary skill in the art (and is not to be limited to a special or customized meaning), and refers without limitation to any compound as described herein incorporating one or more derivative groups, or being substituted by or functionalized to include one or more derivative groups. Derivatives include but are not limited to esters, amides, anhydrides, acid halides, thioesters, and phosphates.

The term "hydrocarbon" as used herein is a broad term, and is to be given its ordinary and customary meaning to a person of ordinary skill in the art (and is not to be limited to a special or customized meaning), and refers without limitation to any moiety comprising only carbon and hydrogen atoms. A functionalized or substituted hydrocarbon moiety has one or more substituents as described elsewhere herein.

The term "lipid" as used herein is a broad term, and is to be given its ordinary and customary meaning to a person of ordinary skill in the art (and is not to be limited to a special or customized meaning), and refers without limitation to saturated and unsaturated oils and waxes, derivatives, amides, glycerides, fatty acids, fatty alcohols, sterol and sterol derivatives, tocopherols, carotenoids, among others.

The terms "pharmaceutically acceptable" as used herein is a broad term, and is to be given its ordinary and customary meaning to a person of ordinary skill in the art (and is not to be limited to a special or customized meaning), and refers without limitation to those compounds, materials, compositions, and/or dosage forms which are, within the scope of sound medical judgment, suitable for contact with the tissues of and/or for consumption by human beings and animals without excessive toxicity, irritation, allergic response, or other problem complications commensurate with a reasonable risk/benefit ratio.

The terms "pharmaceutically acceptable salts" and "a pharmaceutically acceptable salt thereof" as used herein are broad terms, and are to be given their ordinary and customary meaning to a person of ordinary skill in the art (and is not to be limited to a special or customized meaning), and refer without limitation to salts prepared from pharmaceutically acceptable, non-toxic acids or bases. Suitable pharmaceutically acceptable salts include metallic salts, e.g., salts of aluminum, zinc, alkali metal salts such as lithium, sodium, and potassium salts, alkaline earth metal salts such as calcium and magnesium salts; organic salts, e.g., salts of lysine, N,N'-dibenzylethylenediamine, chloroprocaine, choline, diethanolamine, ethylenediamine, meglumine (N-methylglucamine), procaine, and tris; salts of free acids and bases; inorganic salts, e.g., sulfate, hydrochloride, and hydrobromide; and other salts which are currently in widespread pharmaceutical use and are listed in sources well known to those of skill in the art, such as, for example, The Merck Index. Any suitable constituent can be selected to make a salt of the therapeutic agents discussed herein, provided that it is non-toxic and does not substantially interfere with the desired activity. In addition to salts, pharmaceutically acceptable precursors and derivatives of the compounds can be employed. Pharmaceutically acceptable amides, lower alkyl derivatives, and protected derivatives can also be suitable for use in compositions and methods of preferred embodiments. While it may be possible to administer the compounds of the preferred embodiments in the form of pharmaceutically acceptable salts, it is generally preferred to administer the compounds in neutral form.

The term "pharmaceutical composition" as used herein is a broad term, and is to be given its ordinary and customary meaning to a person of ordinary skill in the art (and is not to be limited to a special or customized meaning), and refers without limitation to a mixture of one or more compounds disclosed herein with other chemical components, such as diluents or carriers. The pharmaceutical composition facilitates administration of the compound to an organism. Pharmaceutical compositions can also be obtained by reacting compounds with inorganic or organic acids or bases. Pharmaceutical compositions will generally be tailored to the specific intended route of administration.

As used herein, a "carrier" as used herein is a broad term, and is to be given its ordinary and customary meaning to a person of ordinary skill in the art (and is not to be limited to a special or customized meaning), and refers without limitation to a compound that facilitates the incorporation of a compound into cells or tissues. For example, without limitation, dimethyl sulfoxide (DMSO) is a commonly utilized carrier that facilitates the uptake of many organic compounds into cells or tissues of a subject. Water, saline solution, ethanol, and mineral oil are also carriers employed in certain pharmaceutical compositions.

As used herein, a "diluent" as used herein is a broad term, and is to be given its ordinary and customary meaning to a person of ordinary skill in the art (and is not to be limited to a special or customized meaning), and refers without limitation to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" as used herein is a broad term, and is to be given its ordinary and customary meaning to a person of ordinary skill in the art (and is not to be limited to a special or customized meaning), and refers without limitation to a substance that is added to a pharmaceutical composition to provide, without limitation, bulk, consistency, stability, binding ability, lubrication, disintegrating ability etc., to the composition. A "diluent" is a type of excipient.

As used herein, a "subject" as used herein is a broad term, and is to be given its ordinary and customary meaning to a person of ordinary skill in the art (and is not to be limited to a special or customized meaning), and refers without limitation to an animal that is the object of treatment, observation or experiment. "Animal" includes cold- and warm-blooded vertebrates and invertebrates such as fish, shellfish, reptiles and, in particular, mammals. "Mammal" includes, without limitation, dolphins, mice, rats, rabbits, guinea pigs, dogs, cats, sheep, goats, cows, horses, primates, such as monkeys, chimpanzees, and apes, and, in particular, humans. In some embodiments, the subject is human.

As used herein, the terms "treating," "treatment," "therapeutic," or "therapy" are broad terms, and are to be given their ordinary and customary meaning (and are not to be limited to a special or customized meaning) and, without limitation, do not necessarily mean total cure or abolition of the disease or condition. Any alleviation of any undesired markers, signs or symptoms of a disease or condition, to any extent, can be considered treatment and/or therapy. Furthermore, treatment may include acts that may worsen the patient's overall feeling of well-being or appearance.

The terms "therapeutically effective amount" and "effective amount" as used herein are broad terms, and are to be given its ordinary and customary meaning to a person of ordinary skill in the art (and are not to be limited to a special or customized meaning), and are used without limitation to indicate an amount of an active compound, or pharmaceutical agent, that elicits the biological or medicinal response indicated. For example, a therapeutically effective amount of compound can be the amount needed to prevent, alleviate or ameliorate markers or symptoms of a condition or prolong the survival of the subject being treated. This response may occur in a tissue, system, animal or human and includes alleviation of the signs or symptoms of the disease being treated. Determination of a therapeutically effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The term "solvents" as used herein is a broad term, and is to be given its ordinary and customary meaning to a person of ordinary skill in the art (and is not to be limited to a special or customized meaning), and refers without limitation to compounds with some characteristics of solvency for other compounds or means, that can be polar or nonpolar, linear or branched, cyclic or aliphatic, aromatic, naphthenic and that includes but is not limited to: alcohols, derivatives, diesters, ketones, acetates, terpenes, sulfoxides, glycols, paraffins, hydrocarbons, anhydrides, heterocyclics, among others.

Any percentages, ratios or other quantities referred to herein are on a weight basis, unless otherwise indicated.

Odd Chain Fatty Acids

Odd chain fatty acids are saturated and unsaturated fatty acids (see, e.g., Jenkins B, West J, Koulman A (2015), A review of odd-chain fatty acid metabolism and the role of pentadecanoic acid (C15:0) and heptadecanoic acid (C17:0) in health and disease, Molecules 20:2425-44). As provided herein, fatty acids are referred to and described using conventional nomenclature as is employed by one of skill in the art. A saturated fatty acid includes no carbon-carbon double bonds. An unsaturated fatty acid includes at least one carbon-carbon double bond. A monounsaturated fatty acid includes only one carbon-carbon double bond. A polyunsaturated fatty acid includes two or more carbon-carbon double bonds. Double bonds in fatty acids are generally cis; however, trans double bonds are also possible. The position of double bonds can be indicated by $\Delta n$, where n indicates the lower numbered carbon of each pair of double-bonded carbon atoms. A shorthand notation specifying total # carbons:# double bonds, $\Delta$ double bond positions can be employed. For example, 20:4$\Delta$ 5,8.11.14 refers to a fatty acid having 20 carbon atoms and four double bonds, with the double bonds situated between the 5 and 6 carbon atom, the 8 and 9 carbon atom, the 11 and 12 carbon atom, and the 14 and 15 carbon atom, with carbon atom 1 being the carbon of the carboxylic acid group. Stearate (octadecanoate) is a saturated fatty acid. Oleate (cis-$\Delta$9-octadecenoate) is a monounsaturated fatty acid, linolenate (all-cis-$\Delta$9, 12,15-octadecatrienoate) is a polyunsaturated fatty acid.

An odd chain fatty acid may be referred to by various names, for example, heptadecanoic acid may be referred to as heptadecylic acid and n-heptadecylic acid, or C17:0. An odd chain fatty acid may be referred to by lipid numbers, as known in the art. Examples of odd chain fatty acids are margaric acid (heptadecanoic acid, C17:0), pelargonate (nonanoic acid, C9:0), undecanoic acid (C11:0), nonadecanoic acid (C19:0), arachidonate ((5Z,8Z,11Z,14Z)-icosa-5,8,11,14-tetraenoic acid), adrenate (all-cis-7,10,13,16-docosatetraenoic acid), and osbond acid (all-cis-4,7,10,13,16-docosapentaenoic acid). Generally, the one or more odd chain fatty acids have from 9 carbon atoms to 31 carbon atoms (9, 11, 13, 15, 17, 19, 21, 23, 25, 27, 29, or 31 carbon atoms), for example, from 15 to 21 carbon atoms, for example 17 carbon atoms; however, in certain embodiments higher or lower odd numbers of carbon atoms can be acceptable. Generally, the one or more odd chain fatty acids are saturated; however, in certain embodiments mono or polyunsaturated odd chain fatty acids can be acceptable.

An odd chain fatty acid may include saturated or unsaturated hydrocarbon chains. An odd chain fatty acid may be present as a carboxylic derivative. An odd chain fatty acid may be present as a salt, for example, at the carboxylic group. In some embodiments, one odd chain fatty acid may be present, two odd chain fatty acids may be present, three odd chain fatty acids may be present, or more. In some embodiments, odd chain fatty acids in a mixture including a plurality of odd chain fatty acids may be distinguished by the amount of unsaturation, the length of the hydrocarbon chain, varying states of derivativeification, or by other structural features.

Odd chain fatty acids are found in trace amounts in some dairy products, including butter, and is a component of some fish oils (see, e.g., Mansson H L (2008), Fatty acids in bovine milk fat, Food Nutr. Res. 52:4, Luzia L A, Sampaia G R, Castellucci C M N, Tones E A F S (2013) The influence of season on the lipid profiles of five commercially important species of Brazilian fish. Food Chem. 83:93-97). Studies have demonstrated that increasing daily dietary intake of foods with odd chain fatty acids successfully increases serum levels (see, e.g., Benatar J. R., Stewart R A H. (2014), The effects of changing dairy intake on trans and saturated fatty acid levels—results from a randomized controlled study. Nutr. J. 13:32).

The prevalence of various fatty acids in the diet has been correlated to the occurrence of metabolic syndrome in subjects (see, e.g., Forouhi N, Koulman A, Sharp S, Imamura F, Kroger J, Schulze M, et al. (2014), Differences in the prospective association between individual plasma phospholipid saturated fatty acids and incident type 2 diabetes: the EPIC-InterAct case-cohort study. Lancet Diabetes Endocrinol. 2:810-8). Indeed, whole-fat dairy consumption has been correlated with a decreased risk of metabolic syndrome markers (see, e.g., Kratz M, Marcovina S, Nelson J E, Yeh M M, Kowdley K V, Callahan H S, et al. (2014), Dairy fat intake is associated with glucose tolerance, hepatic and systemic insulin sensitivity, and liver fat but not beta-cell function in humans, Am. J. Clin. Nutr., 99: 1385-96).

A pure or purified odd chain fatty acid may exist in various physical states. For example, heptadecanoic acid exists as an off-white powder that is stable at room temperature; this compound can be purchased in forms suitable for research purposes in small amounts from some commercial suppliers (for example, from Sigma-Aldrich corp., of St. Louis, Mo.). Other odd chain fatty acids, or salts or derivatives thereof, may exist as oils, solids, crystalline solids, or gases.

An odd chain fatty acid, or its pharmaceutically acceptable salts or derivatives, may be provided in a purity (e.g., a percentage of the odd chain fatty acid, or its pharmaceutically acceptable salts or derivatives, in a bulk form) of at least about 10%, at least about 20%, at least about 30%, at least about 40%, at least about 50%, at least about 60%, at least about 70%, at least about 80%, at least about 90%, at least about 95%, at least about 98%, at least about 99%, at least about 99.9%, at least about 99.99%, or substantially pure, wherein substantially pure may include, but not be limited to, a product with impurities at a level such that no physiological effect from the presence of the impurities is detectable. A mixture of odd chain fatty acids, or pharmaceutically acceptable salts or derivatives thereof, may be present in a purity of at least about 10%, at least about 20%, at least about 30%>, at least about 40%, at least about 50%, at least about 60%, at least about 70%, at least about 80%, at least about 90%, at least about 95%, at least about 98%, at least about 99%, at least about 99.9%, at least about 99.99%, or substantially pure. An odd chain fatty acid, or a mixture thereof, or a pharmaceutically acceptable salt or derivative thereof, may be free from other fatty acids or fatty acid derivatives, may be free from triglycerides, or may be free from phospholipids. Without limitation, an odd chain fatty acid as provided herein may be substantially free from even chain fatty acids, singly or taken as a group; even chain fatty acids include, for example, myristic acid (C14:0), palmitic acid (C16:0), stearic acid (C18:0), or arachidic acid (C20:0). In some embodiments, an odd chain fatty acid as provided herein may be substantially free from short-chain fatty acids (SCFA), medium-chain fatty acids (MCFA), long-chain fatty acids (LCFA), or very long chain fatty acids (VLCFA).

An odd chain fatty acid, or a pharmaceutically acceptable salt or derivative thereof, may be from any source. In some embodiments, an odd chain fatty acid, or its pharmaceutically acceptable salts or derivatives, may be present in natural sources, may be isolated from natural sources, may be semi-synthetic, may be synthetic, or may be a mixture of one or more of these. An odd chain fatty acid, or its pharmaceutically acceptable salts or derivatives, may be produced in a laboratory, may be produced in nature, may be produced by enzymatic processes, may be produced by wild microbes, may be produced by genetically modified microbes, may be isolated from animal tissues, may be produced by chemical synthesis, or may be produced by a plurality of these processes.

An odd chain fatty acid may be derived from natural sources, e.g., fish oils, or can be synthesized by methods as are known in the art. In some embodiments, an odd chain fatty acid may be contaminated with even chain fatty acids, or other components present in unrefined or unpurified natural products. In such situations, it can be desirable to remove undesired components, or to increase the concentration of desired components using known separation or purification techniques.

In any compound described, all tautomeric forms are also intended to be included. Without limitation, all tautomers of carboxylic groups are intended to be included.

In any compound described herein having one or more double bond(s) generating geometrical isomers that can be defined as E or Z, each double bond may independently be E or Z, or a mixture thereof.

Where compounds disclosed herein have unfilled valencies, then the valencies are to be filled with hydrogens or isotopes thereof, e.g., hydrogen-1 (protium) and hydrogen-2 (deuterium).

An odd chain fatty acid, as described herein, includes crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

The compounds described herein can be labeled isotopically. In some circumstances, substitution with isotopes such as deuterium may afford certain therapeutic advantages resulting from greater metabolic stability, such as, for example, increased in vivo half-life or reduced dosage requirements. Isotopic substitution may be beneficial in monitoring subject response to administration of a compound, for example, by providing opportunity for monitoring of the fate of an atom in a compound. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Pharmaceutical Compositions Including One or More Odd Chain Fatty Acids

Formulations including an odd chain fatty acid, or a salt or derivative thereof, and at least one excipient are provided. It is generally preferred to administer the compounds of the embodiments in oral formulations; however, other routes of administration are also contemplated.

The pharmaceutical compositions described herein can be administered by themselves to a subject, or in compositions where they are mixed with other active agents, as in combination therapy, or with carriers, diluents, excipients or combinations thereof. Formulation is dependent upon the route of administration chosen. Techniques for formulation and administration of the compounds described herein are known to those skilled in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

The pharmaceutical compositions disclosed herein may be manufactured by a process that is itself known, e.g., by means of conventional mixing, dissolving, granulating, dragee-making, levigating, emulsifying, encapsulating, entrapping, tableting, or extracting processes. Many of the compounds used in the pharmaceutical combinations disclosed herein may be provided as salts with pharmaceutically acceptable counterions.

Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Contemplated herein is any combination of the forgoing, or other methods as would be known to one of ordinary skill in the art (see, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively).

In practice, an odd chain fatty acid, or a salt or derivative thereof, may be combined as the active ingredient in intimate admixture with a pharmaceutical carrier according to conventional pharmaceutical compounding techniques. The carrier can take a wide variety of forms depending on the form of preparation desired for administration. Thus, the pharmaceutical compositions provided herein can be presented as discrete units suitable for oral administration such as capsules, cachets or tablets each containing a predetermined amount of the active ingredient. Further, the compositions can be presented as an oil, a powder, as granules, as a solution, as a suspension in an aqueous liquid, as a non-aqueous liquid, as an oil-in-water emulsion, or as a water-in-oil liquid emulsion. In addition to the common dosage forms set out above, the compounds provided herein, or pharmaceutically acceptable salts or derivatives thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

A formulation may also be administered in a local rather than systemic manner, for example, via injection of the compound directly into the infected area, often in a depot or sustained release formulation. Furthermore, a targeted drug delivery system might be used, for example, in a liposome coated with a tissue specific antibody.

The pharmaceutical compositions may contain an odd chain fatty acid, or a salt or derivative thereof, in an amount effective for the desired therapeutic effect. In some embodiments, the pharmaceutical compositions are in a unit dosage form and comprise from about 0.1 mg or less to about 5000 mg or more per unit dosage form. In further embodiments, the pharmaceutical compositions comprise from about 1 to about 500 mg per unit dosage form or from about 500 to 5000 mg per unit dosage form. Such dosage forms may be solid, semisolid, liquid, an emulsion, or adapted for delivery via aerosol or the like for inhalation administration.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, lower alcohols, and water. Examples of gaseous carriers include carbon dioxide and nitrogen.

Pharmaceutical compositions provided herein can be prepared as solutions or suspensions of the active compound(s) in water. A suitable surfactant can be included such as, for example, hydroxypropylcellulose. Dispersions can also be prepared in glycerol, liquid polyethylene glycols, and mixtures thereof in oils. Further, a preservative can be included to, for example, prevent the detrimental growth of microorganisms.

Pharmaceutical compositions provided herein suitable for injectable use include sterile aqueous solutions or dispersions. Furthermore, the compositions can be in the form of sterile powders for the extemporaneous preparation of such sterile injectable solutions or dispersions. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound provided herein, or pharmaceutically acceptable salt or derivative thereof, can also be prepared in powder or liquid concentrate form for dilution.

Contemplated herein are compositions including an odd chain fatty acid or a salt or derivative thereof in combination with at least one additional active agent. An odd chain fatty acid, or a salt or derivative thereof, and the at least one additional active agent(s) may be present in a single formulation or in multiple formulations provided together, or may be unformulated. In some embodiments, an odd chain fatty acid, or a salt or derivative thereof, can be administered with one or more additional agents together in a single composition. For example, a compound of an odd chain fatty acid, or a salt or derivative thereof, can be administered in one composition, and at least one of the additional agents can be administered in a second composition. In a further embodiment, an odd chain fatty acid or a salt or derivative thereof and the at least one additional active agent(s) are co-packaged in a kit. For example, a drug manufacturer, a drug reseller, a physician, a compounding shop, or a pharmacist can provide a kit comprising a disclosed compound or product and another component for delivery to a patient.

Some embodiments described herein relate to a pharmaceutical composition, which can include a therapeutically effective amount of one or more compounds described herein (e.g., an odd chain fatty acid, or a pharmaceutically acceptable salt or derivative thereof) and a pharmaceutically acceptable carrier, diluent, excipient or combination thereof. The pharmaceutical composition can include an odd chain fatty acid or a salt or derivative thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition. In some embodiments, the pharmaceutical composition can include a plurality of odd chain fatty acids, or salts or derivatives thereof in, for example, >1%, ≥2%, ≥3%, ≥4%, ≥5%, ≥6%, ≥7%, ≥8%, ≥9%, ≥10%, ≥20%, ≥30%, ≥40%, ≥50%, ≥60%, ≥70%, ≥80%, ≥90%, ≥95%, or ≥98% of the composition.

Foodstuffs

Foodstuffs and other comestibles including an odd chain fatty acid, or a salt or derivative thereof, are provided, wherein an amount of the odd chain fatty acid in the foodstuff has been fortified (e.g., enriched or concentrated). An odd chain fatty acid provided herein may be added to foodstuffs for consumption by a subject. The odd chain fatty acid may be integrated into one or more ingredients of a foodstuff. The odd chain fatty acid may be prepared as an ingredient, or may be unprepared. The compound, or preparation including the compound, may be added prior to preparation, during preparation, or following preparation. Preparation may without limitation include cooking, mixing, flavoring, seasoning, blending, boiling, frying, baking, or other processes known in the art. Fortification is preferably at a level so as to provide a therapeutic daily dosage of the odd chain fatty acid as described elsewhere herein; however, beneficial effects may also be obtained at amounts below such dosages.

An odd chain fatty acid, or salt or derivative thereof, as provided herein may be present as a constituent in foodstuffs by operation of processes known in nature, for example, by altering the metabolic processes of a plant, animal, bacteria, or fungus. Genetic alteration of a plant, animal, bacteria, or fungus to increase the concentration of an odd chain fatty acid, or a salt or derivative thereof, is contemplated. By way of example, the odd chain fatty acid can be present in the foodstuff in a concentration of at least about 1%, at least about 2%, at least about 3%, at least about 4%, at least about 5%, at least about 6%, at least about 7%, at least about 8%, at least about 9%, at least about 10%, at least about 20%, at least about 30%, at least about 40%, at least about 50%, or higher, for example, 1% to 2% or 3% or 4% or 5% or 6% or 7% or 8% or 9% or 10% or 20% or 30% or 40% or 50%.

Indications

Provided herein are compositions and methods for treating conditions including but not limited to metabolic syndrome, diabetes type I, diabetes type II, obesity, pre-diabetes, glucose intolerance, gestational diabetes mellitus (GDM), impaired fasting glycemia (IFG), hyperferritinemia, impaired adiponectin production, postprandial hyperglycemia, dyslipidemia, post prandial dyslipidemia, hyperlipidemia, hypertriglyceridemia, post hypertriglyceridemia, insulin resistance, polycystic ovary syndrome (PCOS), non-alcoholic fatty liver disease (NAFL), non-alcoholic steatohepatitis (NASH), hypoinsulinemia, fatty liver disease, elevated glucose levels, elevated insulin levels, and elevated LDL triglyceride levels.

In some embodiments, the compositions and methods provided herein are indicated for treatment, prophylaxis, prevention or maintenance of metabolic syndrome.

Metabolic syndrome as described herein generally relates to a cluster of risk factors that are associated with a number of conditions as described herein, including but not limited to diabetes (especially type 2 diabetes), hypertension, cardiovascular disease, and other conditions such as polycystic ovary syndrome, fatty liver, cholesterol gallstones, asthma, sleep disturbances, some forms of cancer, ischemia, oxidative stress, atherosclerosis, obesity, abnormal lipid metabolism, and stroke (see, e.g., Grundy S. M, et al, Definition of Metabolic Syndrome (2004), Circulation, 109: 433-438). Risk factors of metabolic syndrome include abdominal (central) obesity, elevated blood pressure, advanced age, and smoking. Indicators of metabolic syndrome, which may but need not present, include insulin resistance, elevated fasting plasma glucose, glucose intolerance, high serum triglycerides, abnormal serum lipids, decreased high-density lipoprotein (HDL) levels, body mass index (BMI), proinflammatory state, and prothrombotic state.

Metabolic syndrome is also correlated with hyperferritinemia (with or without iron overload), which is itself associated with impaired production of the insulin sensitizing hormone adiponectin. Not wishing to be bound by theory, it appears that increased adiponectin levels are associated with better glycemic control and better lipid profiles (Schulze, M. B., et al (2004), Relationship between adiponectin and glycemic control, blood lipids, and inflammatory markers in men with type 2 diabetes. Diabetes Care 27, 1680-1687; Mantzoros, et al (2005), Circulating adiponectin levels are associated with better glycemic control, more favorable lipid profile, and reduced inflammation in women with type 2 diabetes. J. Clin. Endocrinol. Metab. 90, 4542-4548).

While a cluster of signs and symptoms may coexist in an individual subject, in many cases only one or a few symptoms may dominate, due to individual differences in vulnerability of the many physiological systems affected.

Insulin resistance can be defined in many different ways, including impaired glucose metabolism (reduced clearance of glucose and/or the failure to suppress glucose production), the inability to suppress lipolysis in tissues, defective protein synthesis, altered cell differentiation, aberrant nitric oxide synthesis affecting regional blood flow, as well as abnormal cell cycle control and proliferation. Insulin resistance may also be indicated by serum protein concentrations of, for example, fibroblast growth factor 21 ("FGF21"), total adiponectin, and % unmodified adiponectin.

Serum lipid concentrations that may indicate metabolic syndrome and associated conditions include, for example, ceramides, and sphingolipids, for example, sphingosine, dihydrosphingosine, sphingosine-1-phosphate, and dihydrosphingosine-1-phosphate.

Disease symptoms secondary to hyperglycemia or other conditions may also occur in patients with metabolic syndrome. Because the compositions and methods provided herein help to reduce hyperglycemia in diabetes and other conditions related to metabolic syndrome, they are useful for prevention and amelioration of complications of these conditions. The compounds and methods provided herein are useful for prevention or amelioration of virtually any symptom that may be due to, or exacerbated by, metabolic syndrome and related conditions.

Serum odd chain fatty acids levels are correlated with improved indices for metabolic syndrome. However, the mechanism by which odd chain fatty acids act to inhibit or lessen metabolic syndrome or markers of metabolic syndrome is not presently well understood. The methods and markers provided herein are not to be construed as limited to any particular mechanism, mode of action, or theory. Accordingly, methods of treating, preventing or ameliorating metabolic syndrome are provided.

Provided herein are compositions and methods for preventing or treating diabetes in a wide range of subjects, including in particular a human patient that has, has had, is suspected of having, or who is pre-disposed to developing diabetes. Diabetes mellitus may be referred to as, for example, insulin-dependent diabetes mellitus (EDDM or type I diabetes) and non-insulin-dependent diabetes mellitus (NIDDM, or type II diabetes). Examples of disorders related to diabetes mellitus have been described and include, but are not limited to, impaired glucose tolerance (IGT), maturity-onset diabetes of youth (MODY), leprechaunism (insulin receptor mutation), tropical diabetes, diabetes secondary to a pancreatic disease or surgery, diabetes associated with a genetic syndrome (e.g., Prader-Willi syndrome), pancreatitis, diabetes secondary to endocrinopathies, adipositas, and metabolic syndrome.

Diabetic subjects appropriate for treating using the compositions and methods provided herein may be identified by the risk factors, indices and markers provided herein, and by other indications available to clinicians, and are characterized by, e.g., fasting hyperglycemia, impaired glucose tolerance, glycosylated hemoglobin, and, in some instances, ketoacidosis associated with trauma or illness. Hyperglycemia or high blood sugar is a condition in which an excessive amount of glucose circulates in the blood plasma. This is generally considered to be a blood glucose level of 10+ mmol/L, but symptoms and effects may not start to become noticeable until later numbers such as 15-20+ mmol/L. NIDDM patients have an abnormally high blood glucose concentration when fasting and delayed cellular uptake of glucose following meals or after a diagnostic test known as the glucose tolerance test. NIDDI is diagnosed based on recognized criteria (American Diabetes Association, Physician's Guide to Insulin-Dependent (Type I) Diabetes, 1988; American Diabetes Association, Physician's Guide to Non-Insulin-Dependent (Type II) Diabetes, 1988).

In some embodiments, the compositions and methods provided herein are indicated for treatment, prevention and or maintenance of conditions, disorders, diseases and defects associated with energy homeostasis. Energy homeostasis generally relates to the signal pathways, molecules and hormones associated with food intake and energy expenditure. Disorders, diseases and defects associated with energy homeostasis include but are not limited to diabetes type I, diabetes type II, prediabetes, impaired fasting glycemia (IFG), impaired post-prandial glucose, and gestational diabetes. In some instances the compositions and methods provided herein are indicated for treatment, prevention and or maintenance of diabetes type I or type II.

In some embodiments, the compositions and methods provided herein are indicated for treatment, prevention and or maintenance of conditions, disorders, diseases and defects associated with fuel homeostasis. Disorders, diseases and defects associated with fuel homeostasis include but are not limited to non-alcoholic fatty liver disease (NAFL), non-alcoholic steatohepatitis (NASH), hyperlipidemia, post hypertriglyceridemia, hypertriglyceridemia, insulin resistance and polycystic ovary syndrome (PCOS).

In some embodiments, the compositions and methods provided herein are indicated for treatment, prevention, or maintenance of hyperferritinemia. High ferritin and iron overload have been associated with metabolic syndrome and diabetes in humans. It is unknown precisely why ferritin increases in some people and how high ferritin increases the risk of metabolic syndrome. While not wishing to be bound by theory, it is believed that direct injury to the liver and pancreas from excessive deposition, or indirect injury from increased oxidative radicals, may be causative factors. In some embodiments, the compounds and methods provided herein lead to reduced serum iron; in some embodiments, the compounds and methods provided herein lead to reduced serum ferritin; in some embodiments, the compounds and methods provided herein ameliorate hyperferritinemia without phlebotomy.

Elevated triglyceride (e.g., LDL) is an important risk factor for atherosclerosis and myocardial infarction. Provided herein are compositions and methods useful for reducing circulating triglycerides in hyperlipidemic patients. Cholesterol-lowering drugs such as HMG-CoA reductase inhibitors ("statins") can be administered to subjects in addition to compounds provided herein, optionally incorporated into the same pharmaceutical composition.

In some embodiments provided herein, the subject may be a dolphin; however, it is generally contemplated that the methods, uses, and compositions of the embodiments are applied to humans. Like human subjects, bottlenose dolphin (*Tursiops truncatus*) subjects can also be susceptible to metabolic syndrome, including high insulin, glucose, triglycerides, fatty liver disease, and iron overload. Iron overload in dolphins, involving excessive iron deposition primarily in the liver's Kupffer cells, can be progressive with age and can be associated with elevated insulin, lipids, and liver enzymes. This disease is associated with neither mutations in the HFE gene nor increases in studied acute phase proteins. Similar to humans, iron overload in dolphins is treated with phlebotomy, and repeated treatments are needed throughout life due to returning elevations of serum ferritin. The underlying causes of iron overload and hyperferritinemia in dolphins are unknown.

In some embodiments, the condition treated is metabolic syndrome.

In some embodiments, the condition treated is metabolic syndrome as indicated by the markers provided herein.

In some embodiments, the methods provided herein modulate markers of metabolic syndrome when the markers provide a clinical indication.

In some embodiments, the methods provided herein alleviate symptoms of metabolic syndrome.

In some embodiments, the methods provided herein reduce risk of metabolic syndrome.

In some embodiments, the condition treated is hyperferritinemia.

In some embodiments, the methods provided herein increase levels of serum odd chain fatty acids.

In some embodiments, the methods provided herein improve insulin sensitivity.

In some embodiments, the compositions and methods provided herein modulate a marker of metabolic syndrome. In certain embodiments, the marker is serum or red blood cell membrane odd chain fatty acid percentage, serum concentration of an odd chain fatty acid, serum total odd chain fatty acid, serum ferritin, serum iron, transferritin saturation, serum glucose (for example fasting glucose), serum triglycerides, blood pressure, adiponectin, HDL cholesterol, microalbuminuria (i.e., elevated albumin excretion in the urine), CRP (C reactive protein), IL-6 and TNFα (and other cytokines associated with insulin resistance), c-Jun N-terminal kinase (JNK), ATM (Ataxia Telangiectasia Mutated) or monocyte-chemoattractant protein-1. In some embodiments, the odd chain fatty acid is measured as a constituent of glycolipids. In further embodiments, the odd chain fatty acid is measured as a constituent of phospholipids.

In some embodiments, the methods provided herein include the step of measuring the concentration of a marker of metabolic syndrome. One of skill in the art will be able to perform suitable methods for such measurements, including but not limited to those described herein.

Provided herein are methods for treating including the step of administering a dose of an odd chain fatty acid at a predetermined interval, or at an interval left to the discretion of the subject.

In some embodiments, the compounds and methods provided herein may provide a threshold serum or red blood cell membrane percentage of an odd chain fatty acid relative to all serum or red blood cell membrane fatty acids, respectively. For example, the threshold value may be a value of about 0.05% or lower to 90% or higher, e.g., a value of at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1.0%, at least about 1.1%, at least about 1.2%, at least about 1.3%, at least about 1.4%, at least about 1.5%, at least about 1.6%, at least about 1.7%, at least about 1.8%, at least about 1.9%, at least about 2.1%, at least about 2.2%, at least about 2.3%, at least about 2.4%, at least about 2.5%, at least about 2.6%, at least about 2.7%, at least about 2.8%, at least about 2.9%, at least about 3.0%, at least about 3.5%, at least about 4.0%, at least about 4.5%, at least about 5%, at least about 6%, at least about 7%, at least about 8%, at least about 9%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, or more than 90%.

In some embodiments, the compounds and methods provided herein may provide an increase above a baseline value (e.g., pretreatment value in a patient being treated, or general value observed in a particular patient population) in a serum concentration of an odd chain fatty acid, or red blood cell membrane concentration of an odd chain fatty acid. For example, a serum odd chain fatty acid or red blood cell membrane concentration of an odd chain fatty acid may be increased by at least about 1 µg/ml, at least about 2 µg/ml, at least about 3 µg/ml, at least about 4 µg/ml, at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, or more than 50 µg/ml. In some embodiments, the serum concentration of an odd chain fatty acid, or red blood cell membrane concentration of an odd chain fatty acid may increase above a baseline value (e.g., pretreatment value in a patient being treated, or general value observed in a particular patient population) by at least about $0.01 \times 10^{-4}$ M, at least about $0.05 \times 10^{-4}$ M, at least about $0.1 \times 10^{-4}$ M, at least about $0.2 \times 10^{-4}$ M, at least about $0.3 \times 10^{-4}$ M, at least about $0.4 \times 10^{-4}$ M, at least about $0.5 \times 10^{-4}$ M, at least about $0.6 \times 10^{-4}$ M, at least about $0.7 \times 10^{-4}$ M, at least about $0.8 \times 10^{-4}$ M, at least about $0.9 \times 10^{-4}$ M, at least about $1 \times 10^{-4}$ M, at least about $2 \times 10^{-4}$ M, or at least about $3 \times 10^{-4}$ M.

In some embodiments, the compounds and methods provided herein may provide an increase in serum total odd chain fatty acids, or red blood cell membrane total odd chain fatty acids. For example, serum total odd chain fatty acids, or red blood cell membrane total odd chain fatty acids, may be increased above a baseline value (e.g., pretreatment value in a patient being treated, or general value observed in a particular patient population) by at least about 5 µg/ml, at least about 6 µg/ml, at least about 7 µg/ml, at least about 8 µg/ml, at least about 9 µg/ml, at least about 10 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, at least about 50 µg/ml, at least about 60 µg/ml, at least about 70 µg/ml, at least about 80 µg/ml, at least about 90 µg/ml, at least about 100 µg/ml, at least about 150 µg/ml, at least about 200 µg/ml, at least about 250 µg/ml, at least about 300 µg/ml, at least about 350 µg/ml, at least about 400 µg/ml, at least about 450 µg/ml, at least about 500 µg/ml, or more than 500 µg/ml.

In some embodiments, the compounds and methods provided herein may provide an increase above a baseline value (e.g., pretreatment value in a patient being treated, or general value observed in a particular patient population) in a serum or red blood cell membrane odd chain fatty acids relative to all serum or red blood cell membrane fatty acids, respectively. For example, a serum or red blood cell membrane odd chain fatty acid may be increased above a baseline value (e.g., pretreatment value in a patient being treated, or general value observed in a particular patient population) by at least about 0.01%, at least about 0.05%, at least about 0.1%, at least about 0.2%, at least about 0.3%, at least about 0.4%, at least about 0.5%, at least about 0.6%, at least about 0.7%, at least about 0.8%, at least about 0.9%, at least about 1%, at least about 1.1%, at least about 1.2%, at least about 1.3%, at least about 1.4%, at least about 1.5%, at least about 1.6%, at least about 1.7%, at least about 1.8%, at least about 1.9%, at least about 2%, at least about 2.1%, at least about 2.2%, at least about 2.3%, at least about 2.4%, at least about 2.5%, at least about 2.6%, at least about 2.7%, at least about 2.8%, at least about 2.9%, at least about 3%, at least about 3.5%, at least about 4%, at least about 4.5%, at least about 5%, or more than 5%.

In some embodiments, the compounds and methods provided herein may provide a reduction in serum insulin. For example, serum insulin may be reduced below a baseline value (e.g., pretreatment value in a patient being treated, or general value observed in a particular patient population) by at least about 0.1 µIU/ml, at least about 0.2 µIU/ml, at least about 0.3 µIU/ml, at least about 0.4 µM/ml, at least about 0.5 µIU/ml, at least about 0.6 µIU/ml, at least about 0.7 µM/ml, at least about 0.8 µIU/ml, at least about 0.9 µIU/ml, at least about 1.0 µIU/ml, at least about 1.1 µIU/ml, at least about 1.2 µIU/ml, at least about 1.3 µIU/ml, at least about 1.4 µIU/ml, at least about 1.5 µIU/ml, at least about 2 µIU/ml, at least about 2.5 µIU/ml, at least about 3.0 µIU/ml, at least about 3.5 µIU/ml, at least about 4 PU/ml, at least about 5 µIU/ml, at least about 6 µIU/ml, at least about 7 µIU/ml, at least about 8 µIU/ml, at least about 9 µIU/ml, at least about 10 µIU/ml, at least about 11 µIU/ml, at least about 12 µIU/ml, at least about 13 µM/ml, at least about 14 µIU/ml, at least about 15 µM/ml, at least about 16 µIU/ml, at least about 17 µIU/ml, at least about 18 µIU/ml, at least about 19 µIU/ml, at least about 20 µIU/ml, at least about 25 µIU/ml, at least about 30 µIU/ml, or more than 30 µIU/ml.

In some embodiments, the compounds and methods provided herein may provide a reduction in serum triglycerides. For example, serum triglycerides may be reduced below a baseline value (e.g., pretreatment value in a patient being treated, or general value observed in a particular patient population) by at least about 1 mg/dl, at least about 3 mg/dl, at least about 4 mg/dl, at least about 5 mg/dl, at least about 10 mg/dl, at least about 15 mg/dl, at least about 20 mg/dl, at least about 25 mg/dl, at least about 30 mg/dl, at least about 35 mg/dl, at least about 40 mg/dl, at least about 45 mg/dl, at least about 50 mg/dl, at least about 60 mg/dl, at least about 70 mg/dl, at least about 80 mg/dl, at least about 90 mg/dl, at least about 100 mg/dl, at least about 110 mg/dl, at least about 120 mg/dl, at least about 130 mg/dl, at least about 140 mg/dl, at least about 150 mg/dl, at least about 200 mg/dl, at least about 250 mg/dl, at least about 300 mg/dl, or more than 300 mg/dl.

In some embodiments, the compounds and methods provided herein may provide a reduction in serum ferritin. For example, serum ferritin may be reduced below a baseline value (e.g., pretreatment value in a patient being treated, or general value observed in a particular patient population) by at least about 10 ng/ml, at least about 100 ng/ml, at least about 200 ng/ml, at least about 300 ng/ml, at least about 400 ng/ml, at least about 500 ng/ml, at least about 600 ng/ml, at least about 700 ng/ml, at least about 800 ng/ml, at least about 900 ng/ml, at least about 1000 ng/ml, at least about 1100 ng/ml, at least about 1200 ng/ml, at least about 1300 ng/ml, at least about 1400 ng/ml, at least about 1500 ng/ml, at least about 2000 ng/ml, at least about 2500 ng/ml, at least about 3000 ng/ml, at least about 3500 ng/ml, at least about 4000 ng/ml, at least about 4500 ng/ml, at least about 5000 ng/ml, at least about 6000 ng/ml, at least about 7000 ng/ml, at least about 8000 ng/ml, at least about 9000 ng/ml, at least about 10000 ng/ml, or more than 10000 ng/ml.

In some embodiments, the compounds and methods provided herein may provide a reduction in serum iron. For example, serum iron may be reduced below a baseline value (e.g., pretreatment value in a patient being treated, or general value observed in a particular patient population) by at least about 1 µg/dl, at least about 5 µg/dl, at least about 10 µg/dl, at least about 15 µg/dl, at least about 20 µg/dl, at least about 25 µg/dl, at least about 30 µg/dl, at least about 35 µg/dl, at least about 40 µg/dl, at least about 45 µg/dl, at least about 50 µg/dl, at least about 60 µg/dl, at least about 70 µg/dl, at least about 80 µg/dl, at least about 90 µg/dl, at least about 100 µg/dl, or more than 100 µg/dl.

In some embodiments, the compounds and methods provided herein may provide a reduction in transferritin saturation. For example, transferritin saturation may be reduced below a baseline value (e.g., pretreatment value in a patient being treated, or general value observed in a particular patient population) by at least about 5%, 10%, 15%, 20%, 25%, 30%, 35%, 40%, 50%, or more than 50%.

In some embodiments, the compounds and methods provided herein may provide an increase in serum total adiponectin. For example, serum total adiponectin may be increased above a baseline value (e.g., pretreatment value in a patient being treated, or general value observed in a particular patient population) by at least about 10 pmol/ml, at least about 50 pmol/ml, at least about 60 pmol/ml, at least about 70 pmol/ml, at least about 80 pmol/ml, at least about 90 pmol/ml, at least about 100 pmol/ml, at least about 110 pmol/ml, at least about 120 pmol/ml, at least about 130 pmol/ml, at least about 140 pmol/ml, at least about 150 pmol/ml, at least about 200 pmol/ml, at least about 250 pmol/ml, at least about 300 pmol/ml, at least about 350 pmol/ml, at least about 400 pmol/ml, at least about 450 pmol/ml, at least about 500 pmol/ml, at least about 550 pmol/ml, at least about 600 pmol/ml, at least about 650 pmol/ml, at least about 700 pmol/ml, at least about 750 pmol/ml, at least about 800 pmol/ml, at least about 850 pmol/ml, at least about 900 pmol/ml, at least about 950 pmol/ml, at least about 1000 pmol/ml, or more than 1000 pmol/ml.

In some embodiments, the compounds and methods provided herein may provide a reduction in percent unmodified adiponectin. For example, percent unmodified adiponectin may be reduced below a baseline value (e.g., pretreatment value in a patient being treated, or general value observed in a particular patient population) by at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, or more than 25%.

In some embodiments, the compounds and methods provided herein may provide a reduction in a serum ceramide in proportion to other serum ceramides. For example, a percent serum ceramide may be reduced below a baseline value (e.g., pretreatment value in a patient being treated, or general value observed in a particular patient population) by at least about 1%, at least about 5%, at least about 10%, at least about 15%, at least about 20%, at least about 25%, at least about 30%, at least about 35%, at least about 40%, at least about 45%, at least about 50%, or more than 50%.

In some embodiments, the compounds and methods provided herein may provide a reduction in a serum sphingosine. For example, a percent serum sphingosine may be reduced below a baseline value (e.g., pretreatment value in a patient being treated, or general value observed in a particular patient population) by at least about 5%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, at least about 50%, or more than 50%.

Combination Therapies

In some embodiments, the compounds disclosed herein, such as an odd chain fatty acid, or a salt or derivative thereof, or a pharmaceutical composition that includes a compound described herein, or a salt or derivative thereof, may be used in combination with one or more additional active agents. Examples of additional active agents that can be used in combination with a compound of an odd chain fatty acid, or a salt or derivative thereof, or a composition that includes a compound of an odd chain fatty acid, or a salt or derivative thereof, include, but are not limited to, agents currently used for treating metabolic syndrome and related conditions, as described herein and as otherwise known to medical science.

In some embodiments, a compound of an odd chain fatty acid, or a salt or derivative thereof, or a composition that includes a compound of an odd chain fatty acid, or a salt or derivative thereof, can be used with one, two, three or more additional active agents described herein. Such agents include, but are not limited to, a second odd chain fatty acid, or a salt or derivative thereof In some embodiments, a compound of an odd chain fatty acid, or a salt or derivative thereof, or a composition that includes a compound of an odd chain fatty acid, or a salt or derivative thereof, can be used (for example, administered or ingested) in combination with another agent or agents for treatment, prevention, maintenance, or prophylaxis of metabolic syndrome, diabetes, and the like, or for modulation of markers of metabolic syndrome. For example, a compound of an odd chain fatty acid disclosed herein can be used in combination with one or more agents selected from albiglutide, aleglitazar, balaglitazone, canagliflozin, CJ-30001 (CJ Cheiljedang Corporation), CJ-30002 (CJ Cheiljedang Corporation), Diamyd® (glutamic acid decarboxylase (rhGAD65)), dulaglutide, exendin 4, gemigliptin, lixisenatide, lobeglitazone, shengke I (Tibet Pharmaceuticals), SK-0403 (Sanwa Kagaku Kenkyusho), teneligliptin, teplizumab, tofogliflozin, acarbose, alogliptin benzoate, chlorpropamide, Diab II (Biotech Holdings), exenatide, glibenclamide, gliclazide, glimepiride, glipizide, gliquidone, glisentide, glisolamide, HL-002 (HanAll Biopharma), insulin (human), insulin, insulin analogue (Eli Lilly®), insulin aspart, insulin detemir, insulin glargine, insulin lispro, Janumet®, linagliptin, liraglutide, metformin, miglitol, mitiglinide, nateglinide, Novo Mix 30® (Novo Nordisk®) pioglitazone, pramlintide, repaglinide, rosiglitazone maleate, saxagliptin, sitagliptin, Tresiba, tolazamide, tolbutamide, vildagliptin, voglibose, bezafibrate, diflunisal, cinnamic acid, carbutamide, glyburide (glibenclamide), glibomuride, glyhexamide, phenbutamide, and tolcyclamide or with one or more agents selected from a class of agents, where the classes include sulfonylureas, non-sulfonylurea secretagogues, glucagon-like peptides, exendin-4 polypeptides, beta 3 adrenoceptor agonists, PPAR agonists, dipeptidyl peptidase IV inhibitors, biguanides, alpha-glucosidase inhibitors, immunomodulators, statins and statin-containing combinations, angiotensin converting enzyme inhibitors, adeno sine A1 receptor agonists, adenosine A2 receptor agonists, aldosterone antagonists, alpha 1 adrenoceptor antagonists, alpha 2 adrenoceptor agonists, alpha 2 adrenoceptor agonists, angiotensin receptor antagonists, antioxidants, ATPase inhibitors, atrial peptide agonists, beta adrenoceptor antagonists, calcium channel agonists, calcium channel antagonists, diguanides, diuretics, dopamine D1 receptor agonists, endopeptidase inhibitors, endothelin receptor antagonists, guanylate cyclase stimulants, phosphodiderivativease V inhibitors, protein kinase inhibitors, Cdc2 kinase inhibitors, renin inhibitors, thromboxane synthase inhibitors, vasopeptidase inhibitors, vasopressin Iantagonists, vasopressm 2 antagonists, angiogenesis inhibitors, advanced glycation end product inhibitors, bile acid binding agents, bile acid transport inhibitors, bone formation stimulants, apolipoprotein A1 agonists, DNA topoisomerase inhibitors, cholesterol absorption inhibitors, cholesterol antagonists, cholderivativeyl derivative transfer protein antagonists, cytokine synthesis inhibitors, DNA polymerase inhibitors, dopamine D2 receptor agonists, endothelin receptor antagonists, growth hormone antagonists, insulin sensitizers, lipase inhibitors, lipid peroxidation inhibitors, lipo-protein A antagonists, microsomal transport protein inhibitors, microsomal triglyceride transfer protein inhibitors, nitric oxide synthase inhibitors, oxidizing agents, phospholipase A2 inhibitors, radical formation agonists, platelet aggregation antagonists, prostaglandin synthase stimulants, reverse cholesterol transport activators, rho kinase inhibitors, selective estrogen receptor modulators, squalene epoxidase inhibitors, squalene synthase inhibitors, thromboxane A2 antagonists, amylin agonists, cannabinoid receptor antagonists, cholecystokinin A agonists, corticotropin-releasing factor agonists, dopamine uptake inhibitors, G protein-coupled receptor modulators, glutamate antagonists, glucagon-like peptide-1 agonists lipase inhibitors, melanin-concentrating hormone receptor antagonists, nerve growth factor agonists, neuropeptide Y agonists, neuropeptide Y antagonists, SNRIs, protein tyrosine phosphatase inhibitors, serotonin 2C receptor agonists, or with other agents such as central nervous system agents that affect neurotransmitters or neural ion channels, including antidepressants (bupropion), noradrenalin reuptake inhibitors (GW320659), selective serotonin 2c receptor agonists, selective 5HT 2c receptor agonists, antiseizure agents (topiramate, zonisamide), dopamine antagonists, cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocame and amphetamine regulated transcript promoters, a-melanocyte-stimulating hormone analogues, melanocoritin-4 receptor agonists, and agents that affect insulin metabolism/activity, which include protein-tyrosine phosphatase-IB inhibitors, peroxisome proliferator activated receptor-.gamma. receptor antagonists, short-acting bromocriptine (ergoset), somatostatin agonists (octreotide), and adiponectin/Acrp30 (Famoxin or Fatty Acid Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, dipeptidyl peptidase IV inhibitors), and those that decrease ghrelin activity, as well as amylin analogues (pramlintide); agents that may increase resting metabolic rate (selective β-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type I activity, corticotropin-releasing hormone agonists, inhibitors of fatty acid synthesis (cerulenin and C75), carboxypeptidase inhibitors, indanone/indanols, aminosterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion; or with one or more agents selected from ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1 426); N-5984; ISIS-1 13715; solabegron; SR-1 47778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-I 02677; tagatose; SLV-3

I 9; I 954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D I D2 agonists; melanocortin modulators; verongamme; neuropeptide Y antagonists; melanin-concentrating hormone receptor antagonists; dual PPAR alpha/gamma agonists; CGEN-P-4; kinase inhibitors; human MCH receptor antagonists; GHS-R antagonists; ghrelin receptor agonists; DG70 inhibitors; cotinine; CRF-BP inhibitors; urocortin agonists; UCL-2000; impentamine; f3-3 adrenergic receptor; pentapeptide MC4 agonists; trodusquemine; GT-20 16; C-75; CPOP; MCH-1 receptor antagonists; RED-1 03004; aminosterols; orexin-1 antagonists; neuropeptide Y5 receptor antagonists; DRF-4158; PT-15; PTPase inhibitors; A372 I 5; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPYSRA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR 1 antagonists; Acetyl-CoA carboxylase inhibitors; R-1496; HOB 1 modulators; NOX-B11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 agonists; stearoyl-CoA desaturase modulators; PPAR pan agonists; EP-01492; hormone-sensitive lipase inhibitors; fatty acid-binding protein 4 inhibitors; thiolactone derivatives; protein tyrosine phosphatase IB inhibitors; MCH-1 antagonist; P-64; PPAR gamma ligands; melanin concentrating hormone antagonists; thiazole gastroprokinetics; PA-452; T-226296; A-331440; immunodrug vaccines; diabetes % besity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; G1YIAD-1/GMAD-2; STG-a-MD; angiogenesis inhibitors; G protein-coupled receptor agonists; nicotinic therapeutics (ChemGenex); anti-obesity agents (Abbott); melanin concentrating hormone; GW-594884A; MC-4R agonist; histamine 113 antagonists; orphan GPCR modulators; MITO-3108; NLC-002; HE-2300; IGF/BBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; beta-3 adrenoceptor agonists; ob gene products (Eli Lilly & Co.); SWR-0342-SA; SWR-0335; SP-18904; oral insulin mimetics; obesity therapeutics (7TM Pharma); beta-hydroxysteroid dehydrogenase (HSD) inhibitors; QRX-431; E-6776; RI-450; melanocortin-4 antagonists; melanocortin 4 receptor agonists; obesity therapeutics (CuraGen); leptin mimetics; A-74498; second-generation leptin; NBI-103; CL-314698; CP-114271; beta-3 adrenoceptor agonists; NMI-8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (S)-sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; PY-1 antagonists; A-71378; .RTM.-didesmethylsibutramine; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BDBP-3226; HP— 228; talibegron; FR-165914; AZM-008; AZM-016; AZM-120; AZM-090; AZM-131; AZM-132; AZM-134; AZM-127; AZM-083; AZM-115; AZM-140; vomeropherin; BMS-187257; D-3800; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; exopipam; SSR— 125180; obesity therapeutics (Melacure Therapeutics AB); BRL-35135; SR— 146131; P-57; CGP-71583A; RF-1051; BMS-196085; manifaxine; DMNJ (Korea Research Institute of Bioscience and Biotechnology); BVT-5182; LY-255582; SNX-024; galanin antagonists; neurokinin-3 antagonists; dexfentluramine; mazindol; diethylpropion; phendimetrazine; benzphetamine; amfebutmone; sertraline; AOD-9604; ATL-062; BVT-933; GT389-255; SLV319; HE-2500; PEG-axokine; L-796568; and ABT-239; rimonabant, sibutramine, orlistat, PYY or an analog thereof, CB-1 antagonist, leptin, phentermine, and exendin analogs; GPR 1 19 agonists (e.g., anandamide; AR-231, 453; MBX-2982; Oleoylethanolamide; PSN-365,963; PSN-632,408; palmitoylethanolamide); GPR120 agonists; GPR 40 agonists; SGLT2 inhibitors.

Dosing

As will be readily apparent to one skilled in the art, the useful in vivo dosage to be administered and the particular mode of administration will vary depending upon the age, weight, the severity of the condition, and mammalian species treated, the particular forms of the compounds employed, and the specific use for which these compounds are employed. The determination of effective dosage levels, that is the dosage levels necessary to achieve the desired result, can be accomplished by one skilled in the art using routine methods, for example, in vivo studies. Reference may be made to, for example, "Estimating the Maximum Safe Starting Dose in Initial Clinical Trials for Therapeutics in Adult Healthy Volunteers," U.S. Food and Drug Administration, July 2005.

In some embodiments, a method provided herein may comprise administering a therapeutically effective amount of a composition provided herein. In some embodiments, a therapeutically effective amount may be determined by reference to the modulation of a marker of metabolic syndrome. In some embodiments, a therapeutically effective amount may be determined by reference to the modulation of a symptom of metabolic syndrome. In still other embodiments, reference may be made to established guidelines for the conditions described herein, including, but not limited to, guidelines for the treatment of diabetes.

The dosage may vary broadly, depending upon the desired effects and the therapeutic indication, such as marker values. Alternatively, dosages may be based and calculated upon the surface area or weight of the patient, as understood by those of skill in the art. The exact dosage will be determined on a case-by-case basis, or, in some cases, will be left to the informed discretion of the subject. The daily dosage regimen for an adult human patient may be, for example, an oral dose of an odd chain fatty acid, or a salt or derivative thereof, or a mixture of a plurality of odd chain fatty acids, or a salt or derivative thereof, from about 0.01 mg to about 10000 mg, from about 1 mg to about 5000 mg, from about 5 mg to about 2000 mg, from about 10 mg to about 1000 mg, or from about 50 mg to about 500 mg. A single dose may include an odd chain fatty acid, or a salt or derivative thereof, in about 0.01 mg, about 0.1 mg, about 1 mg, about 5 mg, about 10 mg, about 20 mg, about 50 mg, about 100 mg, about 200 mg, about 300 mg, about 400 mg, about 500 mg, about 600 mg, about 800 mg, about 900 mg, about 1000 mg, about 2000 mg, about 5000 mg, or more. The dosage may be adjusted according to the body mass of the subject, for example, the dosage may be about 0.001 mg/kg, about 0.01 mg/kg, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, or higher. The dosage may be a single one or a series of two or more given in the course of one or more days, as is appropriate for the individual subject. In some embodiments, the compounds will be administered for a period of continuous therapy, for example for about a week or more (e.g., one week, two weeks, three weeks, four weeks, five weeks, six weeks, seven weeks, eight weeks, or more), for several weeks, for about a month or more (e.g., one month, two months, three months, four months, five months, six months, seven months, eight months, mne months, ten months, eleven months, twelve months, or more), for about a year or more, or for a plurality of years. In some embodiments, an odd chain fatty acid, or a salt or derivative thereof, can be administered or ingested one time per day, two times per day, three times per day, or more.

As will be understood by those of skill in the art, in certain situations it may be necessary to administer the compounds disclosed herein in amounts that exceed the above-stated, preferred dosage range in order to effectively treat a subject.

Unit dosage forms can also be provided, e.g., individual packages with a premeasured amount of the composition, configured for administration on a predetermined schedule. Unit dosage forms configured for administration one to three times a day are preferred; however, in certain embodiments it may be desirable to configure the unit dosage form for administration more than three times a day, or less than one time per day.

Dosage amount and interval may be adjusted to the individual subject to provide plasma levels of the active moiety which are sufficient to maintain predetermined parameters, indicators, or marker values, or minimal effective concentration (MEC). Dosages necessary to achieve the desired result will depend on individual characteristics and route of administration. However, assays, for example, HPLC assays or bioassays, may be used to determine serum concentrations.

In some embodiments, the compounds and methods provided herein may be used in conjunction with devices and methods of using devices, for example, as provided in U.S. Pat. Nos. 7,651,845; 8,251,904; 8,251,904; 4,985,015; 8,827,957; 4,252,159; 5,318,521; 4,718,430; U.S. 2011/0190702; DE2615061; and in conjunction with diagnostic devices, for example, as provided in U.S. 2012/0072236.

Diagnosis and Monitoring

Provided herein are methods for the diagnosis and monitoring of metabolic syndrome and related conditions.

In some embodiments, the method of diagnosis or monitoring may comprise the step of measuring percentage of an odd chain fatty acid. In some embodiments, the method of diagnosis or monitoring may comprise the step of measuring a marker of metabolic syndrome. In some embodiments, a correlation between one marker and another may prove instructive. In some embodiments, metabolic syndrome or a related condition may be diagnosed by reference to a threshold level of a marker of metabolic syndrome, for example, serum odd chain fatty acid percentage, serum concentration of an odd chain fatty acid, or serum total odd chain fatty acid. For example, the threshold may be determined by reference to a symptom or marker of metabolic syndrome or a related condition, for example, diabetes.

The percentage of an odd chain fatty acid, or a marker of metabolic syndrome, in a subject may be monitored by any means. Samples for analysis may be derived any fluid or tissue of the subject. For example, from serum, plasma, erythrocyte membranes, urine, and feces.

Example 1: Dolphin Study

Dolphins at the Navy Marine Mammal Program (MMP) are a well-studied dolphin population with regard to metabolic syndrome, and this population has a higher risk of developing metabolic syndrome when compared to wild dolphins, such as wild dolphins living in Sarasota Bay, Fla., for example. When comparing the two populations, neither body mass indices nor stress indices (i.e., cortisol) are risk factors for metabolic syndrome in MMP dolphins. In studies comparing values of blood-based indicators of metabolic syndrome, MMP dolphins have been older than Sarasota Bay dolphins; older age of the MMP dolphin population is further supported by its higher annual survival rates and longer lives compared to wild dolphins, including those living in Sarasota Bay. Proposed risk factors for metabolic syndrome in dolphins can include advanced age, differences in feeding and activity schedules, and differences in dietary fish. It can be hypothesized that differences in dietary fish (and certain fatty acids associated with particular types of fish) can be responsible for differences in the risk of metabolic syndrome and iron overload in dolphins.

This study examined global metabolic profiles in six dolphins ("Group A dolphins"). The dolphins lived in netted enclosures within San Diego Bay. The dolphins started on a 100% capelin diet. Group A dolphins were fed one-third of their daily diet in the morning after their routine overnight fast and 2h postprandial, in-water, and trained blood samples were drawn (typically near 10:00 a.m.). An additional four dolphins ("Group C dolphins") were fed the capelin diet.

Capelin, the primary fish type fed to Group C dolphins, had no detectable C17:0 (<0.007 g/100 g). For other fish, C17:0 was measured as follows: croaker=39 mg/100 g, pinfish=41 mg/100 g, mullet=67 mg/100 g, herring=19 mg/100 g, and mackerel=22 mg/100 g. There was no detectable C 17:0 in squid.

The diets of the six Group A dolphins were from a capelin diet to transitioned to a diet consisting of 25, -0 capelin, 25% mullet, 25% croaker, and 25% pinfish, while maintaining the same kilocalories. Comparisons of daily fatty acid intake of the dolphins' original and modified diets are provided (Table 3), including demonstrated increased intake of C17:0 from a daily mean of 400 to 1,700 mg (greater than a four-fold increase).

Wild Sarasota Bay dolphins ("Group B dolphins") were analyzed as a reference group. While the timing of the most recent meal prior to each Group B dolphin's capture release was unknown, sonography was used to assess the presence or absence of stomach contents. Group B dolphins in the study had contents in their stomachs, supporting they were in a postprandial state. Following sample collection, Group B dolphins were released on site.

Two hour post-prandial samples were collected from the dolphins at baseline (week 0) and at four time points following the switch to the modified diet: 6, 12, 18, and 24 weeks. Routine monthly samples collected from four reference dolphins that were housed in the same environment as the Group A dolphins were assessed for glucose, triglycerides, ferritin, and percent serum fatty acids.

Changes in percent serum for the targeted fatty acids (C17:0, C20:4n6, and C22:0), as well as insulin, glucose, triglycerides, iron, transferrin saturation, and ferritin, were assessed among feeding study dolphins during weeks 3, 6, 12, 18 and 24 and compared to week 0 using pairwise comparison t-tests. Erythrocyte membrane fatty acids were measured during weeks 3, 6, 12, 18, and 24. Outcomes for markers of metabolic syndrome for Group A dolphins are provided in Table 4. Serum ferritin in Group A dolphins increased. Outcomes for markers of metabolic syndrome for the Group C dolphin group are provided in Table 5.

When a modified diet adding 25% pinfish and/or mullet was fed to six Group A dolphins over 24 weeks (increasing the average daily dietary C17:0 intake from 400 to 1700 mg), C17:0 serum levels increased, high ferritin decreased, and blood-based metabolic syndrome indices normalized toward reference levels. These effects were not found in Group C dolphins. Further, higher total serum C17:0 was an independent predictor of lower ferritin in dolphins in Group B dolphins.

Group A dolphins had a decrease in measures of spread (normalization) for triglycerides, glucose, and insulin that trended consistently from weeks 0 to 24. The standard deviation for glucose and triglycerides decreased from 23 to 6 mg/dl and 81 to 21 mg/dl, respectively. In comparison, Group C dolphins had an increase in standard deviation from weeks 0 to 24 (glucose increased from 12 to 14, and triglycerides increased from 20 to 98). The coefficient of variation (C.V.) from week 0 to week 24 for Group A dolphins decreased from 22% to 6% for glucose and 61% to 24% for triglycerides. When limiting to five study Group A dolphins (excluding the outlier sixth male dolphin that maintained high insulin possibly due to rut behavior and associated high testosterone throughout the study), the insulin standard deviation for dolphins on the modified diet decreased dramatically from 18 to 3 μIU/ml. When limiting to five study Group A dolphins (excluding the sixth dolphin that was experiencing rut behavior), the insulin C.V. decreased from 100% to 38%.

Serum ferritin levels decreased in all six Group A dolphins, with weeks 3 through 24 having lower levels than week 0. Total serum C17:0 (P=0.02) was associated with serum ferritin. Total serum C17:0 (R2=0.29, P=0.02) had an inverse relationship with ferritin. Stepwise regression, including age as a covariate, demonstrated that total serum C17:0 was an independent predictor of serum ferritin in dolphins (P=0.02) (Table 6). Indices of acute inflammation (ceruloplasmin and haptoglobin) were assessed. Despite decreases in ferritin, there were no differences in these two proteins during any of the study weeks compared to week 0, supporting that decreased ferritin was likely not due to changes in acute inflammation.

Fatty acids were compared between the two dolphin populations. Higher (n=30, Group A) and lower (n=19, Group B) mean insulin (11±12 and 2±5 μIU/ml, respectively; P<0.0001) and their dietary fish. In addition to higher insulin, triglycerides, and ferritin, Group A had lower percent serum heptadecanoic acid (C17:0) compared to Group B (0.3±0.1 and 1.3±0.4%, respectively; P<0.0001).

Group A dolphins also exhibited increased serum concentrations of other odd-chain fatty acids. Pelargonate, 10-undecenoate, nonadecanoate, arachidonate, adrenate, and docosapentaenoate were measured (Table 1).

Sample Collection and Transport

Blood was collected into BD Vacutainer serum separator tubes (for insulin, iron, ferritin, serum fatty acids profile, and serum chemistry), EDTA BD Vacutainer blood collection tubes (for erythrocyte fatty acid profile), and Lithium Heparin BD Vacutainer blood collection tubes (for plasma chemistry, including triglycerides). Blood tubes were centrifuged at 3000 rpm for 10 minutes within 30-60 minutes of collection and chilled during processing until shipment. Remaining serum/plasma was transferred to cryovials and stored at −80° C. until shipment on dry ice via overnight courier to the reference laboratories.

Sample Analysis

Serum and red blood cell membrane fatty acid profiles were performed by the Genetics Laboratories at the Kennedy Krieger Institute. Fatty acids were analyzed by capillary gas chromatography/mass spectrometry of pentaflourobenzyl bromide fatty acid derivatives using an AT-Silar-100 column (Grace, Columbia, Md. 21044) as previously described. For red blood cells only, the lipids were extracted with hexane:isopropanol before analysis. Each run was required to pass clinical laboratory quality control before the data were released. CV % were typically under 10%. Percent fatty acids in serum was used as a sturdier index to help reduce potential variability in serum among study dolphins. Iron, TIBC, and ferritin were analyzed at the Kansas State Veterinary Diagnostic Laboratory by colorimetric analysis on the Roche Cobas Mira (Roche Diagnostics, Indianapolis, Ind. 46250) per the manufacturer's protocol. Plasma triglycerides and glucose were directly measured using the Roche Cobas 8000 system (Roche Diagnostics, Indianapolis, Ind. 46250) per the manufacturers' protocol. Glucose was measured photometrically at the Animal Health Diagnostic Center at Cornell University on the Roche Diagnostics Modular Analytics P Module clinical chemistry analyzer (Roche Diagnostics, Indianapolis, Ind. 46250). Total insulin was analyzed at ARUP Laboratories by ultrafiltration/quantitative chemiluminescent immunoassay on the Siemens ADVIA Centaur Immunoassay system (Siemens Medical Solutions USA, Inc., Malvern, Pa. 19355).

Statistical analyses were conducted using World Programming System software (World Programming Ltd., Hampshire, United Kingdom). A general linear model was used to test for associations between insulin and 55 individual serum fatty acids. The 31 (56%) fatty acids that were associated with insulin were included in a multivariate, stepwise regression model to determine independent predictors of insulin. Among the six (11%) fatty acids that were independent predictors of insulin, a Wilcoxon rank-sum test was used to compare fatty acid levels between Group A and Group B dolphins; three (5%) of the six fatty acid had lower levels in Group A compared to Group B dolphins. To identify potentially low fish-based fatty acids that may be corrected through a modified diet, the term, 'targeted dietary fatty acids' for the remaining study was defined as fatty acids that were independent predictors of insulin and had significantly lower levels in Group A dolphins compared to Group B dolphins. Significance was defined as a P value less than 0.05.

Comparisons of glucose, triglycerides, iron, transferrin saturation, ferritin, and targeted percent serum fatty acids controlled for age by using an analysis of covariance with age as a covariate. Fish fatty acid profiles and iron measurements were performed by Covance Laboratories (Madison, Wis. 53703). Each of the following fish types was mixed with water and homogenized for uniformity: capelin from Canada and Iceland (*Mallotus villosus*), Atlantic croaker (*Micropogonias undulatus*), herring (*Clupea harengus*), mackerel (*Scomber japonicus*), pinfish (*Lagodon rhomboides*), squid (*Loligo opalescens*), and striped mullet (*Mugil cephalus*). The lipid was extracted, saponified with 0.5N methanolic sodium hydroxide, and methylated with 14% BF3-methanol. The resulting methyl derivatives of the fatty acids were extracted with heptane. An internal standard was added prior to the lipid extraction. The methyl derivatives of the fatty acids were analyzed by gas chromatography using external standards for quantitation.

Iron was measured by ICP Emission Spectrometry according to the Official Methods of Analysis of AOAC INTERNATIONAL, 18th Ed., Method 984.27 and 985.01, AOAC INTERNATIONAL, Gaithersburg, Md., USA, (2005). (Modified) (Covance, Madison, Wis. 53703).

Measurement of Serum Fatty Acids and Metabolites

Sample Accessioning: All samples were maintained at −80° C. until processed.

Sample Preparation: Samples were prepared using the automated MicroLab STAR® system from Hamilton Company. Several recovery standards were added prior to the first step in the extraction process for QC purposes. Proteins were precipitated with methanol under vigorous shaking for 2 min (Glen Mills GenoGrinder 2000) followed by centrifugation. The resulting extract was divided into five fractions: two for analysis by two separate reverse phase (RP)/UPLC-MS/MS methods with positive ion mode electrospray ionization (ESI), one for analysis by RP/UPLC-MS/MS with negative ion mode ESI, one for analysis by HILIC/UPLC-MS/MS with negative ion mode ESI, and one sample was reserved. Samples were placed briefly on a TurboVap® (Zymark) to remove the organic solvent. The sample extracts were stored overnight under nitrogen before preparation for analysis.

QA/AC: First, a pooled matrix sample generated by taking a small volume of each experimental sample (or alternatively, use of a well-characterized human plasma) served as a technical replicate throughout the data set; Second, extracted water samples served as process blanks; third, instrument variability was determined by calculating the median relative standard deviation (RSD) for the standards that were added to each sample prior to injection into the mass spectrometers; fourth, experimental samples were randomized across the platform run with QC samples spaced evenly among the injections.

Ultrahigh Performance Liquid Chromatography-Tandem Mass Spectroscopy (UPLC-MS/JVIS): Each of four methods utilized a Waters ACQUITY ultra-performance liquid chromatography (UPLC) and a Thermo Scientific Q-Exactive high resolution/accurate mass spectrometer interfaced with a heated electrospray ionization (HESI-II) source and Orbitrap mass analyzer operated at 35,000 mass resolution. A sample extract was dried, then reconstituted in solvents compatible to each of the four methods. Each reconstitution solvent contained a series of standards at fixed concentrations to ensure injection and chromatographic consistency. A first aliquot was analyzed using acidic positive ion conditions, chromatographically optimized for more hydrophilic compounds. In this method, the extract was gradient eluted from a C18 column (Waters UPLC BEH C18-2. 1×100 mm, 1.7 μm) using water and methanol, containing 0.05% perfluoropentanoic acid (PFPA) and 0.1% formic acid (FA). A second aliquot was also analyzed using acidic positive ion conditions, however it was chromatographically optimized for more hydrophobic compounds. In this method, the extract was gradient eluted from the same afore mentioned C18 column using methanol, acetonitrile, water, 0.05% PFPA and 0.01% FA and was operated at an overall higher organic content. A third aliquot was analyzed using basic negative ion optimized conditions using a separate dedicated C 18 column. The basic extracts were gradient eluted from the column using methanol and water, however with 6.5 mM Ammonium Bicarbonate at pH 8. A fourth aliquot was analyzed via negative ionization following elution from a HILIC column (Waters UPLC BEH Amide 2. 1×150 mm, 1.7 μm) using a gradient consisting of water and acetonitrile with 10 mM Ammonium Formate, pH 10.8. The MS analysis alternated between MS and data-dependent MSn scans using dynamic exclusion. The scan range varied slighted between methods but covered 70-1000 m/z.

Bioinformatics: The informatics system consisted of four major components, the Laboratory Information Management System (LIMS), the data extraction and peak-identification software, data processing tools for QC and compound identification, and a collection of information interpretation and visualization tools for use by data analysts. The hardware and software foundations for these informatics components were the LAN backbone, and a database server running Oracle 10.2.0.1 Enterprise Edition.

Data Extraction and Compound Identification: Raw data was extracted, peak-identified and QC processed using Metabolon's hardware and software. The systems were based on a web-service platform utilizing Microsoft's .NET technologies, which ran on high-performance application servers and fiber-channel storage arrays in clusters to provide active failover and load-balancing. Compounds were identified by comparison to library entries of purified standards or recurrent unknown entities. Biochemical identifications were based on three criteria: retention index within a narrow RI window of the proposed identification, accurate mass match to the library+/−10 ppm, and the MS/MS forward and reverse scores between the experimental data and authentic standards. The MS/MS scores were based on a comparison of the ions present in the experimental spectrum to the ions cataloged in a library. The use of three data points was utilized to distinguish and differentiate biochemicals.

Curation: Metabolon proprietary visualization and interpretation software was used to confirm the consistency of peak identification among the various samples. Library matches for each compound were checked for each sample and corrected if necessary.

Metabolite Quantification and Data Normalization: Peaks were quantified using area-under-the-curve. A data normalization step was performed to correct variation resulting from instrument inter-day tuning differences. Each compound was corrected in run-day blocks by registering the medians to equal one (1.00) and normalizing each data point proportionately (termed "block correction"). For studies that did not require more than one day of analysis, no normalization was used, other than for purposes of data visualization. Biochemical data was normalized to an additional factor (e.g., cell counts, total protein as determined by Bradford assay, osmolality, etc.) when necessary, to account for differences in metabolite levels due to differences in the amount of material present in each sample. Table 1 provides serum concentrations for various fatty acids in Group A dolphins at 6, 12, 18, and 24 weeks of the study of Example 1 proportional to values measured at the outset of the study.

TABLE 1

| Sub Pathway | Biochemical Name | 6 wk 0 wk | 12 wk 0 wk | 18 wk 0 wk | 24 wk 0 wk |
|---|---|---|---|---|---|
| Medium Chain Fatty Acid | caproate (6:0) | 0.98 | 1.01 | 0.92 | 0.76 |
| | heptanoate (7:0) | 1.42 | 1.02 | 1.23 | 1.21 |
| | caprylate (8:0) | 1.1 | 1.07 | 0.96 | 1.12 |
| | perlargonate (9:0) | 1.26 | 1.14 | 1.56 | 1.41 |
| | 10-undecenoate (11:1n1) | 1.41 | 1.54 | 1.22 | 1.75 |
| | 5-dodecenoate (12:ln7) | 1.49 | 1.67 | 1.08 | 1.11 |
| Long Chain Fatty Acid | myristate (14:0) | 0.8 | 0.87 | 0.74 | 0.58 |
| | myristoleate (14:ln5) | 1.45 | 1.55 | 0.97 | 1.02 |
| | pentadecanoate (15:0) | 1.01 | 1.27 | 1.42 | 0.97 |
| | palmitoleate (16:ln7) | 0.85 | 0.99 | 0.76 | 0.54 |
| | margarate (17:0) | 1.25 | 1.65 | 1.72 | 1.21 |
| | 10-heptadecenoate (17:ln7) | 1.12 | 1.38 | 1.35 | 0.87 |
| | nonadecanoate (19:0) | 1.22 | 1.65 | 1.79 | 1.28 |
| | 10-nonadecenoate (19:ln9) | 1.05 | 1.28 | 1.17 | 0.8 |
| | eicosenoate (20:1) | 0.72 | 0.81 | 0.72 | 0.43 |
| | erucate (22:ln9) | 0.71 | 0.81 | 0.68 | 0.45 |
| | nervonate (24:ln9)* | 0.71 | 1.41 | 0.74 | 0.62 |
| | oleate/vaccenate (18:1) | 0.98 | 1.04 | 0.84 | 0.64 |
| Polyunsaturated Fatty Acid | stearidonate (18:4n3) | 1.03 | 0.71 | 0.61 | 0.58 |
| | eicosapentaenoate (EPA; 20:5n3) | 0.88 | 0.99 | 0.88 | 0.57 |
| | docosapentaenoate (n3 DPA; 22:5n3) | 1.13 | 1.37 | 1.27 | 0.78 |
| | docosahexaenoate (DHA; 22:6n3) | 1.05 | 1.23 | 1.06 | 0.74 |
| | docosatrienoate (22:3n3) | 1.08 | 2.06 | 1.96 | 1.06 |
| | linoleate (18:2n6) | 0.87 | 0.93 | 0.76 | 0.66 |
| | linolenate [alpha or gamma; (18:3n3 or 6)] | 1.13 | 1.1 | 0.97 | 0.98 |
| | dihomo-linolenate (20:3n3 or n6) | 1.14 | 1.37 | 1.36 | 1.03 |
| | arachidonate (20:4n6) | 1.19 | 1.62 | 1.5 | 1.19 |
| | adrenate (22:4n6) | 1.51 | 2.17 | 2.82 | 1.73 |
| | docosapentaenoate (n6 DPA; 22:5n6) | 1.68 | 2.5 | 2.33 | 2.09 |
| | docosadienoate (22:2n6) | 0.85 | 1.08 | 0.99 | 0.54 |
| | dihomo-linoleate (20:2n6) | 0.9 | 1.12 | 1.03 | 0.73 |

Table 2 provides comparisons of demographics, metabolic health indicators, and targeted serum fatty acids between Group A dolphins and Group B dolphins of Example 1. The comparisons of metabolic variables and targeted serum fatty acids are controlled for age.

TABLE 2

| Demographic or blood-based Variable | Group A (n = 30) | Group B (n = 19) | P value |
|---|---|---|---|
| Age (years) | 26 ± 12 | 13 ± 9 | 0.002 |
| Sex (% females) | 15 (50%) | 12 (63%) | 0.37 |
| Metabolic variable | | | |
| Insulin (μIU/ml) | 11 ± 12 | 2 ± 5 | 0.04 |
| Serum glucose (mg/dl) | 104 ± 15 | 117 ± 10 | 0.02 |
| Triglycerides (mg/dl) | 149 ± 59 | 78 ± 26 | <0.0001 |
| Ferritin (ng/ml) | 3,878 ± 3,754 | 219 ± 184 | 0.005 |
| Iron (μg/dl) | 177 ± 57 | 109 ± 48 | 0.0003 |
| Transferrin saturation (%) | 56 ± 20 | 33 ± 11 | <0.0001 |
| Targeted serum Fatty acid | | | |
| Cl7:0 | 0.3 ± 0.1 | 1.3 ± 0.4 | <0.0001 |
| C20:4n6 | 4.1 ± 1.0 | 17.4 ± 2.3 | <0.0001 |
| C22:0 | 0.2 ± 0.04 | 0.7 ± 0.2 | <0.0001 |

Table 3 provides comparisons of dietary fatty acid (g) intake between original and modified diets for Group A dolphins of Example 1.

TABLE 3

| Fish-based nutrient | Original diet-total daily intake | Modified diet-total daily intake | P value |
|---|---|---|---|
| Targeted fatty acids (g) | | | |
| Heptadecanoic acid (C17:0) | 0.4 ± 0.2 | 1.7 ± 0.5 | 0.006 |
| Arachidonic acid (20:4n6) | 2 ± 1 | 5 ± 2 | 0.006 |
| Behenic acid (C22:0) | 0.2 ± 0.1 | 0.3 ± 0.3 | 0.43 |
| Other fatty acids (g) | | | |
| Myristic acid (C14:0) | 22 ± 6 | 18 ± 5 | 0.23 |
| Pentadecanoic acid (C15:0) | 1 ± 0.4 | 5 ± 4 | 0.007 |
| Palmitic acid (C16:0) | 62 ± 22 | 67 ± 22 | 0.71 |
| Stearic acid (C18:0) | 8 ± 3 | 12 ± 3 | 0.03 |
| Oleic acid (C18:1 n9) | 55 ± 25 | 50 ± 30 | 0.79 |
| Linoleic acid (C18:2) | 7 ± 2 | 6 ± 2 | 0.37 |
| Linolenic acid (C18:3) | 0.8 ± 0.5 | 1.5 ± 0.4 | 0.04 |
| Gamma-linolenic (C18:3n3) | 0.2 ± 0.1 | 0.6 ± 0.5 | 0.16 |
| Arachidic acid (C20:0) | 0.3 ± 0.2 | 0.7 ± 0.4 | 0.32 |
| Eicosadienoic acid (C20:2n6) | 0.3 ± 0.1 | 0.5 ± 0.2 | 0.14 |
| Eicosapentaenoic acid (20:5n3) | 40 ± 13 | 35 ± 11 | 0.43 |
| Erucic acid (C22:ln9) | 6 ± 1 | 3 ± 1 | 0.006 |
| Docosapentaenoic acid (C22:5n6) | 4 ± 1 | 6 ± 1 | 0.009 |
| Docosahexaenoic acid (C22:6n3) | 38 ± 10 | 42 ± 11 | 0.63 |
| Lignoceric acid (C23:0) | 0 | 0.2 ± 0.1 | 0.005 |
| Omega 3 fatty acids | 86 ± 25 | 89 ± 22 | 0.79 |
| Omega 6 fatty acids | 9 ± 3 | 12 ± 2 | 0.11 |
| Omega 6:3 fatty acids | 0.1 ± 0.01 | 0.1 ± 0.03 | 0.006 |
| Omega 9 fatty acids | 101 ± 33 | 72 ± 37 | 0.23 |
| Total cis-unsaturated fatty acids | 143 ± 99 | 207 ± 66 | 0.14 |
| Total trans-unsaturated fatty acids | 10 ± 3 | 8 ± 2 | 0.16 |
| Monosaturated fatty acids | 143 ± 46 | 111 ± 45 | 0.27 |
| Polyunsaturated fatty acids | 92 ± 27 | 96 ± 22 | 0.56 |

Table 4 provides blood based indicators of metabolic syndrome and fatty acid values for Group A dolphins of Example 1 during weeks 3, 6, 12, 18 and 24 compared to baseline week 0. Significant P values are provided.

TABLE 4

| Blood variable | Wild reference dolphins | Week 0 | Week 3 | Week 6 | Week 12 | Week 18 | Week 24 |
|---|---|---|---|---|---|---|---|
| Serum fatty acids (%) | | | | | | | |
| Heptadecanoic acid (C17:0) | 1.3 ± 0.4 | 0.3 ± 0.1 | 0.5 ± 0.2 | 0.5 ± 0.1 | 0.7 ± 0.3 | 0.8 ± 0.4 | 0.7 ± 0.2 |
| | | | $P = 0.007$ | $P = 0.001$ | $P = 0.03$ | $P = 0.03$ | $P = 0.007$ |
| Arachidonic acid (20:4n6) | 17 ± 2 | 4 ± 1 | 6 ± 2 | 7 ± 2 | 10 ± 4 | 10 ± 3 | 10 ± 3 |
| | | | $P = 0.005$ | $P = 0.001$ | $P = 0.01$ | $P = 0.005$ | $P = 0.004$ |
| Behenic acid (C22:0) | 0.7 ± 0.2 | 0.15 ± 0.04 | 0.21 ± 0.06 | 0.25 ± 0.07 | 0.28 ± 0.06 | 0.26 ± 0.04 | 0.29 ± 0.04 |
| | | | $P = 0.004$ | $P = 0.0008$ | $P = 0.003$ | $P = 0.002$ | $P < 0.0001$ |

| Blood variable | Wild reference dolphins | Week 0 | Week 3 | Week 6 | Week 12 | Week 18 | Week 24 |
|---|---|---|---|---|---|---|---|
| Metabolic health indicators | | | | | | | |
| Insulin (µIU/ml) | 2 ± 5 | 24 ± 21 | 17 ± 7 | 19 ± 23 | 22 ± 25 | 20 ± 21 | 16 ± 20 |
| Insulin (µIU/ml)[1] | 2 ± 5 | 19 ± 18 | 14 ± 5 | 10 ± 5 | 12 ± 9 | 11 ± 5 | 8 ± 2 |
| Plasma glucose (mg/dl) | 102 ± 15 | 109 ± 21 | 103 ± 13 | 110 ± 14 | 109 ± 17 | 97 ± 12 | 95 ± 6 |
| Triglycerides (mg/dl) | 78 ± 26 | 132 ± 81 | 166 ± 67 | 112 ± 37 | 119 ± 30 | 117 ± 45 | 97 ± 28 |
| Iron (µg/dl) | 109 ± 48 | 162 ± 64 | 153 ± 35 | 152 ± 52 | 160 ± 77 | 153 ± 31 | 177 ± 48 |
| Iron (µg/dl)[2] | 109 ± 48 | 132 ± 23 | 131 ± 4 | 127 ± 11 | 114 ± 38 | 136 ± 22 | 153 ± 29 |
| Ferritin (ng/ml) | 219 ± 184 | 3697 ± 6813 | 4235 ± 8198 | 2954 ± 5271 | 1160 ± 1905 | 1218 ± 1695 | 2201 ± 4656 |
| Ferritin (ng/ml)[2] | 219 ± 184 | 373 ± 52 | 341 ± 48 | 323 ± 52 | 263 ± 40 | 250 ± 67 | 243 ± 58 |
| | | | $P = 0.0009$ | | $P = 0.02$ | $P = 0.005$ | $P = 0.002$ |
| Transferrin saturation (%) | 33 ± 11 | 50 ± 25 | 49 ± 17 | 50 ± 26 | 52 ± 33 | 51 ± 19 | 60 ± 22 |
| Transferrin saturation (%)[2] | 33 ± 11 | 39 ± 5 | 40 ± 8 | 38 ± 8 | 31 ± 9 | 40 ± 7 | 49 ± 14 |
| Ceruloplasmin (mg/dl) | 18 ± 6[3] | 19 ± 5 | 18 ± 5 | 19 ± 4 | 23 ± 8 | 20 ± 5 | 19 ± 5 |
| Haptoglobin (mg/dl) | 17 ± 6[3] | 11 ± 3 | 12 ± 5 | 12 ± 3 | 14 ± 6 | 14 ± 6 | 9 ± 9 |

[1]Results when removing dolphin with high testosterone and breeding behavior during study.
[2]Two outlier high ferritin dolphins, which also had decreasing ferritin during the feeding study, were removed to enable comparisons of mean values during the study.
[3]Based upon previously reported results on wild, free-ranging dolphins in the Indian River Lagoon (Mazzara LM, et al. (2012) Iron indices among bottlenose dolphins (*Tursiops truncatus*): identifying populations at risk for iron overload. Comp Med 62:508-515. PMID: 23561885)

Table 5 provides targeted percent serum fatty acids and blood-based metabolic health indices in Group C dolphins (n=4) of Example 1, comparing values from weeks 12, 18 and 24 to baseline week 0. No values from weeks 12, 18, and 24 were significantly different than week 0.

TABLE 5

| Blood variable | Week 0 | Week 12 | Week 18 | Week 24 |
|---|---|---|---|---|
| Heptadecanoic acid (C17:0) | 0.30 ± 0.05 | 0.31 ± 0.07 | 0.29 ± 0.07 | 0.26 ± 0.04 |
| Arachidonic acid (20:4n6) | 5.2 ± 0.4 | 5.5 ± 0.8 | 6.0 ± 0.5 | 5.3 ± 0.7 |
| Behenic acid (C22:0) | 0.2 ± 0.02 | 0.2 ± 0.01 | 0.2 ± 0.04 | 0.2 ± 0.05 |
| Glucose (mg/dl) | 103 ± 12 | 102 ± 28 | 108 ± 33 | 99 ± 14 |
| Triglycerides (mg/dl) | 49 ± 20 | 57 ± 11 | 55 ± 15 | 91 ± 98 |
| Ferritin (ng/ml) | 503 ± 107 | 415 ± 93 | 384 ± 50 | 409 ± 47 |

Table 6 provides tested linear associations between C17:0 and C20:4n6 with ferritin in Group B dolphins (n=19) of Example 1 using a general linear model.

TABLE 6

| Fatty acid | Association with serum ferritin (P value) |
|---|---|
| Percent serum C17:0 | 0.22 |
| Total serum C17:0 | 0.02 |
| Percent RBC membrane C17:0 | 0.14 |
| Total RBC membrane C17:0 | 0.27 |
| Percent serum C20:4n6 | 0.09 |
| Total serum C20:4n6 | 0.03 |
| Percent RBC membrane C20:4n6 | 0.16 |
| Total RBC membrane C20:4n6 | 0.11 |

Analysis of FGF21, Ceramides, and Adiponectins

Aliquots of dolphin serum were shipped overnight on dry ice from the feeding study population of six bottlenose dolphins in the U.S. Navy Marine Mammal Program (MMP). Upon arrival, the samples were flash thawed in a 40° C. water bath for 2 minutes, vortexed for 10 seconds, and centrifuged at 3000×g for 10 seconds in tabletop centrifuge before being aliquoted into 110 µl and 50 µl aliquots which were then frozen at −80° C. until tested.

Reagents used were ACS grade or better. Water, acetonitrile, and methanol were LC-MS grade (Honeywell Burdick & Jackson, Morristown, N.J., USA). Synthetic stable isotope labeled peptides for adiponectin were previously described in detail by Neely et al. (2013) (Neely et al., 2013) and were synthesized by New England Peptide (Gardner, Mass., USA).

One microliter of diluted peptides (1:40; v/v, approximately 1 µg) was loaded onto the trap at 5 µl/min for 5 minutes before reverse phase separation at 350 nl/min from 0% to 40% mobile phase B [95% acetonitrile in 0.1% formic acid] over 50 minutes. Target proteotryptic peptides were identified by performing runs in positive ion information dependent acquisition mode with product ion scans for 50 ms with up to 20 product ion scans if precursors were 350-1250 m/z, exceeded 100 cps, and had a 2+ to 5+ charge state. Raw data files generated by the AB Sciex 5600 were converted to a peak list using the AB Sciex MS Data Converter (v. 1.3. beta, June 2012). Protein identifications were made using Mascot Daemon (v. 2.4.0) searching against the Ensembl (release 64) turTru 1 dolphin genome assembly protein database [16,599 sequences; Lindblad-Toh (2011)] and the common Repository of Adventitious proteins database (cRAP; 2012.01.01; the Global Proteome Nlachine) using the following parameters: trypsin was selected as the enzyme and two missed cleavages were allowed; carbamidomethylation (Cys) was specified as a fixed modification; Gln→pyro-Glu (N-term Q) and Oxidation (M) were specified as variable modifications; a peptide tolerance of 20 ppm and MS/MS tolerance of 0.1 Da; instrument type was set to ESI-QUAD-TOF. Mascot files were then uploaded into Scaffold Q+ (v.4.4.5) for analysis with a protein threshold set to 1.0% false discovery rate (FDR), a minimum number of peptides set to 3, and a peptide threshold set to 50%. Proteins were excluded from analysis that did not have a spectral count greater than 10 in at least one time point, or were missing more than 2 values at a time point. The quantitative value was normalized to total TIC with a normalization value set to 0. Exported values into sigma plot 11.0 and log 10 transformed the data to help improve normality of the data.

Measurement of FGF2 1

Serum FGF21 concentrations were determined using the Fibroblast Growth Factor 21 Mouse/Rat ELISA kit (Biovendor, Asheville, N.C.). Samples were thawed on ice for one hour, vortexed, then diluted 1:4 in dilution buffer. Standards were prepared by reconstituting the dry FGF21 standard in 1 mL of dilution buffer to a final concentration of 2560 pg/mL FGF21. This standard solution was serially diluted 1:1 from 1280 to 20 pg/mL resulting in 7 standard solutions of: 1280, 640, 320, 160, 80, 40, and 20 pg/mL. Samples at time 0 from animal A, W, and LL were pooled in order to construct a standard reference material for estimation of batch variability. A volume of sample, standard, or standard reference material equal to 100 µl was aliquoted in triplicate into the wells of two 96 well plates precoated with FGF21 antibody. Both samples and standards were randomized in location on the two plates. Triplicate samples from a single animal were always located on the same plate. Each plate contained an independent series of standards and standard reference material. Plates were incubated at room temperature (20° C.) and shaken at 300 RPM for 1.6 hours. Plates were then washed three times with 35 µL of Wash Solution provided in the kit using a multichannel pipette. Prior to and between washes the plates were inverted and tapped dry on a paper towel. Biotin Labelled Antibody solution (100 µL) was added to each well. Plates were further incubated at room temperature (20° C.) and shaken at 300 RPM for 1 hour. Plates were washed again as described above. Streptavidin-HRP Conjugate solution (100 4) was then added to each well. Plates were incubated at room temperature (20° C.) and shaken at 300 RPM for 30 minutes and washed as described above. Substrate solution (100 µL) was added to each well. The plates were then covered with aluminum foil and incubated at room temperature (20° C.) for 20 minutes. Color development was stopped by adding 100 µL of Stop Solution to each well. Plates were read on the Spectramax 340PC (Molecular Devices, Sunnyvale, Calif.) at 450 nm with a reference wavelength of 630 nm within 5 minutes of Stop Solution administration. Reference wavelength absorbance was subtracted from readings at 450 nm in order to obtain a final absorbance reading. A standard curve was calculated by using a quadratic regression line between standard absorbance's and known concentrations. Lower limit of detection (LLOD) was determined by adding 3× the standard deviation of the blank to the mean of the blank. Lower limit of quantification (LLOQ) was determined by adding 10× the standard deviation of the blank to the mean of the blank. Batch corrections were not applied as the coefficient of variation for the mean of the standard reference material was 0.23%.

Measurement of Ceramides

Serum aliquots (110 µl) were submitted to the MUSC Lipidomics Core for ceramide and sphingosine determination following the established protocol of (Bielawski et al., 2006). Briefly, serum was diluted in serum free media and spiked with internal standard solutions to quantify the following: sphingosines (SPH), dihydro-sphingosines (dSPH), sphingosine-1-phosphates (SIP), dihydro-sphingosine-1-phosphates (dSlP), Ceramides (Cer 16:0, Cer 14:0, Cer 16:0, Cer 18:0, Cer 18:1, Cer 20:0, Cer 24:0, Cer 24:1, Cer 26:0, Cer 26:1), and dihydro-ceramide (Cer d 16:0). The ceramides quantified contained a d18:1 sphingoid backbone and the numbers refer to the number of carbons:number of double bonds in the N-linked fatty acid. Lipids were extracted using a solution of 30:10:60 isopropanol:water:ethyl acetate. Samples were vortexed, and centrifuged at 4000 rpm for 10 min. Supernatant was transferred to a new tube, formic acid was added, and the extraction process was repeated. Supernatants were then combined, evaporated and reconstituted in mobile phase A (1 mM ammonium formate in methanol containing 0.2% formic acid). This was vortexed and centrifuged for 5 min at 4000 rpm. The supernatant was then injected into the HPLC system. Samples were analyzed on a Triple Quadrupole Mass Spectrometer equipped with Electrospray Ion Source (Thermo Finnigan, PE Sciex) Concentrations were determined by external standard curve. Any sample that did not exceed the concentration of the blank by a factor of two was considered below limit of detection. Data are reported as pmol/ml.

Measurement of Adiponectin

The preparation of serum for analysis of adiponectin was performed following the established protocol of Neely et. al (2013) with the following modifications. An aliquot of dolphin serum was thawed at room temperature for 1 minute, vortexed for 5s, then diluted (1:10; v:v) in 50 mM ammonium bicarbonate (AmBic). A solution of dithiothreitol (dissolved in 25mN1AmBic) was mixed by pipet to a final concentration of 100 mM, then centrifuged briefly and incubated at 60° C. for 30 min. The reaction was allowed to cool for 5 min, then alkylated by the addition of iodoacetamide (dissolved in 50 mM AmBic) to a final concentration of 10 mM and incubated at 37° C. for 30 minutes. The reaction was diluted with 176.5 µl 50 mM AmBic before adding mass spectrometry grade trypsin gold at a 1:10 ratio of enzyme to protein. The reaction was incubated at 37° C. for 16 hours then stopped by the addition of 350 µl of 1% formic acid and incubated at room temperature for 30 minutes. The two isotopically labeled standards were added to each sample, completed to 1 ml with 0.1% formic acid, and then loaded the sample onto an acetonitrile conditioned Strata-X 33µ polymeric reverse phase solid phase extraction column (Phenomenex, Torrance, Calif., USA). The column was washed twice with 1 ml 0.1% formic acid. Peptides were eluted first with 1 ml of 15% acetonitrile 0.1% formic acid then in a separate tube with 1 ml 30% acetonitrile 0.1% formic acid. Eluted samples were frozen at −80° C. overnight then dried down under vacuum by speedvac. Each sample was resuspended in 100 μl MIPA (98% water, 2% acetonitrile, 0.1% formic acid), vortexed for 15 min, then centrifuged at 10,000×g for 5 minutes before being transferred to a new 1.5 ml microcentrifuge tube. Peptide concentration was estimated by Absorbance at 280 nm (average 14 μg/μl). Prior to injection, 5 μls of the sample was diluted into 195 μl of MPA, and then injected onto the trap column.

Peptides of total and Lys-75 unmodified adiponectin were quantified using previously published protocols from Neely et. al (2013) with the following modifications. Tryptic peptides (10 μl) were loaded onto a 100 μm×2 cm C18 (100 A with 5 μm particles) trap column (Acclaim PepMap® 100; Thermo Fisher Scientific) and separated on a 75 μm×15 cm C18 (100 A with 3 μm particles) analytical column (Acclaim PepMap100®; Thermo Fisher Scientific). Reverse phase separation occurred at 350 nl/min. on a 2D+ NanoLC Ultra system (Eksigent, Dublin, Calif., USA). The LC was connected via nanospray source to a Triple-TOP 5600 System (AB Sciex, Foster City, Calif., USA).

Dolphin sera were processed in randomized batches of 9. One serum in each batch was processed in triplicate to determine experimental variability, plus a standard reference material (SRNI) serum to correct between experimental batches, and an experimental blank consisting of phosphate buffered saline (PBS). The blank was processed identically to serums in each batch and digested with the same amount of trypsin as the SRM. For PRNI experiments, the instrument was set in positive ion mode and TOF-MS data were collected in a window of 450-1250 mls for 150 ms, followed by each parent ion MS/MS for 200 ms, from 100 to 1600 mis. Total dolphin adiponectin (IFY) was quantified by comparing the ratio between the native IFY y13$^{2+}$ product ion (586.9$^{3+}$−>749.83$^{2+}$ m/z) and the corresponding product ion from the SIS peptide (589.6$^{3+}$−>753.83$^{2+}$ m/z). The amount of Lys-75 unmodified (GDT) dolphin adiponectin was quantified by comparing the ratio between the native GDT y7+ product ion (716.34$^{2+}$−>715.37+ m/z) and the corresponding product ion from the standard peptide (721.34$^{2+}$−>725.37$^+$ mlz). The amount of % unmodified was calculated as (GDT/IFY)×100.

Changes in Serum Concentrations

Figure 5A:
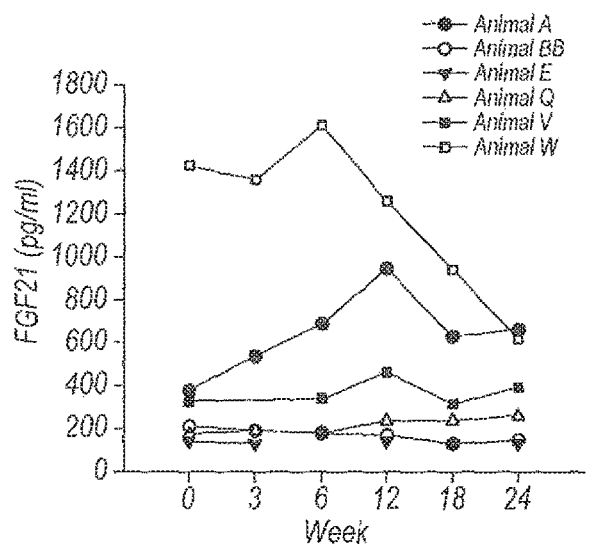
FIG. 5A provides data for serum concentrations of FGF21 in an embodiment according to Example 1; wherein symbols and lines correspond to the measured values of FGF21 (pg/ml) in each dolphin serum at the indicated collection time; and, FIG. 5B provides data for mean change in FGF21 (pg/ml) for the dolphin sera in FIG. 5A at each time point versus week 0.
Figure 5B:
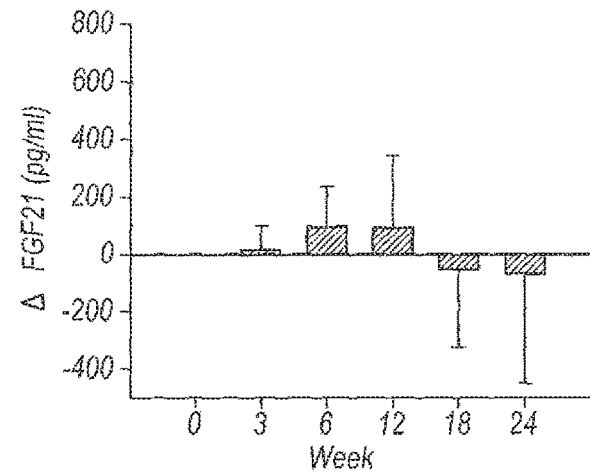
Figure 6A:
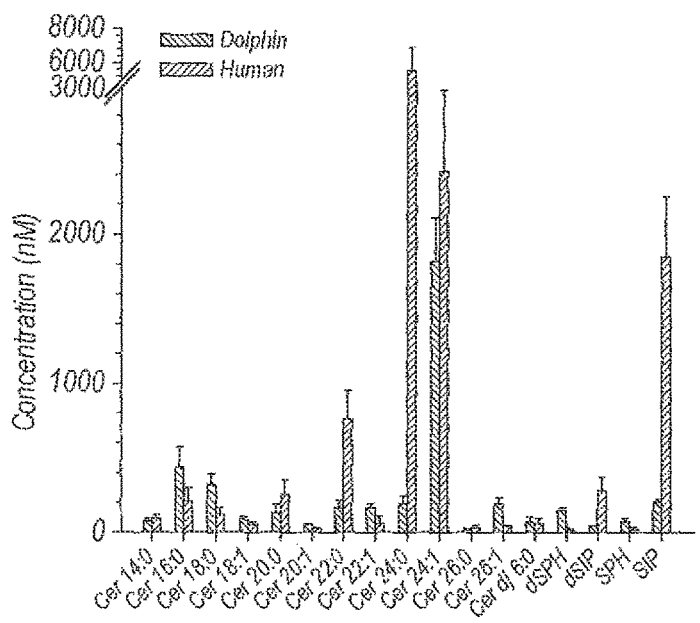
FIG. 6A provides data for serum proportions of ceramides and sphingosines in dolphins and humans sera at week 0 (n=6); and, FIG. 6B provides data for dolphin human sera (n=55) sphingosine and ceramide proportions, where human serum ceramide concentrations were extracted from Table 3 in (Argraves et al., 2011) representing a high HDL human group from the Copenhagen City Heart Study (CCHS) collection.
Figure 6B:
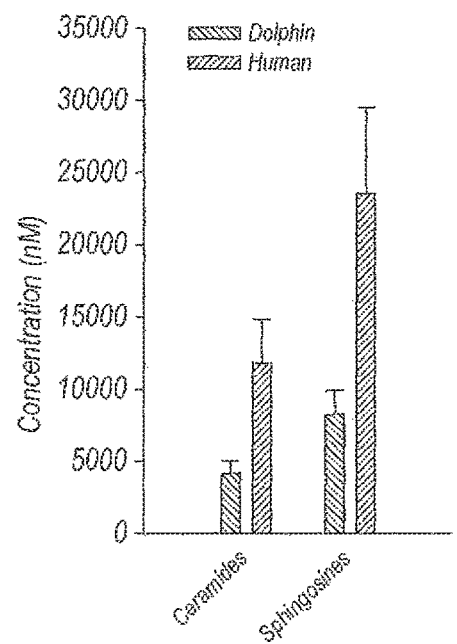
Figure 7A:
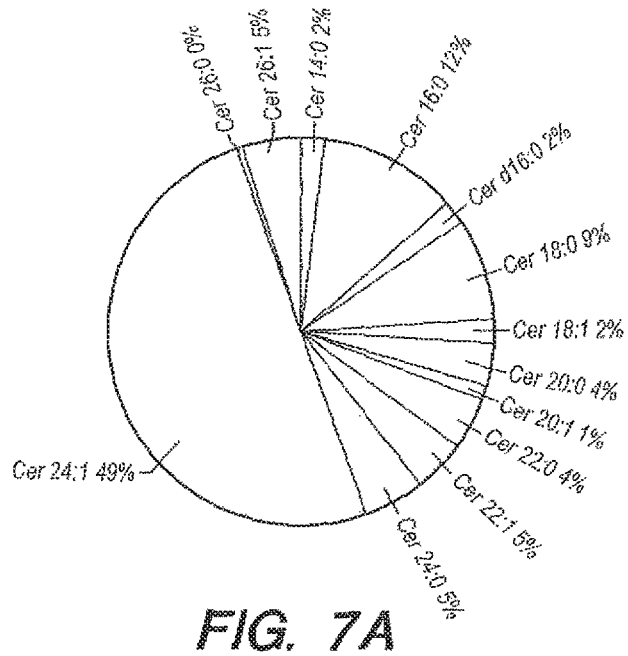
FIG. 7A provides data for dolphin serum ceramides in an embodiment according to Example 1; and, FIG. 7B provides data for human serum ceramides.
Figure 7B:
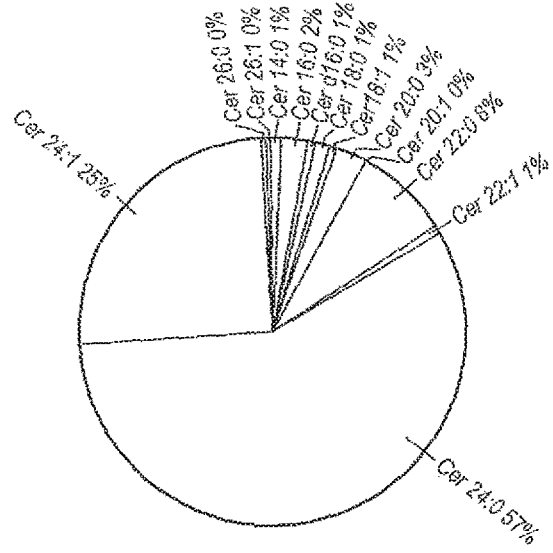
Figure 8:
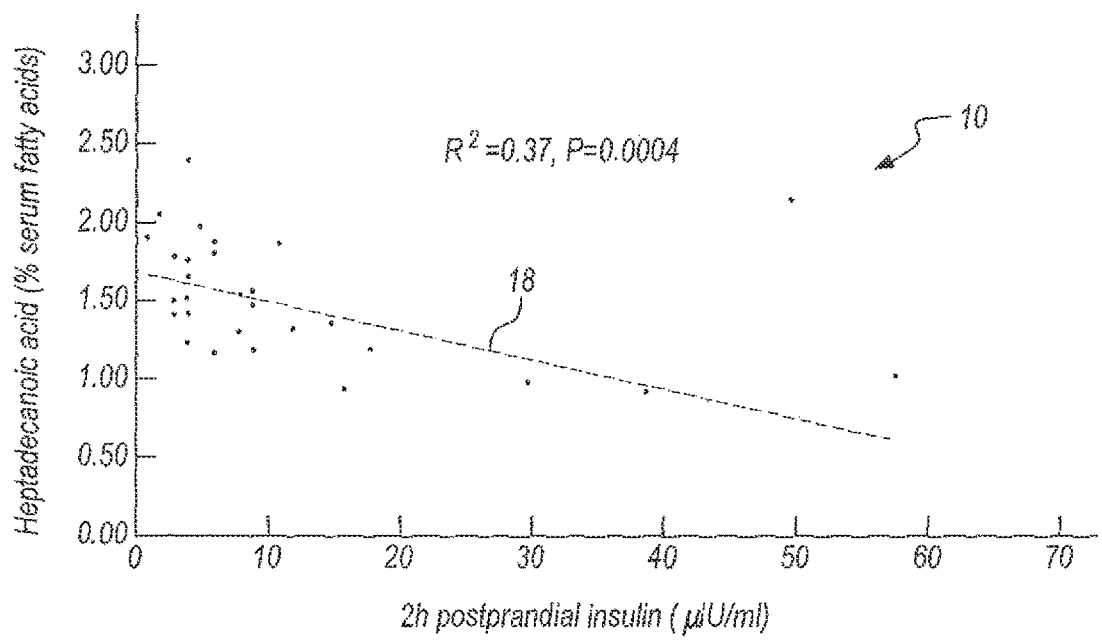
FIGS. 8-11 provide data for heptadecanoic acid (as % serum fatty acids) and insulin, glucose, triglycerides, and ferritin, respectively, using simple linear regression models in an embodiment according to Example 2.
Figure 9:
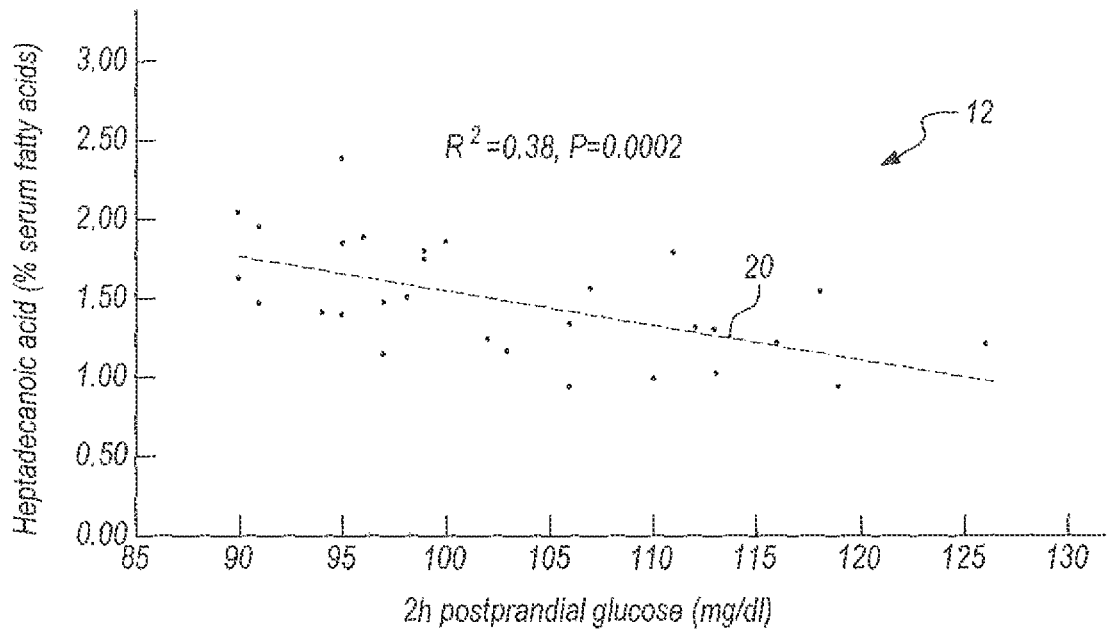
Figure 10:
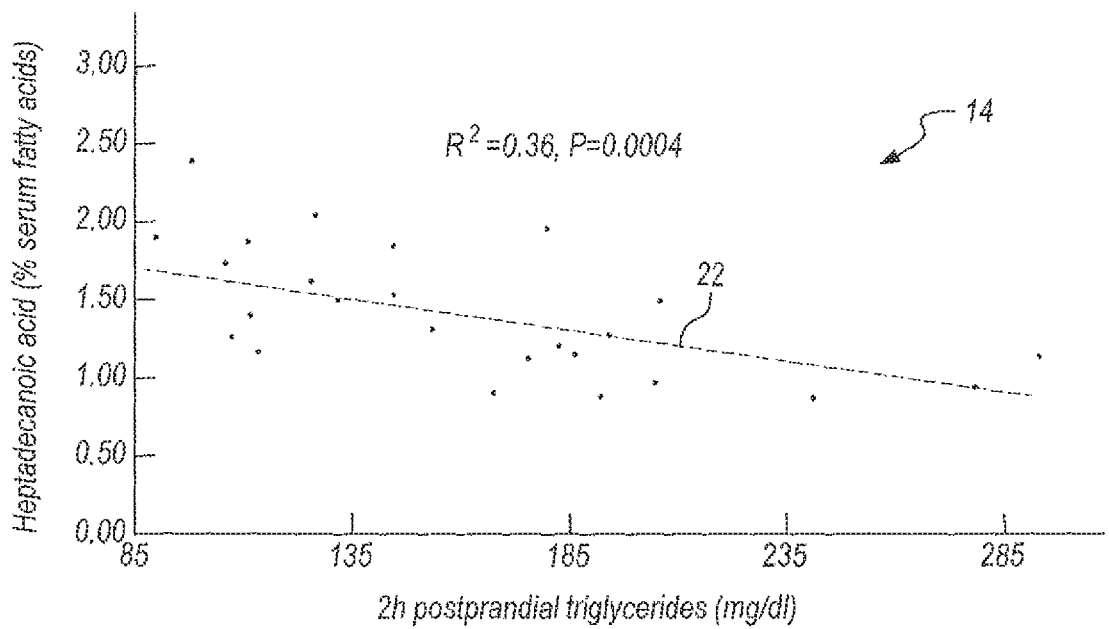
Figure 11:
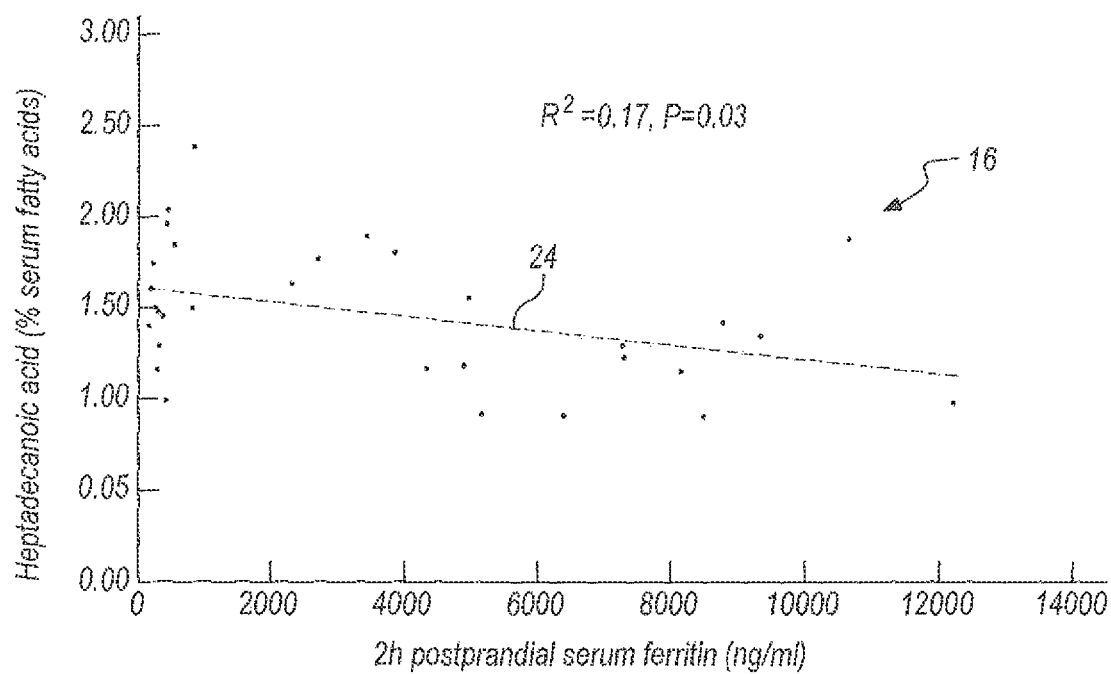

The levels of total and percent unmodified adiponectin in Group A dolphins was measured. The mean levels of adiponectin (pmol/mL SD) for the dolphins at 0-weeks was 776±401; 3-weeks, 937±531; 6-weeks, 806±382; 12-weeks, 1147±477; 18-weeks, 1189±640; and 24-weeks 1196±467. The change in serum adiponectin levels were significantly elevated in the dolphins at weeks 12, 18, and 24 (P<0.002) compared to week 0 (FIG. 1C). The mean levels of percent unmodified adiponectin (mean % unmodified±SD) in the dolphins at week 0 was 23.8±6; 3-weeks, I 8.9±6; 6-weeks, 18.4±6; 12-weeks, 18.0±4; 18-weeks, 16.0±4; 24-weeks, 15.2±5. The mean percent unmodified adiponectin was reduced (P<0.03) at all collection intervals versus control at week 0 (FIG. 1D). One dolphin contained serum FGF21 concentrations below the limit of quantification. In the other five dolphin samples serum FGF21 concentrations ranged from 129-1599 pg/ml. The mean change in FGF21 levels were not significantly different over the course of the study (FIG. 5).

Associations of Adiponectin with Metabolic Variables.

Serum adiponectin was positively associated with FGF21 (p=0.788, P<0.001) and heptadecanoic acid C 1 7:0 (p=0.441, P=0.008) and negatively associated with ferritin (p=−0.425, P=0.011), transferrin saturation (p=−0.381, P=0.024), and iron (p=−0.433, P=0.009) (Table 7). The amount of percent unmodified adiponectin was negatively correlated with total sphingosines (p=−0.434, P=0.009) and positively correlated with insulin (p=0.425, P=0.011) and ferritin (p=0.422, P=0.012) (Table 7). FGF21 was negatively correlated with iron (p=−0.430, P=0.013) (Table 7). Adiponectin and FGF21 were both negatively correlated with Cer 14:0, Cer 18:0, Cer 18:1, Cer 20:1, and Cer 22:1 (Table 7). No significant correlations were observed between the levels of serum adiponectin, percent unmodified adiponectin, or FGF21 with total ceramides, glucose, triglycerides, ceruloplasmin, and haptoglobin (Table 9).

Significant Changes in Ceramide Levels were Observed with a C 17:0-Rich Diet.

Serum ceramide levels were measured in Group A dolphins at each time interval (FIG. 3; Table 10). Ceramide 24:1 was the most abundant ceramide measured in the serum of the six dolphins comprising 40% on average of the total ceramides measured (Table 10). The levels of Cer 24:1 were significantly reduced, 18% at week 6, 24% at week 12, 33% at week 18, and 29% at week 24 compared to week 0 (FIG. 3E). Ceramide 18:1 comprises about 2% of the total ceramides measured and was reduced 18% at week 3, 21% at week 6, 24% at week 12, 39% at week 18, and 27% at week 24 compared to week 0 (FIG. 3A). Ceramide 20: 1 comprises approximately 1% of the total ceramides measured and was reduced 21% at week 3, 15% at week 6, 24% at week 12, 28% at week 18, and 31% at week 24 compared to week 0 (FIG. 3C). The Cer d 16:0 composed approximately 1% of the total ceramides and was significantly reduced approximately 46% at week 18 compared to week 0 (Table 10). Ceramide 22:0 comprised approximately 7% of total ceramides and was significantly increased 96% at week 3, 59% at week 6, 69% at week 12, 44% at week 18, and 50% at week 24 compared to week 0 (FIG. 3B). Ceramide 24:0 comprised roughly 11% of total ceramides and was significantly increased 183% at week 3, 98% at week 6, 129% at week 12, 66% at week 18, and 111%> at week 24 compared to week 0 (FIG. 3D). Ceramide 26:0 comprised approximately 1% of total ceramides and was significantly increased 143% at week 3, 85% at week 6, 149% at week 12, 71% at week 18, and 111% at week 24 compared to week 0 (FIG. 3F). No statistically significant change in serum levels of Cer 14:0, Cer 16:0, Cer 18:0, Cer 20:0, Cer 22:1, and Cer 26:1, which comprised roughly 3%, 14%, 9%, 3%, 4%, and 5% of total serum ceramides measured respectively, were observed compared to week 0 (Table 10).

Serum Sphingosine Levels Increased on a C17:0-Rich Diet.

Serum sphingosine levels were compared at each time point to week 0 (FIG. 4 Table 10). Dihydrosphingosine was significantly elevated by 32% at 6 weeks (180 pmol/ml±24), 34% at 18 weeks (186 pmol/ml±30), and 45% at 24 weeks (199 pmol/ml±43) compared to week 0 (140 pmol/ml±27). The levels of dSIP were significantly elevated by 157% at week 24 (88 pmol/ml 20) compared to week 0 (35 pmol/ml±5) (FIG. 4B). The most abundant sphingosine measured was SlP which comprised approximately 49% of the total sphingosines and was significantly elevated by 92% at week 24 (404 pmol/ml±59) compared to week 0 (211 pmol/ml±13) (FIG. 4C). The levels of total sphingosines (sum of sphingosines measured) were significantly increased by 21% at 6 weeks, 19% at 12 weeks, 24% at 18 weeks, and 62% at 24 weeks after the change in diet (FIG. 4D). Total ceramides means were numerically lower, but were not found statistically significant compared to time 0 (FIG. 4D). The change in serum levels of SPH which comprised roughly 12% of the total sphingosines was not statistically significant compared to week 0 (Table 10).

Significant Changes in Serum Proteins Identified by Mass Spectrometry

Mass spectrometry-based proteomics of undepleted serum led to the identification of 59 proteins with a false discovery rate less than 0.1%. Eight proteins were significantly different over the 24-week study relative to time 0 (Table 8). Corroborating the PRM/MS data, adiponectin was significantly elevated by 2.66, 2.79, and 2.99-fold at weeks 12, 18, and 24 compared to week 0, respectively (Table 8). Haptoglobin was elevated by 1.72-fold at week 12 and 1.55-fold at week 18, compared to week 0 (Table 8). Inter-alpha (globulin) inhibitor H3 displayed a 1.51-fold increase only at week 12 compared to week 0 (Table 8). Serpin peptidase inhibitor, Glade C-1 (Antithrombin III) was the only protein significantly reduced, but this reduction was transient and only reduced at week 6 (−1.50-fold change) at week 6 compared to week 0 (Table 8). Although ANOVA identified Hemoglobin subunit beta, hemoglobin subunit alpha, apolipoprotein E, and albumin as significantly different, post-hoc analysis did not indicate statistical differences at any time point compared to week 0 (Table 8).

Table 7 provides Pearson product moment correlations (p) of Adiponectin, % Unmodified Adiponectin, and FGF21 with ceramides and blood laboratory measurements for Example 1.

TABLE 7

| Measured Metabolic Variables | Adiponectin[†] (p) | P-value | % Unmodified Adiponectint (p) | P-value | FGF21[‡] (p) | P-value |
|---|---|---|---|---|---|---|
| Cer 14:0 | −0.375 | 0.026 | 0.018 | 0.921 | −0.457 | 0.008 |
| Cer d16:0 | −0.099 | 0.569 | 0.380 | 0.024 | −0.001 | 0.997 |
| Cer 18:0 | −0.456 | 0.006 | −0.439 | 0.008 | −0.412 | 0.017 |
| Cer 18:1 | −0.490 | 0.003 | 0.150 | 0.390 | −0.384 | 0.027 |
| Cer 20:0 | −0.276 | 0.108 | −0.495 | 0.002 | −0.179 | 0.319 |
| Cer 20:1 | −0.650 | <0.001 | −0.354 | 0.037 | −0.522 | 0.002 |
| Cer 22:1 | −0.615 | <0.001 | −0.029 | 0.867 | −0.482 | 0.005 |
| dSPH | −0.089 | 0.609 | −0.404 | 0.016 | −0.286 | 0.107 |
| S1P | 0.143 | 0.412 | −0.391 | 0.020 | −0.099 | 0.583 |
| Total Sphingosines | 0.075 | 0.669 | −0.434 | 0.009 | −0.23 | 0.198 |
| FGF21 | 0.788 | <0.001 | 0.202 | 0.261 | — | — |
| Venn-Watson et al. 2014 Values | | | | | | |
| Insulin | 0.120 | 0.493 | 0.425 | 0.010 | 0.072 | 0.692 |
| Iron | −0.433 | 0.009 | −0.053 | 0.763 | −0.430 | 0.013 |
| Transferrin saturation | −0.381 | 0.024 | −0.221 | 0.202 | −0.344 | 0.050 |
| Ferritin | −0.425 | 0.011 | 0.422 | 0.012 | −0.306 | 0.083 |
| (C1 7:0) | 0.441 | 0.008 | 0.778 | 0.657 | 0.218 | 0.223 |

[†]n = 35;
[‡]n = 33
Significance P < 0.05 are indicated in bold.

Table 8 shows fold change in quantitative spectral counts normalized to total TIC for proteins identified in the serum of Group A dolphins of Example 1.

TABLE 8

| Identified Proteins | Ensemble ID | RM-ANOVA (P < 0.05) | Fold Change from Week 0 | | | |
| | | | 0 vs 6 | 0 vs 12 | 0 vs 18 | 0 vs 24 |
|---|---|---|---|---|---|---|
| SERPINC1 (Antithrombin) | ENSTTRP-00000008123 | 0.033 | −1.50* | −1.07 | 1.08 | −1.22 |
| Hemoglobin Subunit Beta | ENSTTRP-00000016564 | 0.03 | −1.34 | 1.84 | 1.58 | 1.17 |
| Haptoglobin | ENSTTRP-00000001793 | 0.041 | 1.02 | 1.72* | 1.55* | 1.02 |
| Hemoglobin Subunit Alpha | ENSTTRP-00000011461 | 0.048 | −1.29 | 1.89 | 1.63 | 1.14 |
| Apolipoprotein E | ENSTTRP-00000008256 | 0.041 | −1.59 | 1.15 | 1.21 | 1.28 |
| Adiponectin | ENSTTRP-00000015964 | 0.001 | 1.93 | 2.66* | 2.79* | 2.99* |
| Albumin | ENSTTRP-00000006225 | 0.049 | 1.02 | −1.03 | −1.01 | 1.02 |
| Inter-Alpha (Globulin) Inhibitor H3 | ENSTTRP-00000002122 | | | | | |

*= P < 0.05 for indicates a significant fold change using Holm-Sidak Post-hoc test for multiple comparisons to control (week 0). Fold change was calculated using Non-transformed means Table 9 provides Pearson product moment correlations (p) of Adiponectin, % Unmodified Adiponectin, and FGF21 with ceramides and blood laboratory measurements for Group A dolphins of Example 1.

(30±7 and 25±14 years, respectively; P=0.32) or sex (percent female 37.5% and 54.6%, respectively; P=0.68). Similar to what has been previously reported with MMP dolphins, those with elevated insulin were also more likely to

TABLE 9

| Sphingolipids | Adiponectin[†] (o) | P-value | % Unmodified Adiponectin[†] (p) | P-value | FGF21[‡] (p) | P-value |
|---|---|---|---|---|---|---|
| Cer 16:0 | −0.221 | 0.202 | 0.024 | 0.892 | −0.260 | 0.144 |
| Cer 22:0 | −0.089 | 0.611 | −0.251 | 0.146 | −0.203 | 0.258 |
| Cer 24:0 | 0.092 | 0.598 | −0.192 | 0.269 | 0.002 | 0.993 |
| Cer 24:1 | −0.263 | 0.126 | 0.195 | 0.261 | −0.124 | 0.493 |
| Cer 26:0 | 0.053 | 0.763 | −0.150 | 0.389 | −0.059 | 0.746 |
| Cer 26:1 | −0.027 | 0.879 | 0.222 | 0.724 | 0.045 | 0.804 |
| Total Ceramides | −0.286 | 0.095 | −0.005 | 0.979 | −0.232 | 0.195 |
| dhS1P | 0.073 | 0.677 | −0.284 | 0.099 | −0.203 | 0.256 |
| SPH | −0.022 | 0.901 | −0.028 | 0.873 | −0.206 | 0.251 |
| Values from Venn-Watson et | | | | | | |
| Glucose | −0.059 | 0.735 | −0.103 | 0.557 | 0.053 | 0.768 |
| Triglycerides | −0.102 | 0.558 | 0.161 | 0.356 | −0.097 | 0.590 |
| Ceruloplasmin | −0.320 | 0.061 | −0.164 | 0.348 | −0.205 | 0.252 |
| Haptoglobin | 0.074 | 0.672 | −0.079 | 0.651 | −0.062 | 0.731 |

[†]n-35;
[‡]n-33

Table 10 provides a comprehensive list of Serum Ceramide and Sphingosine concentrations for Group A dolphins of Example 1, versus week 0.

have higher glucose, triglycerides, and gamma-glutamyl transpeptidase (GGT) when compared to MMP dolphins with non-elevated insulin, which can support the proposition

TABLE 10

| Serum Ceramides (pmols/ml ± SD) | Week 0 | Week 3 | Week 6 | Week 12 | Week 18 | Week 24 |
|---|---|---|---|---|---|---|
| Cer 14:0 | 76 ± 19 | 94 ± 34 | 85 ±20 | 102 ± 38 | 74 ± 25 | 81 ± 23 |
| Cer 16:0 | 435 ± 142 | 497 ± 112 | 562 ± 180 | 518 ± 151 | 454 ± 103 | 398 ± 105 |
| Cer d16:0 | 70 ± 25 | 72 ± 49 | 49 ± 18 | 55 ± 23 | 36 ± 16[†] | 46 ± 15 |
| Cer 18 | 316 ± 78 | 316 ± 100 | 351 ± 84 | 363 ± 125 | 315 ± 63 | 276 ± 52 |
| Cer 18:1 | 78 ± 17 | 60 ± 12[†] | 62 ± 12[†] | 58 ± 17[†] | 48 ± 14[‡] | |
| Cer 20:0 | 133 ± 50 | 113 ± 29 | 130 ± 38 | 126 ± 45 | 123 ± 38 | 106 ± 33 |
| Cer 20:1 | 40 ± 13 | 31 ± 10[†] | 33 ± 8* | 30 ± 11[†] | 28 ± 9[‡] | 27 ± 9[‡] |
| Cer 22:0 | 160 ± 50 | 259 ± 60[‡] | 237 ± 49[†] | 255 ± 60[‡] | 215 ± 43[‡] | 225 ± 42* |
| Cer 22:1 | 167 ± 23 | 168 ± 48 | 170 ± 38 | 157 ± 39 | 134 ± 23 | 129 ± 35 |
| Cer 24:0 | 187 ± 50 | 429 ± 171[‡] | 350 ± 66[‡] | 409 ± 121[‡] | 290 ± 62[†] | 378 ± 99[‡] |
| Cer 24:1 | 1826 ± 289 | 1567 ± 338 | 1485 ± 280 | 1383 ± 406* | 1223 ± 227[†] | 1287 ± 205[‡] |
| Cer 26:0 | 16 ± 5 | 33 ± 12[†] | 27 ± 3* | 36 ± 20[†] | 26 ± 11* | 31 ± 14* |
|  | 186 ± 44 | 213 ± 89 | 194 ± 76 | 194 ± 88 | 144 ± 43 | 171 ± 52 |
| Total Ceramides | 3688 ± 672 | 3852 ± 933 | 3734 ± 699 | 3685 ± 1016 | 3112 ± 558 | 3213 ± 522 |
| dSPH | 140 ± 27 | 143 ± 20 | 180 ± 24* | 149 ± 33 | 186 ± 30* | 199 ± 43[†] |
| dS1P | 35 ± 5 | 35 ± 9 | 46 ± 14 | 53 ± 16 | 47 ± 11 | 88 ± 20[‡] |
| SPH | 74 ± 22 | 60 ± 19 | 63 ± 25 | 77 ± 43 | 61 ± 34 | 56 ± 7 |
| S1P | 211 ± 13 | 196 ± 19 | 266 ± 54 | 271 ± 50 | 275 ± 46 | 404 ± 59[‡] |
| Total Sphingosines | 460 ± 39 | 434 ± 39 | 555 ± 86* | 549 ± 69* | 569 ± 64[†] | 747 ± 107[‡] |

Significance was determined by a repeated measures one-way ANOVA with a Holm-Sidak post-hoc test.
*= P < 0.05,
[†]= P < 0.01, and
[‡]= P < 0.001.

Example 2

Blood samples were taken from a managed population of thirty dolphins from the Navy Marine Mammal Program (MMP). 2h postprandial blood values from MMP dolphins with elevated insulin (Elevated insulin levels were defined as values greater than or equal to the 75th quartile among the 30 Group A dolphins (15 μIU/ml), n=8) were compared to MMP dolphins without elevated insulin (n=22). Table 11 illustrates values of elevated versus non-elevated insulin. There were no differences in groups with regard to age that dolphins with elevated insulin represent those with or at higher risk of metabolic syndrome.

TABLE 11

| Metabolic variable | Elevated insulin (n = 8) | Non-elevated insulin (n = 22) | P value |
|---|---|---|---|
| Metabolic panel | | | |
| Glucose (mg/dl) | 114 ± 7 | 100 ± 8 | 0.002 |
| Triglycerides (mg/dl) | 164 ± 205 | 128 ± 43 | 0.007 |

TABLE 11-continued

| Metabolic variable | Elevated insulin (n = 8) | Non-elevated insulin (n = 22) | P value |
|---|---|---|---|
| Gamma-glutamyl transpeptidase (U/l) | 33 ± 12 | 24 ± 10 | 0.046 |
| Iron (µg/dl) | 178 ± 39 | 177 ± 63 | 0.64 |
| Ferritin (ng/ml) | 5,931 ± 4,210 | 3,131 ± 3,371 | 0.13 |
| Transferrin saturation (%) | 53 ± 14 | 57 ± 21 | 1.0 |
| HbA1c (%) | 5.1 ± 0.2 | 5.2 ± 0.4 | 0.78 |
| Estimated average glucose (mg/dl) | 85 ± 7 | 86 ± 12 | 0.78 |
| Serum fatty acid (%) | | | |
| Heptadecanoic acid (C17:0) | 1.0 ± 0.2 | 1.6 ± 0.3 | 0.0008 |
| Oleic acid (C18:ln9) | 21 ± 2 | 18 ± 4 | 0.03 |
| Linoleic acid (C18:2n6) | 1.6 ± 0.1 | 1.3 ± 0.2 | 0.03 |
| Arachidonic acid (C20:4n6) | 3 ± 0.3 | 4 ± 1 | 0.004 |
| Eicosapentaenoic acid (C20:5n3) | 10 ± 1 | 13 ± 3 | 0.006 |
| Myristic acid (C14:0) | 1.7 ± 0.4 | 1.9 ± 0.6 | 0.39 |
| Palmitic acid (C16:0) | 14 ± 1 | 14 ± 2 | 0.25 |
| Palmitoleic acid (C16:ln7) | 6 ± 1 | 6 ± 1 | 0.17 |
| Stearic acid (C18:0) | 12 ± 2 | 11 ± 2 | 0.66 |
| Vaccenic acid (C18:1cis-ln7) | 6 ± 2 | 6 ± 1 | 0.73 |
| a-Linolenic acid (C18:3n3) | 0.2 ± 0.1 | 0.4 ± 0.7 | 0.28 |
| Erucic acid (C22:ln9) | 4.7 ± 1.7 | 4.6 ± 1.3 | 0.87 |
| Docosatrienoic acid (C22:3n3) | 0.1 ± 0.1 | 0.1 ± 0.1 | 0.47 |
| Docosapentaenoic acid (C22:5n3) | 1.9 ± 0.1 | 2.0 ± 0.3 | 0.98 |
| Docosahexaenoic acid (C22:6n3) | 9.2 ± 0.9 | 8.9 ± 1.2 | 0.34 |
| Tricosylic acid (C23:0) | 0.5 ± 0.1 | 0.5 ± 0.3 | 0.32 |
| Nervoic acid (C24: ln9) | 1.0 ± 0.5 | 0.9 ± 0.4 | 0.76 |

From the data of Table 11, it can be seen that dolphins with elevated insulin also had higher oleic acid and linoleic acid; and lower heptadecanoic acid, arachidonic acid, and EPA compared to non-elevated insulin dolphins. Thus, these five fatty acids, and margaric acid in particular, can be employed as indicators of metabolic syndrome. See, e.g., Venn-Watson S. et al. (2015) Increased dietary intake of saturated fatty acid heptadecanoic acid (C17:0) associated with decreasing ferritin and alleviated metabolic syndrome in dolphins. PLOS ONE 10:e0132117. The method by which the serum and red blood cell fatty acid profiles was determined is described in Lagerstedt et al. "Quantitative Determination of Plasma C8-C26 Total Fatty Acids for the Biochemical Diagnosis of Nutritional and Metabolic Disorders" Mol Gen Metabol 73:38-45. This method for determining heptadecanoic acid can be used to directly measure C17:0 (ug/ml) without having to measure all fatty acids (there are over fifty-five) and back calculating the percentage of C 17:0. As such, this method can be much quicker, much more direct, and, much more cost effective than other methods conventionally used to determine sera margaric acid levels.

FIGS. 8-11 are plots 10, 12, 14, and 16 of margaric acid (as a percentage of serum fatty acids in sera) versus 2h postprandial insulin (µIU/ml), glucose (mg/dl), triglycerides (mg/dl) and ferritin (ng/ml), respectively, for the 30 MMP dolphins cited above. For each of the respective plots 10, 12, 14 and 16 in FIGS. 8-11, respective linear regressions 18, 20, 22 and 24 of the data were accomplished.

The statistical analyses depicted in FIGS. 8-11 were conducted using the World Programming System (World Programming Ltd., Hampshire, United Kingdom). Age, sex, and blood values (glucose, HbA1c, estimated average blood glucose, triglycerides, GGT, iron, transferrin saturation, ferritin, and percent serum fatty acids) were compared between dolphins with and without elevated insulin. Sex distribution was compared using a Mantel-Haenzsel Chi-square test. Age and blood variable values were compared using a Wilcoxon rank-sum test. For the five fatty acids that had significant differences between dolphins with and without elevated insulin (heptadecanoic acid, oleic acid, linoleic acid, arachidonic acid (AA), and eicosapentaenoic acid (EPA)), simple linear and stepwise multivariate regressions were used to test for associations between these potential fatty acid predictors and dependent metabolic syndrome indices (insulin, glucose, triglycerides, and ferritin). In all analyses, significance was defined as a P value less than 0.05.

From FIGS. 8-11, and using the above criteria, it can be seen that among the 30 MMP dolphins, percent serum heptadecanoic acid had negative linear associations with insulin, glucose, triglycerides, and ferritin, respectively. Using the best fit, stepwise regression described above, it can be inferred from FIGS. 8-11 that heptadecanoic acid can be an independent predictor of insulin (FIG. 8, P=0.0004), glucose (FIG. 9, P=0.0002) triglyceride (FIG. 10, P=0.0004), and ferritin (FIG. 11, P<0.0001) levels.

From the data above, it can be appreciated that there is a linear relationship between levels of heptadecanoic acid and insulin, glucose, triglycerides and ferritin levels in sera for the MMP dolphins. To confirm this, the margaric acid levels of the sera in control population B (Sarasota Bay dolphins) were checked.

Figure 12:
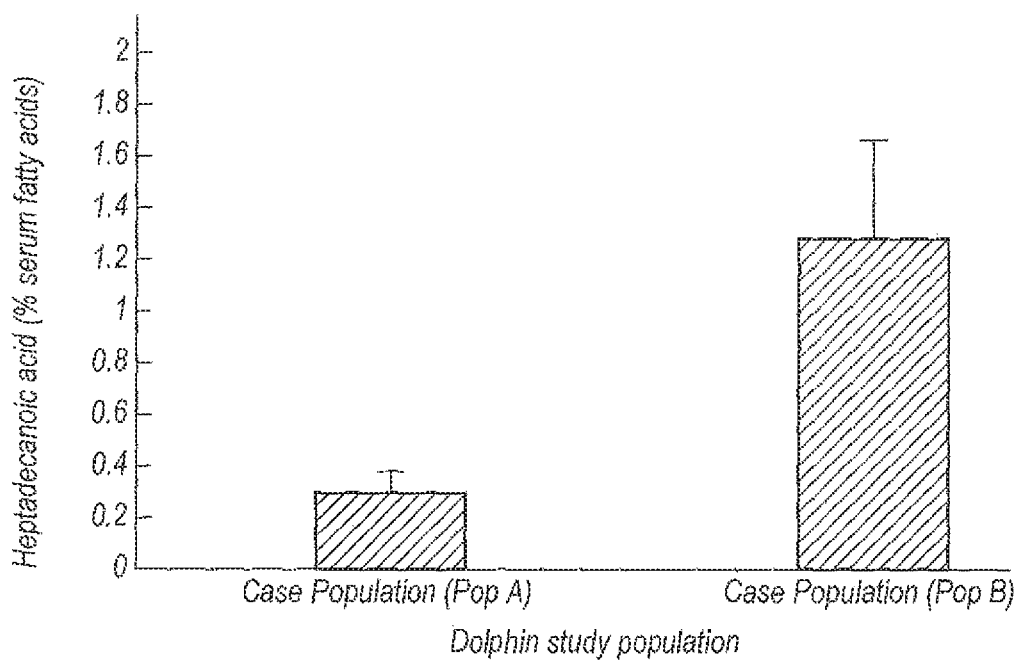
FIG. 12 provides data for sera heptadecanoic acid levels between a case study population of subjects that are highly susceptible to metabolic syndrome and a control study population with low susceptibility in an embodiment according to Example 2.

FIG. 12 illustrates the results of the above heptadecanoic acid check. From FIG. 12, it can be seen that the control population of Sarasota Bay dolphins had three times the level of heptadecanoic acid (measured as a percent serum fatty acid) than the case population A of MMP dolphins. Table 12 illustrates a comparison of the blood samples of the above-cited 30 MMP dolphin versus the sera of 19 wild dolphins in their natural habitat (Sarasota Bay dolphins). MMP dolphins were older than Sarasota Bay dolphins mean age±SD=25.6±12.2 and 12.7±9.0 years, respectively; P=0.002). As shown in Table 12, M1YIP dolphins had higher insulin, glucose, triglycerides, ferritin, iron, and transferrin saturation compared to Sarasota Bay dolphins. MMP dolphins had lower serum heptadecanoic acid when compared to Sarasota Bay dolphins. While red blood cell fatty acids were not collected on the initial group of 30 MMP dolphins, this measurement was included for Sarasota Bay dolphins to use as a reference during the subsequent feeding study with MMP dolphins, as described more fully below.

TABLE 12

| Blood-based variable | MMP (n = 30) | Sarasota Bay (n = 19) | P value |
|---|---|---|---|
| Metabolic variable | | | |
| Total insulin (µIU/ml) | 11 ± 12 | 2 ± 5 | <0.0001 |
| Glucose (mg/dl) | 117 ± 10 | 104 ± 15 | 0.005 |
| Triglycerides (mg/dl) | 148 ± 59 | 78 ± 26 | <0.0001 |
| Gamma-glutamyl transpeptidase (U/L) | 27 ± 11 | 20 ± 6 | 0.02 |
| Ferritin (ng/ml) | 3,878 ± 3,754 | 219 ± 184 | <0.0001 |
| Iron (µg/dl) | 177 ± 57 | 109 ± 48 | <0.0001 |
| Transferrin saturation (%) | 56 ± 20 | 33 ± 11 | <0.0001 |
| Targeted serum fatty acid (µg/ml) | | | |
| Heptadecanoic acid (C17:0) | 9 ± 2 | 25 ± 9 | <0.0001 |

From the Table 12 data, it can be seen that among Sarasota Bay dolphins, serum heptadecanoic acid (µg/ml) was inversely associated with ferritin ($R^2$=0.29 P=0.02). All Sarasota Bay dolphins with ferritin greater than 219 ng/ml (this population's 50th quartile) had serum heptadecanoic acid levels less than 25 µg/ml, suggesting that serum heptadecanoic acid lower than 25 µg/ml may result in an increased risk of hyperferritinemia.

Figure 13:
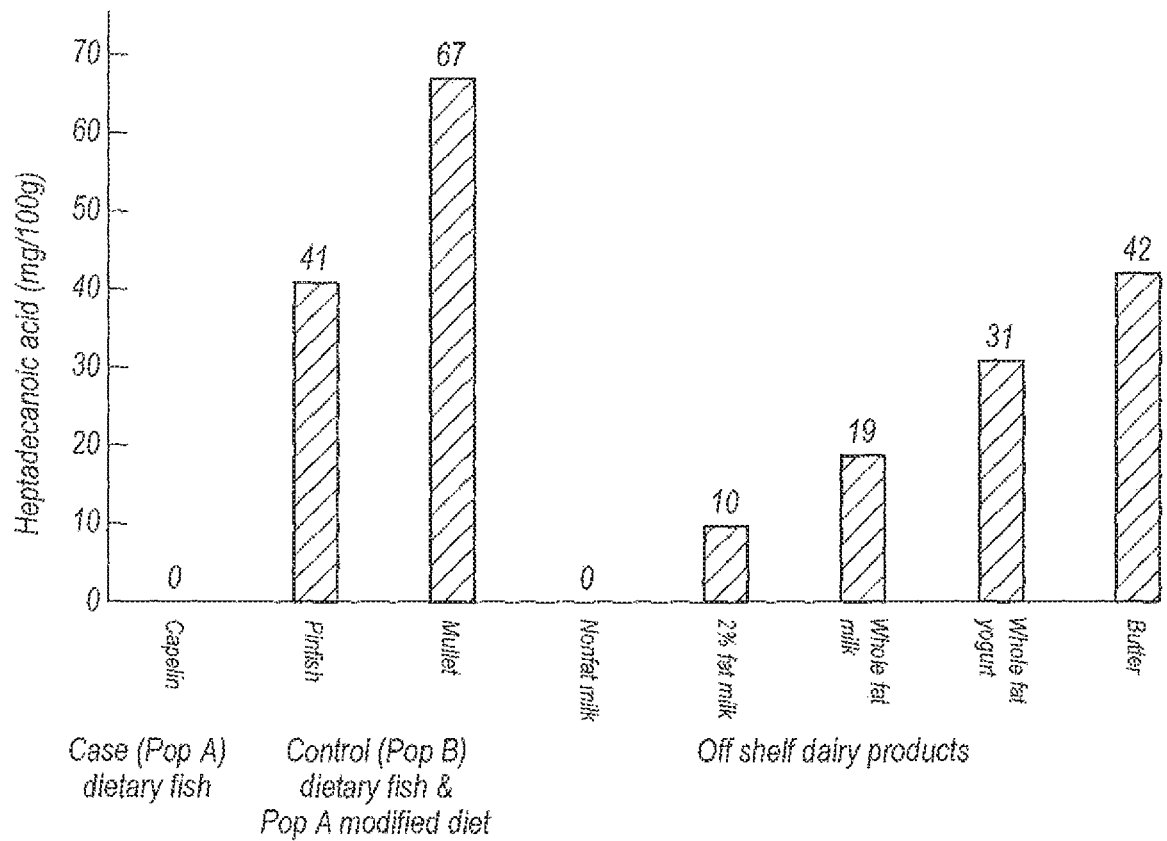
FIG. 13 provides data for the amount of heptadecanoic acid in a variety of fish types and dairy products in an embodiment according to Example 2.

With a renewed focus on heptadecanoic acid, and referring now to FIG. 13, comparisons of diets of MMP dolphins (Case Population A) with diets of Sarasota Bay dolphins (Control Population B) were accomplished to determine the levels of heptadecanoic acid in the food being eaten by the two populations. As shown in FIG. 13, capelin, and the primary fish type fed to MMP dolphins, had no detectable heptadecanoic acid compared to other fish types. With the exception of squid (not shown in FIG. 13), capelin also had the lowest levels of iron compared to the other fish types. As shown in FIG. 13, mullet, and pinfish (which are representative of fish eaten by Sarasota Bay dolphins), had relatively high levels of heptadecanoic acid. Mullet and pinfish also had the highest iron levels among the fish tested. Due to the known presence of heptadecanoic acid in dairy products, heptadecanoic acid levels were measured in off-the-shelf dairy products. Dairy products consumed by human are also shown in FIG. 13, for comparison. The content of heptadecanoic acid (mg/100 g), from highest to lowest, was 42 (butter), 31 (whole fat yogurt), 19 (whole fat milk), and 10 (2% fat milk). Heptadecanoic acid was not detected in either nonfat milk <2 mg/100 g or nonfat yogurt <10 mg/100 g.

From the above data, it can be seen that there is a linear relationship between heptadecanoic acid and triglycerides, glucose, insulin and ferritin in sera, which has been confirmed with measurements of both heptadecanoic acid in dolphins for both a case population and a control population, as well as a measure of heptadecanoic acid in the diets eaten by the respective populations.

Figure 14:
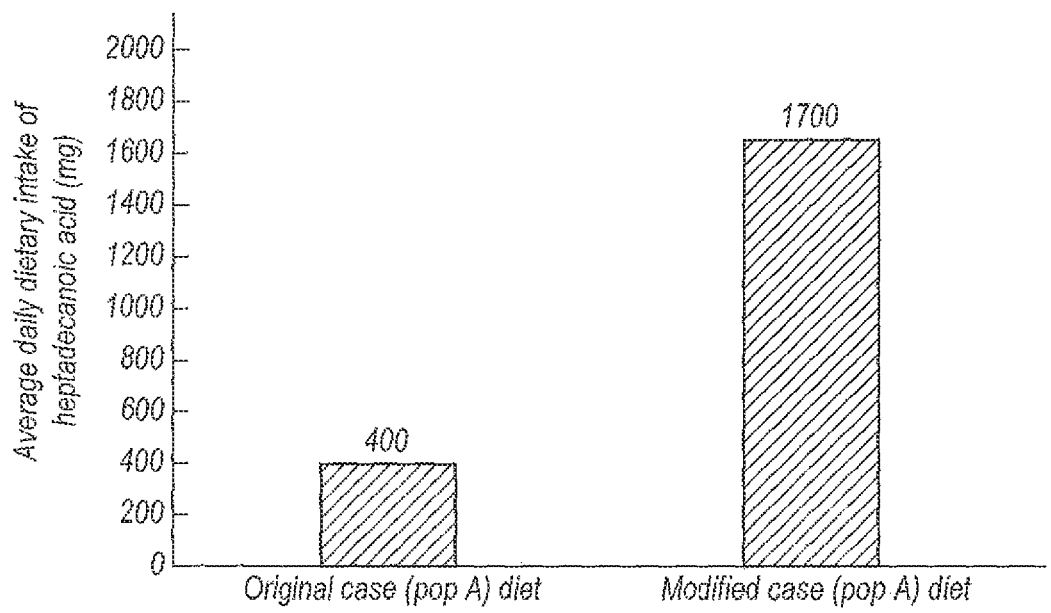
FIG. 14 provides data for the comparison of total average daily dietary intake of heptadecanoic acid in an embodiment according to Example 2.

Building on the above results, a 24-week feeding study was accomplished on the case population (MMP) dolphins, to determine if the above-referenced triglycerides, glucose, insulin, and ferritin sera levels could be manipulated by manipulating the C 17:0 sera levels. To do this, the diets of the case population MMP dolphins were manipulated. More specifically, the diets of six MMP dolphins were modified to decrease capelin and introduce pinfish or mullet (fish with an increased amount of margaric acid) to their diet while maintaining the same diet caloric intake. Stated differently, and as shown in FIG. 14, the average daily intake of heptadecanoic acid was increased from approximately 400 mg to 1700 mg. The increase to 1700±500 mg daily heptadecanoic acid was equal to an approximate minimum daily heptadecanoic acid intake of 3 mg/lb body weight (6 mg/kg body weight). To evaluate potential confounding effects of the environment outside of the feeding study on the dolphins, eight MMP dolphins, which were housed in the same environment but not included in the feeding study, were monitored as references; these dolphins also had routine monthly blood samples collected during months 0, 1, 3, 4, and 6.

Figure 15:
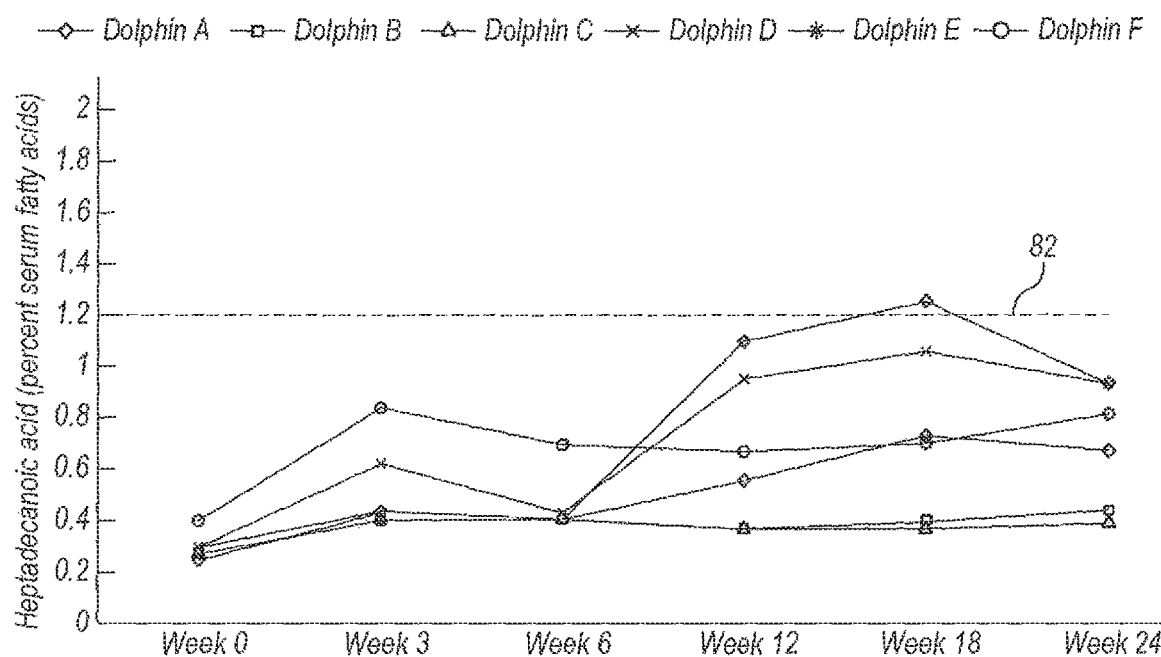
FIG. 15 provides data for heptadecanoic acid in both subject sera (%) in an embodiment according to Example 2. The dotted line represents the mean value for wild dolphins.
Figure 16:
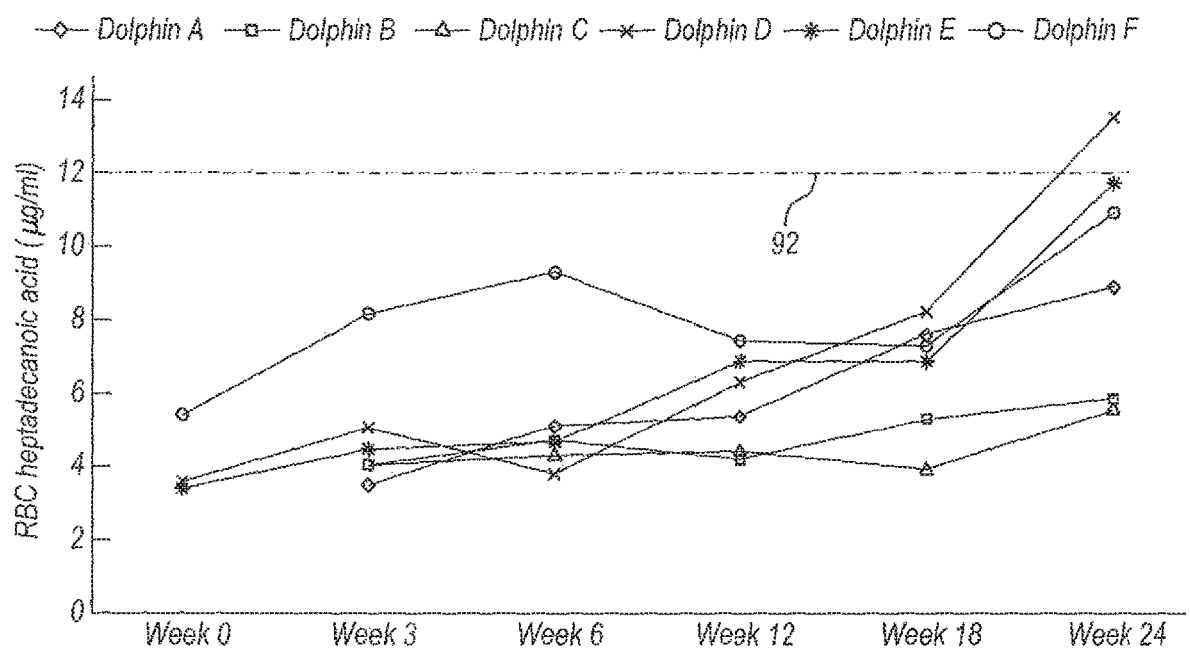
FIG. 16 provides data for heptadecanoic acid in subject red blood cell (RBC) membranes Wimp in an embodiment according to Example 2. The dotted line represents the mean value for wild dolphins.

FIGS. 15 and 16 are graphs of sera heptadecanoic acid (as a percent serum fatty acid and RBC in µg/ml, respectively) for the MMP dolphins resulting from the above-described feeding study. Additionally, mean levels of margaric acid in Sarasota Bay dolphins (indicated by lines 82 and 92 in FIGS. 15-16) are included as a comparison. As can be seen in FIGS. 15-16, as a result of the increase in heptadecanoic acid intake, serum levels of heptadecanoic acid were higher in feeding study dolphins during weeks 3, 6, 12, 18, and 24 when compared to week 0.

Figure 17:
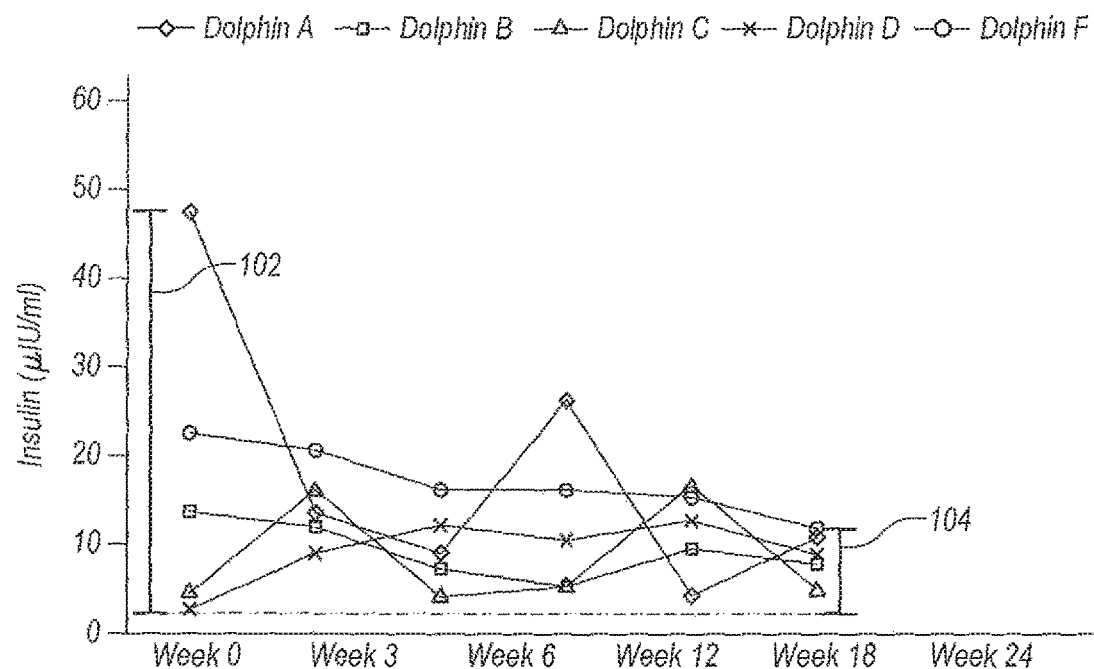
FIG. 17 provides data for sera insulin levels in an embodiment according to Example 2. The dotted line represents the mean value for wild dolphins.

To determine the effects of increased sera heptadecanoic acid depicted in FIGS. 15-16, the insulin in the feeding study dolphins was measured. The measurement results are depicted in FIG. 17. As shown in FIG. 17, the insulin levels of the feeding study dolphins decreased during the period of the feeding study, which confirms the effects of the increased margaric acid in the subject sera. In addition, and perhaps just as importantly, a normalization of spread of insulin values for the subject sera was observed from an initial spread illustrated by line 102 at the start of the study (0 weeks) to a final spread 104 at 24 weeks.

Figure 18:
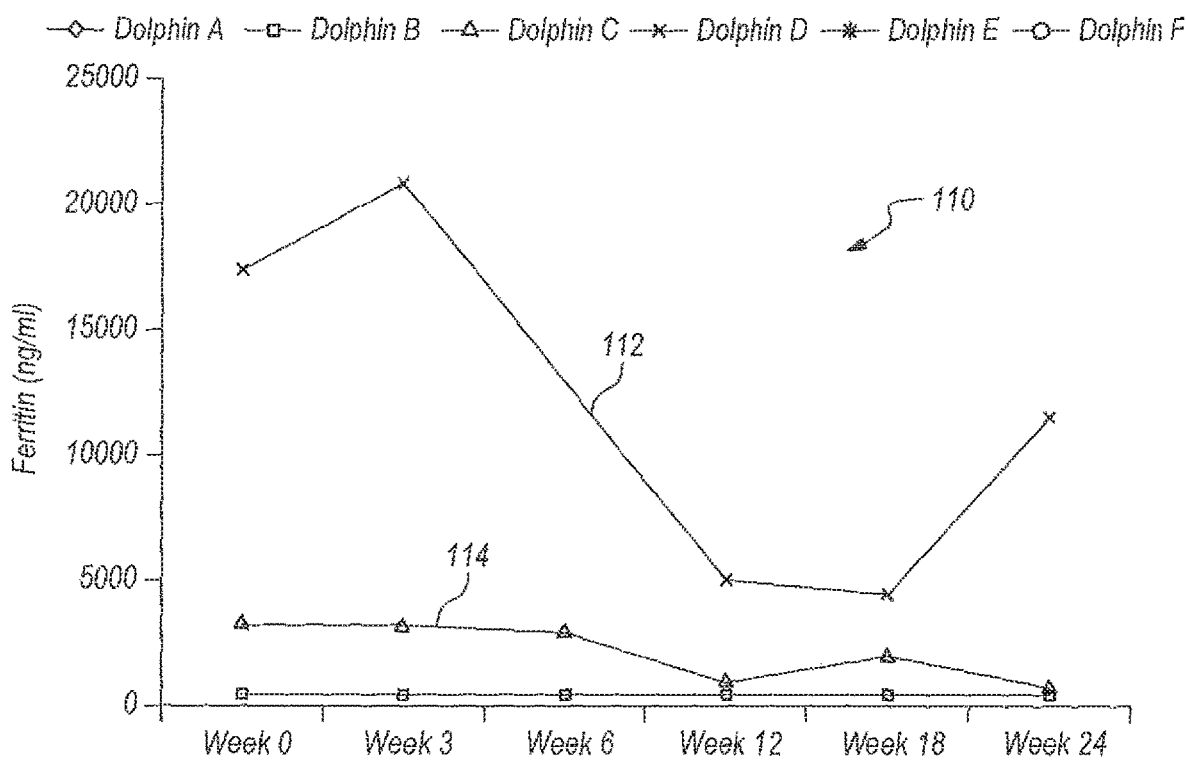
FIG. 18 provides data for sera ferritin in an embodiment according to Example 2.
Figure 19:
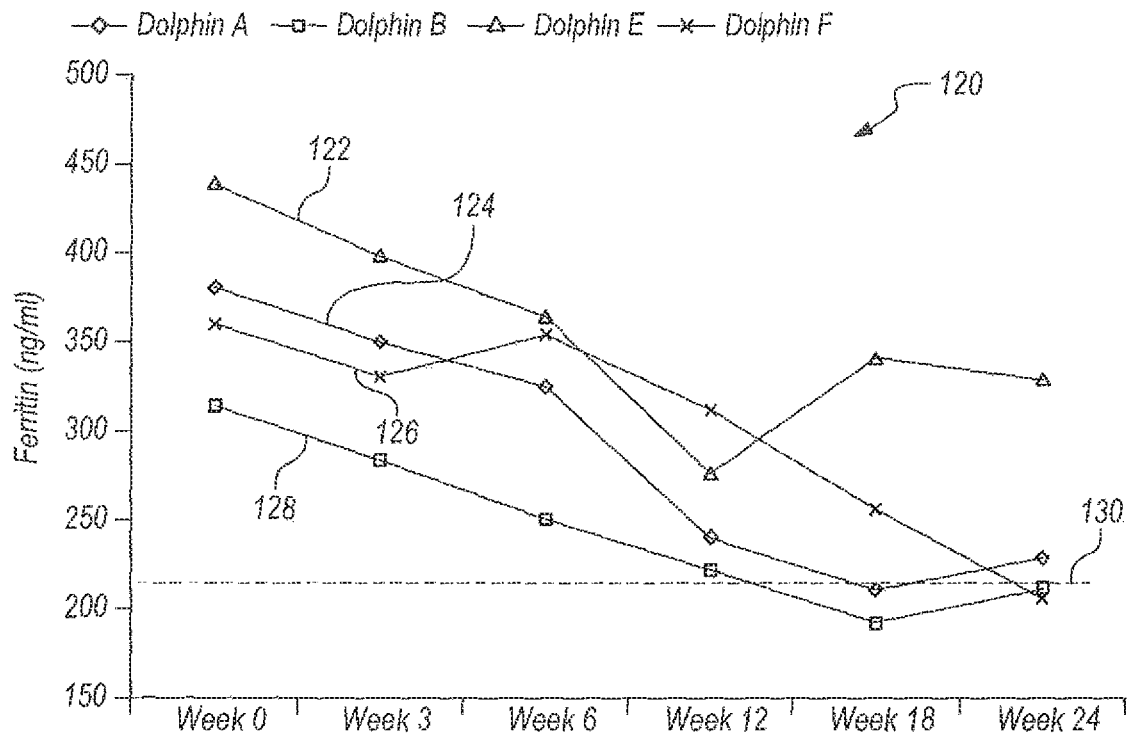
FIG. 19 provides data for sera ferritin in an embodiment according to Example 2. The dotted line represents the mean value for wild dolphins.

To determine the effects of increased sera margaric acid depicted in FIGS. 15-16 on ferritin levels, and referring now to graphs 110 and 120 in respective FIGS. 18 and 19, the ferritin in the feeding study dolphins was measured. As shown in FIGS. 18 and 19, serum ferritin levels continually decreased in all six dolphins throughout the feeding study, with weeks 3 through 24 having lower levels than week 0. Excluding the two extremely high ferritin outliers depicted by lines 112 and 114 in FIG. 17 (ferritin levels in the upper thousands to tens of thousands); the remaining dolphins (represented by lines 122, 124, 126 and 128 in FIG. 18) had the lowest mean serum ferritin (243±58 ng/ml) by week 24. Moreover, the mean ferritin levels for these dolphins approached the Sarasota Bay dolphins' mean value of 219±184 ng/ml, as depicted by line 130 in FIG. 19 (For purposes of the specification a therapeutic level can be defined as the mean level of Sarasota Bay dolphins). Due to the dramatic decrease in serum ferritin in all six feeding study dolphins, indices of acute inflammation (ceruloplamsin and haptoglobin) were assessed. Despite decreases in ferritin, there were no differences in these two proteins during any of the study weeks compared to week 0, supporting a conclusion that the decreased ferritin was not due to decreased acute inflammation.

Figure 20:
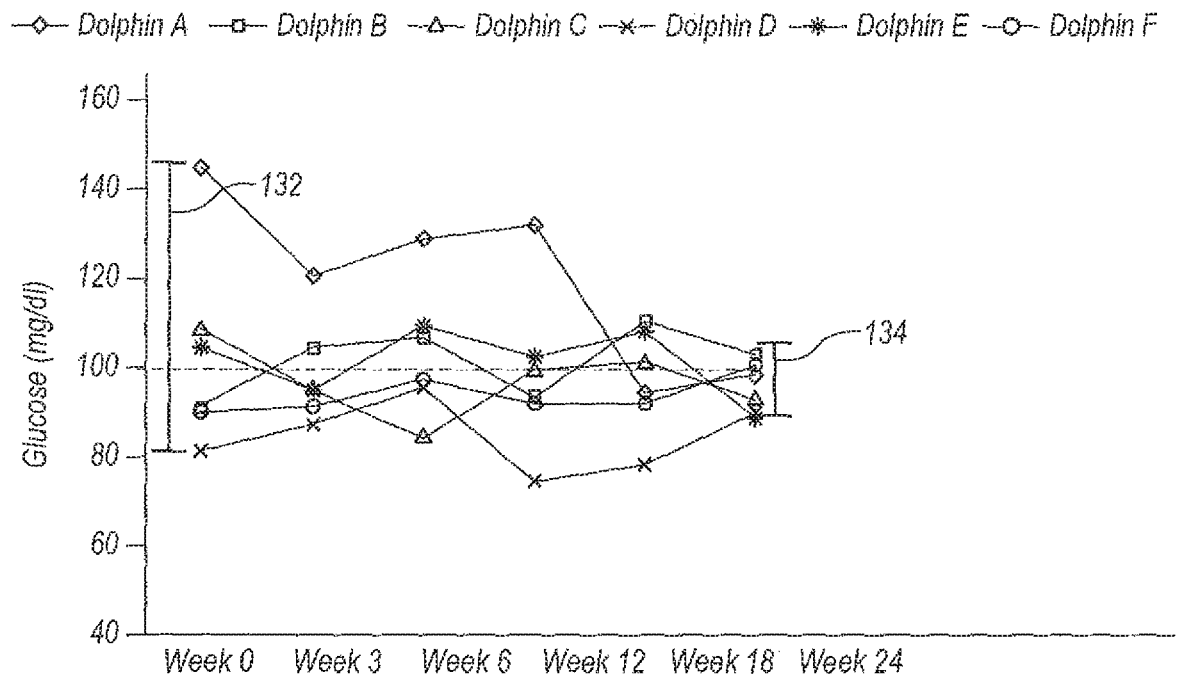
FIG. 20 provides data for sera glucose levels in an embodiment according to Example 2. The dotted line represents the mean value for wild dolphins.
Figure 21:
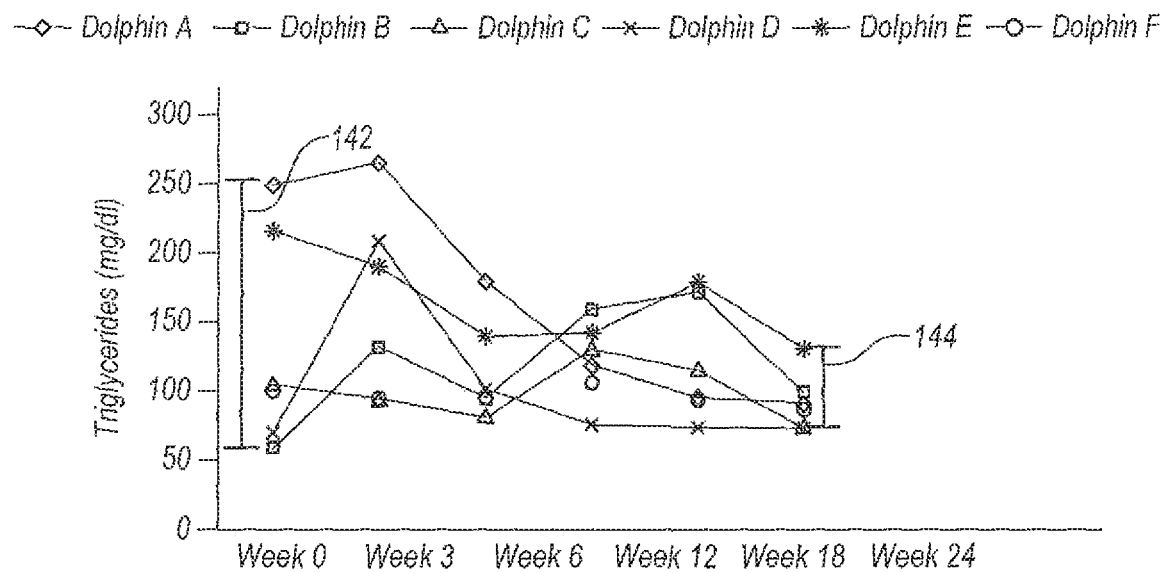
FIG. 21 provides data for sera triglyceride levels in an embodiment according to Example 2. The dotted line represents the mean value for wild dolphins.

In addition to the decrease in ferritin, and referring now to FIGS. 17, 20 and 21, there was a distinct decrease in measures of spread for insulin, glucose, and triglycerides that trended from weeks 0 to 24, i.e., there was a normalization of insulin, glucose and triglycerides level in subject sera. Changes in serum insulin, glucose, triglycerides, and ferritin during week 0 were compared to weeks 3, 6, 12, 18 and 24 values were compared to week 0 using pairwise comparison t-tests (in the reference population, month 0 values were compared to months 1, 3, 4 and 6). Given the apparent tightening or normalization of glucose, triglycerides, and insulin (5 of 6 dolphins) values among feeding study dolphins by week 24, measures of spread (standard deviation, SD, and coefficient of variance, CV) were compared between weeks 0 and 24 for glucose, triglycerides, and insulin; outcomes were compared to the reference dolphin group. CV was calculated as follows: standard deviation/ mean).

With regard to decreasing measures of spread, the insulin standard deviation (FIG. 17) decreased from about 50 to about 12 µIU/ml, while the standard deviation for glucose (FIG. 20) decreased from approximately 70 to 20 mg/dl. The standard deviation for triglycerides (FIG. 21) decreased from about 200 to 90 mg/dl. The coefficient of variation (C.V.) from week 0 to week 24 decreased from 22% to 6% for glucose and 61% to 24·% for triglycerides. When limiting to five study dolphins (excluding the outlier sixth dolphin), the insulin C.V. decreased from 100% to 38%. The decrease in measures of spread for these three key variables (normalization) is visually apparent from lines 102 and 104 in FIG. 17, initial spread 132 and final spread 134 in FIG. 20, and respective initial and final spreads 142 and 144 in FIG. 21.

Among the reference dolphin group for the feeding study (dolphins whose diet was not modified), there was not a difference in serum ferritin (week 0=4,116±2,822 ng/ml) compared to weeks 3, 12, and 18 (4,433±3,000, 4,055±2,534, and 3,418±2,059 ng/ml respectively; P=0.43, 0.92, and 0.37). There were also no differences in glucose and triglycerides when comparing week 0 with weeks 3, 12, and 18 (not shown); and the measures of spread for glucose and triglycerides did not decrease from week 0 to week 18 (standard deviation=16 and 15 mg/dl, C.V.=16% and 15% for glucose; and 58 and 48 mg/dl, C.V.=74% and 66% for triglycerides, respectively). Similarly, serum heptadecanoic acid (9.3±4 versus 9.3±4 ng/dl; P=0.98) glucose, and triglycerides did not differ in mean or measures of spread for the reference population when comparing month 0 with month 4.

While not statistically significantly different using the applied methods based upon the mean, mean levels of all three indicators of metabolic syndrome did trend down; for week 0 versus week 24, mean insulin decreased from 24 to 16 pIU/ml, glucose from 105 to 95 mg/dl, and triglycerides from 132 to 87 mg/dl. In sum, FIGS. 17-21 can be taken to mean that increased levels of heptadecanoic acid can result in a decrease of ferritin levels and a normalization of metabolic syndrome biomarkers in subject sera.

Heptadecanoic acid is an independent predictor among a full suite of metabolic syndrome indices, including glucose, insulin, triglycerides, and associated ferritin. When dolphins with hyperferritinemia increased their dietary intake of heptadecanoic acid by changing fish types fed, ferritin, glucose, triglycerides, and insulin normalized by week 24. Because hyperferritinemia in humans is associated with metabolic syndrome, and resolution of iron overload with phlebotomy improves insulin resistance, this suggests how heptadecanoic acid deficiencies may be an underlying and treatable cause of hyperferritinemia and subsequent metabolic syndrome in humans. This may be because bottlenose dolphins (*Tursiops truncatus*) and humans are large-brained, long lived species that develop similar diseases, including conditions associated with abnormal metabolism and aging. As such, dolphins have emerged as valuable animal models relevant to human health.

Several parallels have been identified between dolphins and humans. For example, dolphins and humans are long-lived. The average lifespan of dolphin is 20 years in the wild and 32 years at the MMP, with the maximum lifespan being approximately 60 years. Shared long lifespans between dolphins and humans are improving knowledge of chronic and aging-associated diseases in humans, including metabolic syndrome. Additionally, dolphins and humans have large brains. Among mammals, humans have the highest encephalization quotient (EQ=7.4), defined as the actual versus expected brain size given a species' body size. Second to humans is the bottlenose dolphin (EQ=5.3), higher than the chimpanzee (EQ=2.4) and much higher than the mouse (EQ=0.5). Similar to humans, positron emission tomography scans of living dolphins have revealed high levels of glucose consumption by the dolphin brain. As such, shared large brain size and associated high demand for glucose are likely drivers for common glucose metabolism and associated conditions in dolphins and humans.

In addition to the above, dolphins and humans have common pancreas histomorphology. The pancreas is responsible for production of insulin, a key hormone that regulates glucose metabolism. The microscopic structure of the dolphin pancreas is a mix of both porcine (pig) and human. Specifically, pancreatic giant islets, originally believed to be unique to primates, are also present in the dolphin pancreas. Further, pancreatic islet cells increased in size with age, a phenomenon that occurs in aging people with type 2 diabetes. Finally, cetacean insulin is identical to porcine insulin, which is only one amino acid different than human insulin, demonstrating that cetacean, porcine, and human insulin are similar. Parallels between dolphins and humans related to the pancreas support the dolphin's comparative value for human metabolic syndrome and diabetes.

Dolphins and humans have similar glucose transport systems, as well as common genetic adaptations associated with glucose metabolism. Adult dolphins have a high capacity for red blood cell glucose transport using the GLUT-1 transporter isoform; previous to this discovery, this capability was thought to be limited to primates. Common red blood cell glucose transport systems in cetaceans and primates are believed to be due to high central nervous system glucose demands. Also, the dolphin genome has been partially sequenced by Baylor University, based upon a dolphin at the U.S. Navy Marine Mammal Program. Dolphins have genetic evolutionary adaptations that are unique to long-lived, large brained species, including humans and elephants. Further, dolphins and humans have similar genes responsible for glucose metabolism (Office of Naval Research funded study, unpublished). Accordingly, Dolphins are appropriate models for human metabolic syndrome, diabetes, hyperferritinemia, and related conditions.

Dolphins and Humans Develop Similar Diseases and Disease Complications

Similar to humans, common bottlenose dolphins (*Tursiops truncatus*) can develop subclinical metabolic syndrome, including elevated insulin, triglycerides, glucose, and ferritin, as well as fatty liver disease. Dolphins managed at the Navy Marine Mammal Program living in San Diego Bay, Calif., are a well-studied population with regard to metabolism, and this group has higher insulin, triglycerides, ferritin, and iron compared to a wild bottlenose dolphin group living in Sarasota Bay, Fla. Importantly, the presence of case and reference populations of dolphins for metabolic syndrome parallel similar human population comparisons.

Similar to people, dolphins can develop nonalcoholic fatty liver disease (NAFLD). NAFLD has been found in both wild and managed collection dolphins, supporting that dolphins have general physiologic susceptibilities to metabolic syndrome. NAFLD is associated with metabolic syndrome in both dolphins and humans, and progresses to hepatitis and cirrhosis. Progression of these metabolic perturbations in both species is associated with insulin resistance and worsened glucose control.

Similar to humans, dolphins can develop a chronic condition involving high ferritin (hyperferritinemia) and iron. This disease in humans and dolphins involves excessive iron deposition primarily in the liver's Kupffer cells, progression with age, and associations with elevated lipids, insulin, and liver enzymes. This metabolic state in dolphins is associated with neither mutations in the HFE gene.

Dolphins develop similar age-associated blood changes as aging humans. Specifically, absolute lymphocytes, serum globulins, and mean platelet volume increase linearly with increasing old age (=aging from 30 up to 50 years old). Mean white blood cells, neutrophils, serum globulins, erythrocyte sedimentation rates, serum cholesterol, and serum triglycerides; and the prevalence of neutrophilic leukocytosis, hyperglobulinemia, and hypercholesterolemia, were more likely to be higher as geriatric dolphins got older. This study demonstrated that older dolphins have changes in hematological and serum chemistry values similar to those found in older humans. As such, bottlenose dolphins can serve as a useful comparative model for aging in humans.

Dolphins and humans have a common evolutionary driver for insulin resistance. An increasingly accepted theory is that insulin resistance in humans evolved in ancestral primates during the last ice age. During this time, our ancestors changed from a high carbohydrate, low protein diet to a low carbohydrate, high protein diet. This change enabled genetic selection of insulin resistance to help maintain blood sugar levels needed for large brains. When humans returned to increasingly high carbohydrate diets, however, insulin resistance became a pathologic condition and led to type 2 diabetes. Approximately fifty-five million years ago, the dolphin was a terrestrial mammal that evolved to live completely in the marine environment. The closest terrestrial relatives of dolphins are artiodactyls, including cows, pigs, and camels. Most of these relatives are strict herbivores, and none are strict carnivores. As such, it may be assumed that the terrestrial ancestor of dolphins ate a high carbohydrate, low protein diet. Similar to the evolutionary path of humans during the ice age, dolphins changed to a high protein, low carbohydrate diet when they moved to the ocean. Because dolphins, too, have developed large brains with high demands for readily available glucose, they may have also selected for insulin resistance to maintain high blood glucose levels.

For the above reasons, dolphins and humans share important common ground related to anatomy, physiology, and disease states that support the dolphin as an important and relevant animal model for human diseases, including metabolic syndrome and hyperferritinemia. The results cited herein for dolphins can also be beneficial for humans.

Heptadecanoic acid (C17:0), also called margaric acid, is a saturated fatty acid present in bovine milk fat and was the original component of margarine (hence, margarine's name) in the late 1800s. Heptadecanoic acid in margarine, however, was replaced with less costly and more readily available plant-based and trans-fatty acids. When off the shelf dairy products were tested in the current study, heptadecanoic acid was highest in butter and whole fat yogurt and absent in nonfat dairy products. Interestingly, despite consumer's movement away from high fat foods, dairy consumption in humans has been associated with multiple health benefits, including lower risks of insulin resistance syndrome, metabolic syndrome, and type 2 diabetes. To date, the mechanism of the benefits of dairy products on human metabolism has not been determined. Based upon the results using the methods of the embodiments, it can be proposed that heptadecanoic acid may be a key player in the metabolic benefits of dairy products in humans.

To take advantage of these benefits, heptadecanoic acid can be used in acid in a supplement, food additive, food fortifier, beverage additive, beverage fortifier, or pharmaceutical in any form, including as a tablet, encapsulated pill, gelcap pill, liquid suspension, spray, and powder. Additionally, diagnostic tests and assays for heptadecanoic acid in human and animal samples (including blood (serum, plasma, and erythrocyte membranes), urine, and feces) can be used to detect low heptadecanoic acid levels and to continually monitor heptadecanoic acid levels in patients. The use of heptadecanoic acid can prevent, stem, and treat: 1) Elevated ferritin and associated complications, including iron overload, metabolic syndrome, type 2 diabetes, autoimmune diseases, and neurodegenerative diseases (including but not limited to Alzheimer's disease, Parkinson's disease, and restless leg syndrome); and, 2) Metabolic syndrome components and associated complications, including dyslipidemia, hypertriglyceridemia, elevated glucose, elevated insulin, type 2 diabetes, heart disease, and stroke. These egregious health effects can be prevented not only in dolphins, but because of the similarities in blood panels, they can be prevented in human mammals as well.

Figure 22:
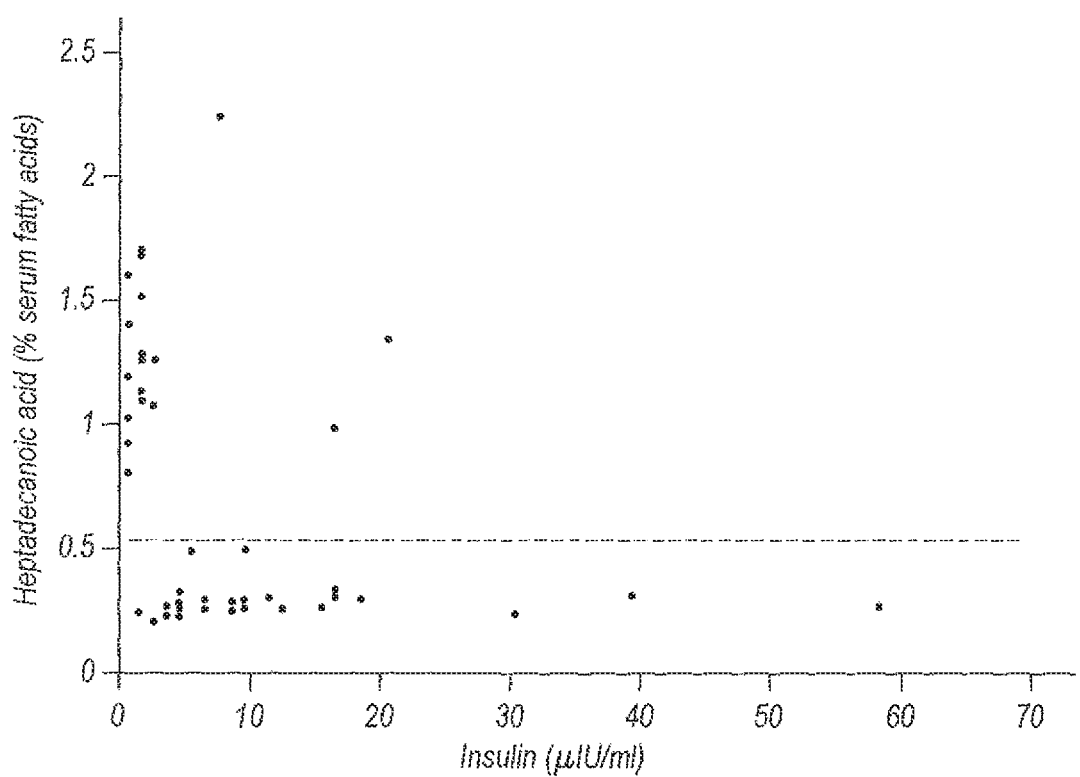
FIG. 22 provides data for heptadecanoic acid (% serum fatty acids) versus insulin in an embodiment according to Example 2. The dotted line provides an exemplary serum heptadecanoic acid threshold to maintain low insulin.

Referring now to FIG. 22, scatter plots of heptadecanoic acid versus insulin for both the control populations and the study populations is shown. As shown in FIG. 22, using a proposed therapeutic threshold of serum heptadecanoic of 0.4 percent as percent of the total fatty acid in serums, can maintain a low insulin (as defined above) level.

It is unknown precisely how high ferritin increases the risk of diabetes, but proposed mechanisms include direct injury to the liver and pancreas from excessive deposition or indirect injury from increased oxidative radicals. Currently, the most accepted means of treating hyperferritinemia and associated iron overload in humans is phlebotomy (removal of iron in the blood). The methods according to several embodiments describe methods wherein hyperferritinemia that is associated with prediabetes can be reversible using a modified diet most likely involving increased dietary intake of heptadecanoic acid. Reversal of hyperferritinemia by week 3 using the modified diet was followed by normalization of prediabetes/metabolic syndrome (normalized glucose, insulin, and triglycerides) at week 24, as described above. In fact, the methods of the embodiments can be used to treat hyperferritinemia with requiring phlebotomy.

Figure 23:
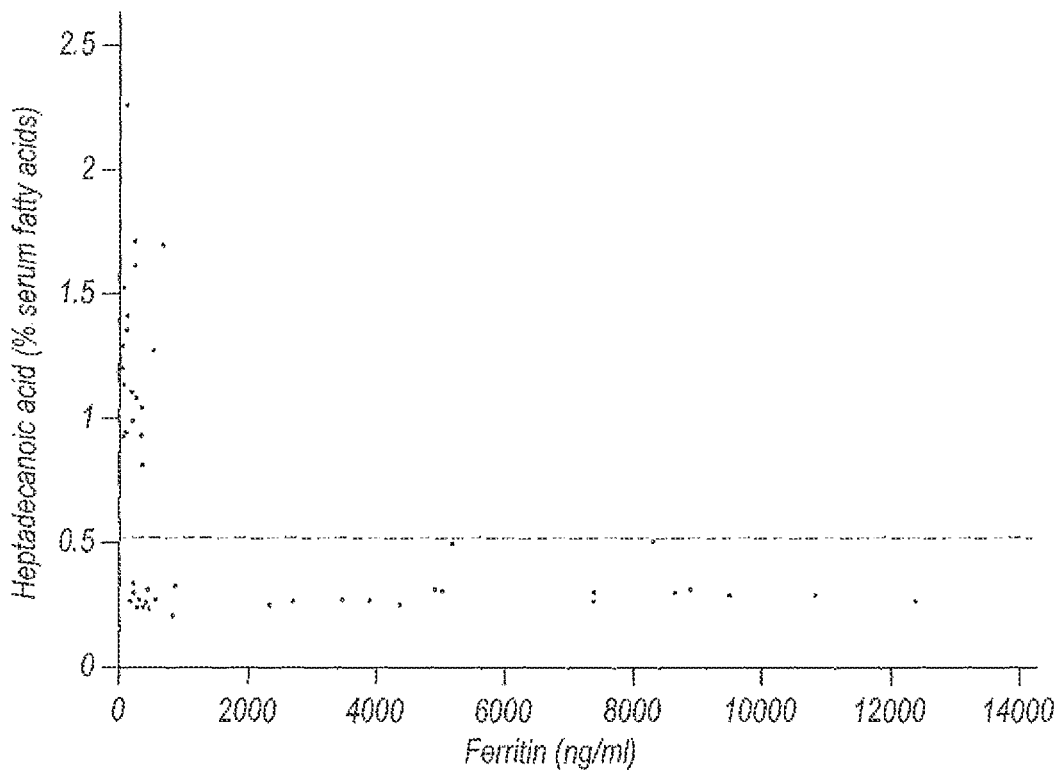
FIG. 23 provides data for heptadecanoic acid (% serum fatty acids) versus ferritin, in an embodiment according to Example 2. The dotted line provides an exemplary serum heptadecanoic acid threshold to maintain normal ferritin.
Figure 24:
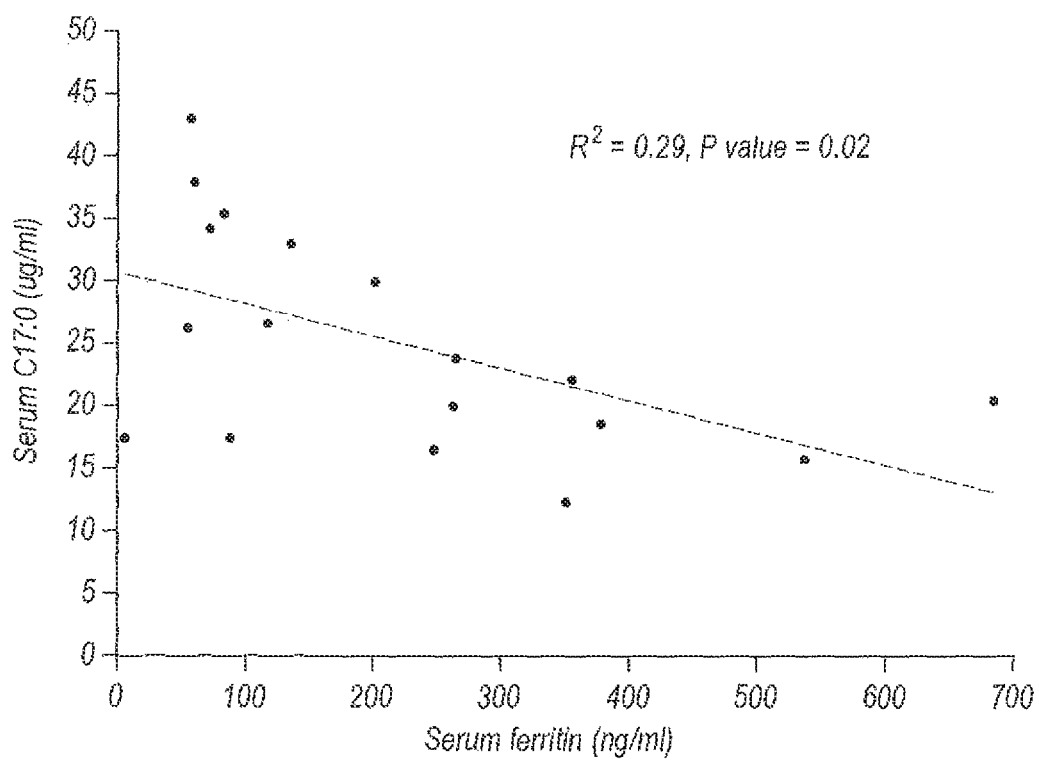
FIG. 24 provides an inverse association between total serum C17:0 and serum ferritin in an embodiment according to Example 1.
Figure 25:
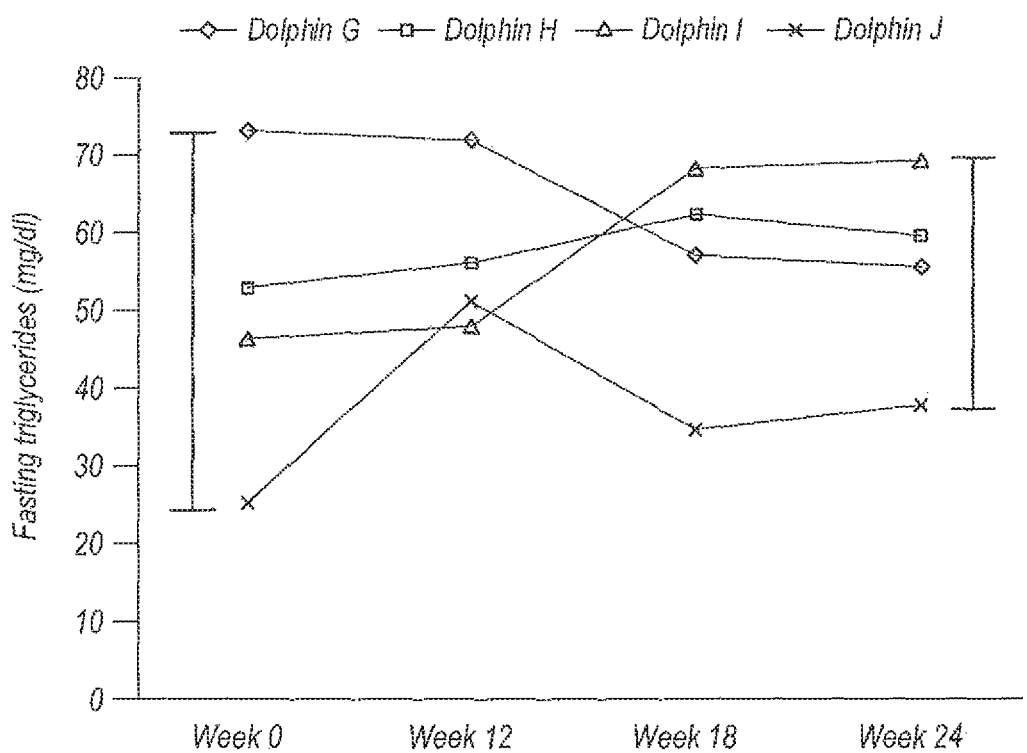
FIG. 25 provides data for fasting triglycerides in an embodiment according to Example 1.
Figure 26:
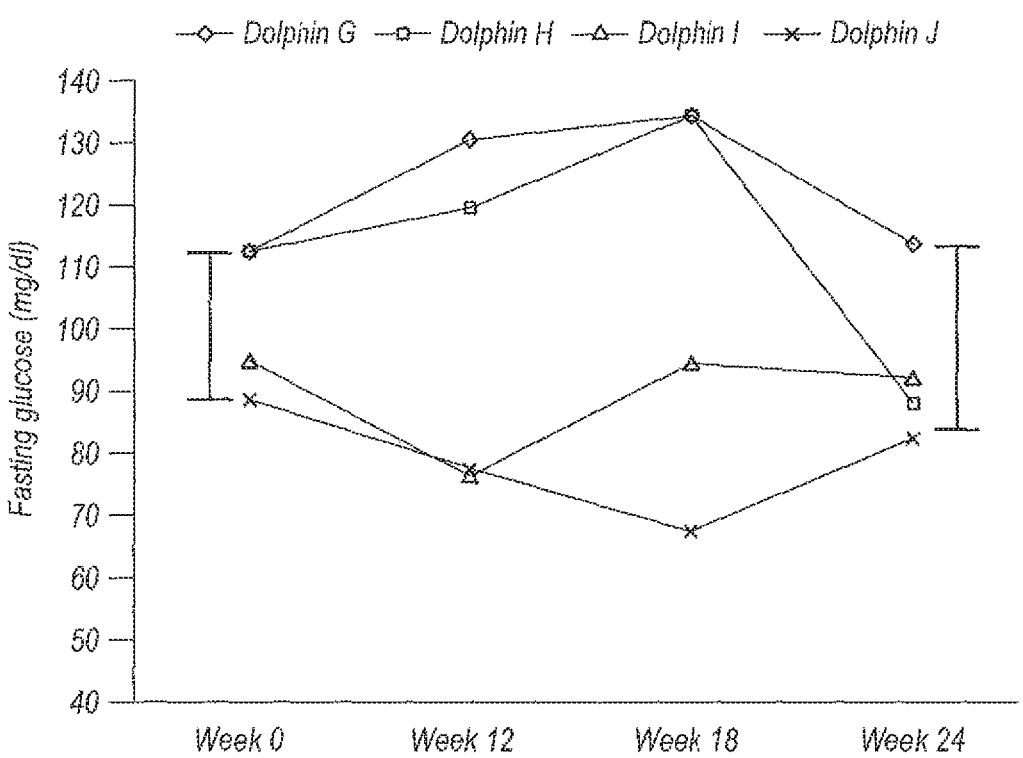
FIG. 26 provides data for fasting glucose in an embodiment according to Example 1.
Figure 27:
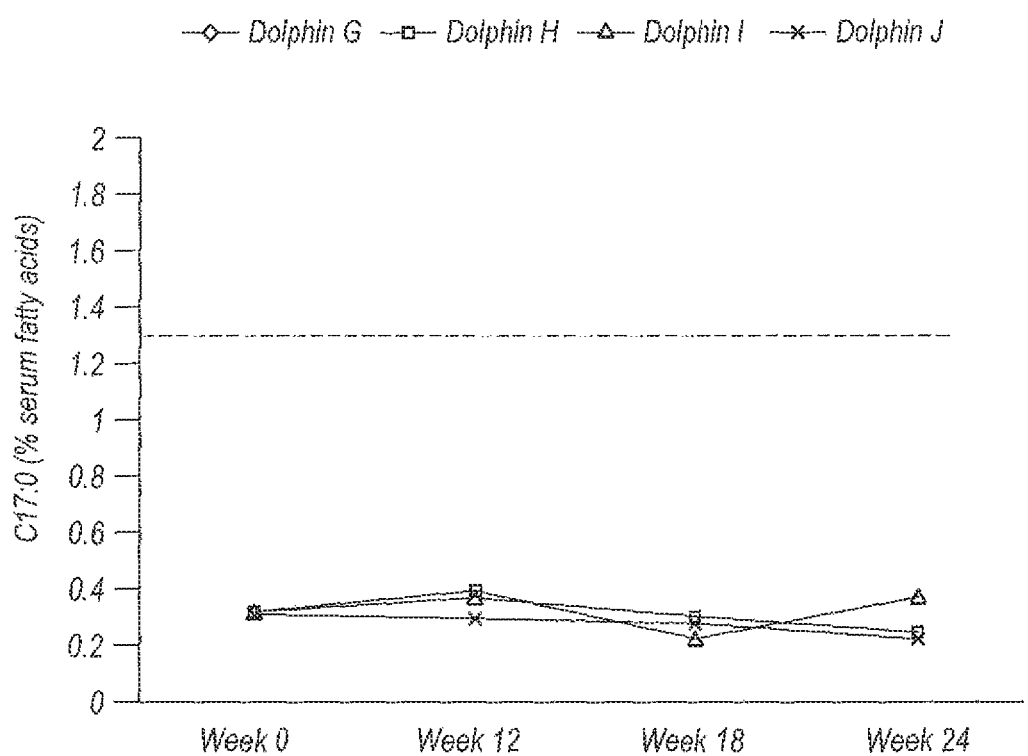
FIG. 27 provides data for C17:0 as a percentage of serum fatty acids in an embodiment according to Example 1.

Referring now to FIG. 23, scatter plots of heptadecanoic acid versus ferritin levels for both the control populations and the study populations is shown. As shown in FIG. 23, using a proposed therapeutic threshold of serum heptadecanoic of 0.4 percent as percent of the total fatty acid in serums, can also maintain a therapeutic ferritin (as defined above) level.

Study dolphins from MMP and Sarasota Bay live in the open ocean, and known dietary intake was limited to fish fed to MMP dolphins. MMP dolphins live in netted enclosures in San Diego Bay, and changing populations of local fish are readily available to eat. While MMP dolphins can eat local fish, however, observation of feeding behaviors by MMP's animal care staff and maintained dolphin appetites for fed fish support that the majority of dietary fish are those that are fed by the MMP. Reference dolphins in the same population and environment, however, did not have the same decreases in serum ferritin and normalization of glucose and triglycerides. The data suggest a direct effect for heptadecanoic acid on lowering high serum ferritin in the feeding study involved fish with higher heptadecanoic acid. The potential impact (or cumulative impacts) of other nutrients in the modified diet on serum ferritin has not been determined. Identification of 1) higher serum percent heptadecanoic acid as an independent predictor of lower serum ferritin, 2) demonstrated increased dietary intake and percent serum heptadecanoic acid during the feeding study, and 3) coincident decreases in serum ferritin and increases in percent serum heptadecanoic acid by week 3, provide evidence that increasing dietary heptadecanoic acid contributed to decreased serum ferritin, which indicates that heptadecanoic acid can be used to treat hyperferritinemia, metabolic syndrome, and diabetes, as well as other associated or related conditions.

Heptadecanoic acid deficiencies can be used to detect a risk of or cause for metabolic syndrome and associated hyperferritinemia. Dietary supplementation with heptadecanoic acid can help resolve both conditions, as well as type 2 diabetes. Further, given hyperferritinemia's association with autoimmunity in humans, the use of heptadecanoic acid deficiency detection and resolution as a means to prevent or manage disease can apply to type 1 diabetes, as well as other autoimmune diseases.

The following materials are incorporated herein by reference in the entirety: Colegrove K. et al. (2015) Histomorphology of the bottlenose dolphin (*Tursiops truncatus*) pancreas and association of increasing islet f3-cell size with chronic hypercholesterolemia. J Gen Comp Endocrinol 14:17-23; Venn-Watson S. et al. (2012) Hemochromatosis and fatty change: building evidence for insulin resistance in bottlenose dolphins (*Tursiops truncatus*). J Zoo Wildlf Med 43:S35-S47; Venn-Watson S. et al. (2007) Big brains and blood glucose: Common ground for diabetes mellitus in humans and healthy dolphins. Comp Med 57:390-5; Venn-Watson S. et al. (2013) Blood-Based Indicators of Insulin Resistance and Metabolic Syndrome in Bottlenose Dolphins (*Tursiops truncatus*). Front Endocrinol (Lausanne) 4:136; Venn-Watson S. et al. (2011) Dolphins as animal models for type 2 diabetes: Sustained, postprandial hyperglycemia and hyperinsulinemia. Gen Comp Endocrin 170:193-9; Venn-Watson S. et al. (2014) Dolphins and Diabetes: Applying One Health for breakthrough discoveries. Front Endocrinol DOI 10.3389/fendo.2014.00227; Venn-Watson S. et al. (2015) Increased dietary intake of saturated fatty acid heptadecanoic acid (C17:0) associated with decreasing ferritin and alleviated metabolic syndrome in dolphins. PLOS ONE 10:e0132117.

Methods and compositions related to or applicable to metabolic syndrome or related conditions are discussed in the following references, which are incorporated by reference herein in their entirety: Craik J et al. (1998) GLUT-I mediation of rapid glucose transport in dolphin (*Tursiops truncatus*) red blood cells. Am J Physiol 274:R112-R9; McGowen M, et al. (2012) Dolphin genome provides evidence for adaptive evolution of nervous system genes and a molecular rate slowdown. Royal Society Proc B 279:3643-51; Jenkins B, et al. (2015) A review of odd-chain fatty acid metabolism and the role of pentadecanoic acid (C15:0) and heptadecanoic acid (C17:0) in health and disease. Molecules 20:2425-44; Mansson H L (2008) Fatty acids in bovine milk fat. Food Nutr Res 52:4; Magnusdottir O K, et al. (2014) Plasma alkylresorcinols C17:0/C21:0 ratio, a biomarker of relative whole-grain rye intake, is associated to insulin sensitivity: a randomized study. Eur J Clin Nutr 68:453-458; Luzia L A, et al. (2013) The influence of season on the lipid profiles of five commercially important species of Brazilian fish. Food Chem 83:93-97; Benatar J R, et al. (2014) The effects of changing dairy intake on trans and saturated fatty acid levels—results from a randomized controlled study. Nutr J 13:32; Abdullah M M, et al. (2015) Recommended dairy product intake modulates circulating fatty acid profile in healthy adults: a multi-centre cross-over study. Br J Nutr 113:435-44; Forouhi N, et al. (2014) Differences in the prospective association between individual plasma phospholipid saturated fatty acids and incident type 2 diabetes: the EPIC-InterAct case-cohort study. Lancet Diabetes Endocrinol 2:810-8; Patel P, et al. (2010) Fatty acids measured in plasma and erythrocyte-membrane phospholipids and derived by food-frequency questionnaire and the risk of new-onset type 2 diabetes: a pilot study in the European Prospective Investigation into Cancer and Nutrition (EPIC)-Norfolk cohort. Am J Clin Nutrition 92: 1214-22; Krachler B, et al. (2008) Fatty acid profile of the erythrocyte membrane preceding development of Type 2 diabetes mellitus. Nutrition, metabolism, and cardiovascular diseases. Nl\rICD 18:503-10; Maruyama C et al. (2008) Differences in serum phospholipid fatty acid compositions and estimated desaturase activities between Japanese men with and without metabolic syndrome. J Atherscler Thromb 15:306-313; Choi H, et al. (2005) Dairy consumption and risk of type 2 diabetes mellitus in men: a prospective study. JAMA Internal Med 165:997-1003; Kratz M, et al. (2014) Dairy fat intake is associated with glucose tolerance, hepatic and systemic insulin sensitivity, and liver fat but not beta-cell function in humans. The American Journal of Clinical Nutrition. 99: 1385-96; Mennen L, et al. (2000) Possible protective effect of bread and dairy products on the risk of the metabolic syndrome. Nutrition Research 20:335-47; Pereira M, et al. (2002) Dairy consumption, obesity, and the insulin resistance syndrome in young adults: the CARDIA study. JAMA 287:2081-9; Sandrou D, et al. (2000) Low-fat/calorie foods: current state and perspectives. Crit Rev Food Sci Nutr 40:427-47; Pfeuffer M, et al. (2006) Milk and the metabolic syndrome. Obesity Rev 8:109-18; Jehn M, et al. (2004) Serum ferritin and risk of the metabolic syndrome in U.S. adults. Diabetes Care 27:2422-2428; Trombini P, et al. (2007) Ferritin, metabolic syndrome and NAFLD: elective attractions and dangerous liaisons. J Hepatol 46:549-552; Sun L, et al. (2008) Ferritin concentrations, metabolic syndrome, and type 2 diabetes in middle-age and elderly Chinese. J Clin Endocrinol Met 93:4690-4696; Yoneda M, et al. (2010) Serum ferritin is a clinical biomarker in Japanese patients with nonalcoholic steatoheptatitis (NASH) independent of HFE gene mutation. Dig Dis Sci 55:808-814; Jiang R, et al. (2004) Body iron stores in relation to risk of type 2 diabetes in apparently healthy women. JAMA 291:711-7; Fernandez-Real J, et al. (2004) Iron stores, blood donation, and insulin sensitivity and secretion. Clin Chem 51: 1201-5; Valenti L, et al. (2007) Iron depletion by phlebotomy improves insulin resistance in patients with nonalcoholic fatty liver disease and hyperferritinemia: evidence from a case-control study. Am J Gastroenterol 102:1251-8; Kadowaki T, et al. (2006) Adiponectin and adiponectin receptors in insulin resistance, diabetes, and the metabolic syndrome. J Clin Invest 116:1784-92; Pagano C, et al. (2005) Plasma adiponectin is decreased in nonalcoholic fatty liver disease. Eur J Endocrinol 152:113-8; Li S, et al. (2009) Adiponectin levels and risk of type 2 diabetes: a systematic review and meta-analysis JAMA 302: 179-88; Gabrielsen J, et al. (2012) Adipocyte iron regulates adiponectin and insulin sensitivity. J Clin Invest 122:3529-40; Wlazlo N, et al. (2012) Iron metabolism is associated with adipocyte insulin resistance and plasma adiponectin. Diabetes Care 36:309-15; Mazzaro L, et al. (2012) Iron indices among bottlenose dolphins (*Tursiops truncatus*): identifying populations at risk for iron overload. Comp Med 62:508-15; Neely B, et al. (2013) Radiometric measurements of adiponectin by mass spectrometry in bottlenose dolphins (*Tursiops truncatus*) with iron overload reveal an association with insulin resistance and glucagon. Front Endocrinol 4: 132; Futerman A H, et al. (2004) The complex life of simple sphingolipids. EMBO reports 5:777-782; Centers for Disease Control and Prevention. National Diabetes Statistics Report: Estimates of Diabetes and Its Burden in the United States, 2014. Atlanta, Ga.: U.S. Department of Health and Human Service. Available: http://www.cdc.gov/diabetes/pubs/statsreport 1 4/national-diabetes-report-web.pdf; Nanri A, et al. (2011) Fish intake and type 2 diabetes in Japanese men and women: the Japan Public Health Center-based Prospective Study. Am J Clin Nutr 94:884-891. doi: 10.3945/ajcn.111.012252 PMID: 21775559; Patel P S, et al. (2009) Association between type of dietary fish and seafood intake and incident type 2 diabetes: the European prospective investigation of cancer (EPIC)-Norfolk cohort study. Diab Care 32:1857-1863; Wallin A, et al. (2012) Fish consumption, dietary long-chain n-3 fatty acids, and risk of type 2 diabetes. Diab Care 35:918-929; Xun P, et al. (2012) Fish consumption and incidence of diabetes. Diab Care 35:930-938; Ruidavets J B, et al. (2007) High consumptions of grain, fish, dairy products and combinations of these are associated with a low prevalence of metabolic syndrome. J Epidemiol Community Health 61:810-817. PMID: 17699537; Gibson RA (1983) Australian fish-an excellent source of both arachidonic acid and n-3 polyunsaturated fatty acids. Lipids 18:743-752; Glauber H, et al. (1988) Adverse metabolic effect of omega-3 fatty acids in non-insulin-dependent diabetes mellitus. Ann Int Med 108:663-668. PMID: 3282462; Popp-Snijders C, et al. (1987) Dietary supplementation of omega-3 polyunsaturated fatty acids improve insulin sensitivity in non-insulin-dependent diabetes. Diabetes Res 4:141-147. PMID: 3038454; Wells R S, et al. (2013) Evaluation of potential protective factors against metabolic syndrome in bottlenose dolphins: feeding and activity patterns of dolphins in Sarasota Bay, Fla. Frontiers Endo 4: 139; Ellervik C, et al. (2001) Prevalence of hereditary haemochromatosis in late-onset type 1 diabetes mellitus: a retrospective study. Lancet 358: 1405-1409. PMID: 11705485; Fernandez-Real J N I, et al. (2002) Cross-talk between iron metabolism and diabetes. Diabetes 51:2348-2354. PMID: 12145144; Jehn M, et al. (2004) Serum ferritin and risk of the metabolic syndrome in U.S. adults. Diabetes Care 27:2422-2428. PMID: 15451911; Swaminathan S, et al. (2007) Role of iron in diabetes and its complications. Diabetes Care 30:1926-1933. PMID: 17429063; Adams P C, et al. (2005) Hemochromatosis and iron-overload screening in a racially diverse population. N Engl J Med 352: 1769-1778. PMID: 15858186; Johnson S P, et al. (2009) Use of phlebotomy treatment in Atlantic bottlenose dolphins with iron overload. J Am Vet Med Assoc 235: 194-200. doi: 10.2460/javma.235.2.194 PMID: 19601742; Mazzara L M, et al. (2012) Iron indices among bottlenose dolphins (*Tursiops truncatus*): identifying populations at risk for iron overload. Comp Med 62:508-515. PMID: 23561885; Phillips B E, et al. (2014) Preliminary investigation of bottlenose dolphins (*Tursiops truncatus*) for HFE gene-related hemochromatosis. J Wild Dis 50:891-895; Wells RS (2014) Social structure and life history of common bottlenose dolphins near Sarasota Bay, Fla.: Insights from four decades and five generations. Pp. 149-172 In: Yamagiwa J. and Karczmarski L. (eds.), Primates and Cetaceans: Field Research and Conservation of Complex Mammalian Societies, Primatology Monographs, Tokyo, Japan: Springer. doi: 10.1007/978-4-431-54523-1_8; Wells R S, et al. (2004) Bottlenose dolphins as marine ecosystem sentinels: developing a health monitoring system. EcoHealth 1:246-254; Barros N B, et al. (1998) Prey and feeding patterns of resident bottlenose dolphins (*Tursiops truncatus*) in Sarasota Bay, Fla. J Mammal 79:1045-1059; Berens-l\kCabe E, et al. (2010) Prey selection m a resident common bottlenose dolphin (*Tursiops truncatus*) community in Sarasota Bay, Fla. Marine Biol 157:931-942; Lagerstedt S A, et al. (2001) Quantitative determination of plasma C8-C26 total fatty acids for the biochemical diagnosis of nutritional and metabolic disorders. Mol Gen Metabol 73:38-45; Choi K M, et al. (2005) Association among serum ferritin, alanine aminotransferase levels, and metabolic syndrome in Korean postmenopausal women. Metab 54: 1510-1514; Valenti L, et al. (2007) Iron depletion by phlebotomy improves insulin resistance in patients with nonalcoholic fatty liver disease and hyperferritinemia: evidence from a case-control study. Am J Gastro 102:1251-1258; Anderson AJC (1954) Margarine. London. Pergamon Press; Mansson H L (2008) Fatty acids in bovine milk fat. Food Nutr Res 52:4; Fernandes R, et al. (2013) Relationship between acute phase proteins and serum fatty acid composition in morbidly obese patients. Dis Markers 35:104-102; Forouhi N G, et al. (2014) Differences in the prospective association between individual plasma phospholipid saturated fatty acids and incident type 2 diabetes: the EPIC-InterAct case-cohort study. Lancet Diabetes Endocrinol 2:810-818. doi: 10.1016/S2213-8587(14) 70146-9 PMID: 25107467; Benatar J R, et al. (2014) The effects of changing dairy intake on trans and saturated fatty acid levels-results from a randomized controlled study. Nutr J 13:32. doi: 10.1186/1475-2891-13-32 PMID:24708591; Slifka K A, et al. (2013) Comparative diet analysis of fish species commonly consumed by managed and free-ranging bottlenose dolphins (*Tursiops truncatus*). Int J Vet Med 10:1; Ozogul Y, et al. (2007) Fatty acid profiles and fat contents of commercially important seawater and freshwater fish species of Turkey: A comparative study. Food Chem 103:217-223; Suresh Y, et al. (2001) Protective action of arachidonic acid against alloxan-induced cytotoxicity and diabetes mellitus. Prostaglan Leuko Essent Fatty Acids 64:37-53; Venn-Watson S, et al. (2015) Adrenal gland and lung lesions in Gulf of Mexico common bottlenose dolphins (*Tursiops truncatus*) found dead following the Deepwater Horizon oil spill. PLOS ONE 10(5):e0126538. doi: 10.1371/journal.pone.0126538 PMID: 25992681; Venn-Watson S, et al. (2015) Annual survival, mortality, and longevity of bottlenose dolphins (*Tursiops truncatus*) at the U.S. Navy Marine Mammal Program, 2004-2013. J Am Vet Med 246:893-898; Venn-Watson S, et al. (2008) Clinical relevance of elevated transaminases in a bottlenose dolphin (*Tursiops truncatus*) population. J Wildlf Dis 44:318-330; Akbar, H., et al. (2015). Alterations in Hepatic FGF21, Co-Regulated Genes, and Upstream Metabolic Genes in Response to Nutrition, Ketosis and Inflammation in Peripartal Holstein Cows. PLoS One 10, e0139963. doi: 10.1371/journal.pone.0139963; Aso, Y., et al. (2010). Relation between serum high molecular weight adiponectin and serum ferritin or prohepcidin in patients with type 2 diabetes. Diabetes Res Clin Pract 90, 250-255. doi: 10.1016/j.diabres.2010.09.008; Bai, J., et al. (2011). Relationship between adiponectin and testosterone in patients with type 2 diabetes. Biochem Med (Zagreb) 21, 65-70; Bergman, B. C., et al. (2015). Serum sphingolipids: relationships to insulin sensitivity and changes with exercise in humans. Am J Physiol Endocrinol Metab 309, E398-408. doi: 10.1152/ajpendo.00134.2015; Bielawski, J., et al. (2006). Simultaneous quantitative analysis of bioactive sphingolipids by high-performance liquid chromatography-tandem mass spectrometry. Methods 39, 82-91. doi: 10.1016/j.ymeth.2006.05.004; Brozinick, J. T., et al. (2013). Plasma sphingolipids are biomarkers of metabolic syndrome in non-human primates maintained on a Western-style diet. Int J Obes (Lond) 37, 1064-1070. doi: 10.1038/ijo.2012.191; Ezaki, H., et al. (2009). Delayed liver regeneration after partial hepatectomy in adiponectin knockout mice. Biochem Biophys Res Commun 378, 68-72. doi: 10.1016/j.bbrc.2008.10.176; Fernandez-Real, J. M., et al. (1998). Serum ferritin as a component of the insulin resistance syndrome. Diabetes Care 21, 62-68; Gabrielsen, J. S., et al. (2012). Adipocyte iron regulates adiponectin and insulin sensitivity. J Clin Invest 122, 3529-3540. doi: 10.1172/JCI44421; Galman, C., et al. (2008). The circulating metabolic regulator FGF21 is induced by prolonged fasting and PPARalpha activation in man. Cell Metab 8, 169-174. doi: 10.1016/j.cmet.2008.06.014; Hall, A. J., et al. (2007). Annual, seasonal and individual variation in hematology and clinical blood chemistry profiles in bottlenose dolphins (*Tursiops truncatus*) from Sarasota Bay, Fla. Comp Biochem Physiol A Mol Integr Physiol 148, 266-277. doi: 10.1016/j.cbpa.2007.04.017; Hannun, Y. A., et al. (2008). Principles of bioactive lipid signalling: lessons from sphingolipids. Nat Rev Mol Cell Biol 9, 139-150. doi: 10.1038/nrm2329; Hassanali, Z., et al. (2010). Dietary supplementation of n-3 PUFA reduces weight gain and improves postprandial lipaemia and the associated inflammatory response in the obese JCR:LA-cp rat. Diabetes Obes Metab 12, 139-147. doi: 10.1111/j.1463-1326.2009.01130.x; Holland, W. L., et al. (2013). An FGF21-adiponectin-ceramide axis controls energy expenditure and insulin action in mice. Cell Metab 17, 790-797. doi: 10.1016/j.cmet.2013.03.19; Holland, W. L., et al. (2007). Inhibition of ceramide synthesis ameliorates glucocorticoid-, saturated-fat-, and obesity-induced insulin resistance. Cell Metab 5, 167-179. doi: 10.1016/j.cmet.2007.01.002; Holland, W. L., et al. (2011). Receptor-mediated activation of ceramidase activity initiates the pleiotropic actions of adiponectin. Nat Med 17, 55-63. doi: 10.1038/nm.2277; Itoh, N. (2010). Hormone-like (endocrine) Fgfs: their evolutionary history and roles in development, metabolism, and disease. Cell Tissue Res 342, 1-11. doi: 10.1007/s00441-010-1024-2; Kharitonenkov, A., et al. (2011). FGF21 reloaded: challenges of a rapidly growing field. Trends Endocrinol Metab 22, 81-86. doi: 10.1016/j.tem.2010.11.003; Lancaster, G. I., et al. (2011). Adiponectin sphings into action. Nat 1\ried 17, 37-38. doi: 10.1038/nmO 111-37; Lin, Z., et al. (2013). Adiponectin mediates the metabolic effects of FGF21 on glucose homeostasis and insulin sensitivity in mice. Cell Metab 17, 779-789. doi:10.1016/j.cmet.2013.04.005; Lopez, X., et al. (2013). Plasma ceramides are elevated in female children and adolescents with type 2 diabetes. J Pediatr Endocrinol Metab 26, 995-998. doi: 10.1515/jpem-2012-0407; Mantzoros, C. S., et al. (2005). Circulating adiponectin levels are associated with better glycemic control, more favorable lipid profile, and reduced inflammation in women with type 2 diabetes. J Clin Endocrinol Metab 90, 4542-4548. doi: 10.1210/jc.2005-0372; Mao, C., et al. (2008). Ceramidases: regulators of cellular responses mediated by ceramide, sphingosine, and sphingosine-1-phosphate. Biochim Biophys Acta 1781, 424-434. doi: 10.1016/j.bbalip.2008.06.002; Matikainen, N., et al. (2012). Decrease in circulating fibroblast growth factor 21 after an oral fat load is related to postprandial triglyceride-rich lipoproteins and liver fat. Eur J Endocrinol 166, 487-492. doi: 10.1530/EJE-11-0783; Miller, R. A., et al. (2011). Adiponectin suppresses gluconeogenic gene expression in mouse hepatocytes independent of LKBI-AMPK signaling. J Clin Invest 121, 2518-2528. doi: 10.1172/JCI45942; Neely, B. A., et al. (2013). Ratiometric Measurements of Adiponectin by Mass Spectrometry in Bottlenose Dolphins (*Tursiops truncatus*) with Iron Overload Reveal an Association with Insulin Resistance and Glucagon. Front Endocrinol (Lausanne) 4, 132. doi: 10.3389/fendo.2013.00132; Neumeier, M., et al. (2006). Different effects of adiponectin isoforms in human monocytic cells. J Leukoc Biol 79, 803-808. doi: 10.1189/jlb.0905521; Nygaard, E. B., et al. (2014). Increased fibroblast growth factor 21 expression in high-fat diet-sensitive non-human primates (*Macaca* mulatta). Int J Obes (Lond) 38, 183-191. doi: 10.1038/ijo.2013.79; Ozeki, N., et al. (2009). Serum high-molecular weight adiponectin decreases abruptly after an oral glucose load in subjects with normal glucose tolerance or impaired fasting glucose, but not those with impaired glucose tolerance or diabetes mellitus. Metabolism 58, 1470-1476. doi: 10.1016/j.metabol.2009.04.042; Park, S. E., et al. (2015). Biomarkers of insulin sensitivity and insulin resistance: Past, present and future. Crit Rev Clin Lab Sci 52, 180-190. doi: 10.3109/10408363.2015.1023429; Rakatzi, I., et al. (2004). Adiponectin counteracts cytokine- and fatty acid-induced apoptosis in the pancreatic beta-cell line INS-1. Diabetologia 47, 249-258. doi: 10.1007/s00125-003-1293-3; Reinhard, M., et al. (2015). Response of fibroblast growth factor 21 to meal intake and insulin infusion in patients on maintenance haemodialysis. Clin Endocrinol (Oxf) 83, 187-195. doi: 10.1111/cen.12737; Rutkowski, J. M., et al. (2014). Isolation and quantitation of adiponectin higher order complexes. Methods Enzymol 537, 243-259. doi: 10.1016/B978-O-12-411619-1.00013-6; Rutkowski, J. M., et al. (2013). Adiponectin promotes functional recovery after podocyte ablation. J Am Soc Nephrol 24, 268-282. doi: 10.1681/ASN.2012040414; Samad, F., et al. (2006). Altered adipose and plasma sphingolipid metabolism in obesity: a potential mechanism for cardiovascular and metabolic risk. Diabetes 55, 2579-2587. doi: 10.2337/db06-0330; Schaer, D. J., et al. (2014). Haptoglobin, hemopexin, and related defense pathways-basic science, clinical perspectives, and drug development. Front Physiol 5, 415. doi: 10.3389/fphys.2014.00415; Schoenberg, K. M., et al. (2011). Plasma FGF21 is elevated by the intense lipid mobilization of lactation. Endocrinology 152, 4652-4661. doi:10.1210/en.2011-1425; Schulze, M. B., et al. (2004). Relationship between adiponectin and glycemic control, blood lipids, and inflammatory markers in men with type 2 diabetes. Diabetes Care 27, 1680-1687; Tworoger, S. S., et al. (2007). Relationship of plasma adiponectin with sex hormone and insulin-like growth factor levels. Obesity (Silver Spring) 15, 2217-2224. doi: 10.1038% by.2007.263; Valenti, L., et al. (2007). Iron depletion by phlebotomy improves insulin resistance in patients with nonalcoholic fatty liver disease and hyperferritinemia: evidence from a case-control study. Am J Gastroenterol 102, 1251-1258. doi: 10.1111/j.1572-0241.2007.01192.x; Van Dolah, et al. (2015). Seasonal variation in the skin transcriptome of common bottlenose dolphins (*Tursiops truncatus*) from the northern Gulf of Mexico. PLoS One 10, e0130934. doi: 10.1371/journal.pone.0130934; Varady, J., et al. (2012). Dietary moderately oxidized oil induces expression of fibroblast growth factor 21 in the liver of pigs. Lipids Health Dis 11, 34. doi: 10.1186/1476-5 ll X-ll-34; Wang, Y., et al. (2006). Post-translational modifications of the four conserved lysine residues within the collagenous domain of adiponectin are required for the formation of its high molecular weight oligomeric complex. J Biol Chem 281, 16391-16400. doi: 10.1074/jbc.M513907200; Wang, Y., et al. (2002). Hydroxylation and glycosylation of the four conserved lysine residues in the collagenous domain of adiponectin. Potential role in the modulation of its insulin-sensitizing activity. J Biol Chem 277, 19521-19529. doi: 10.1074/jbc.M200601200; Wells, R. (1984). Reproductive Behavior and Hormonal Correlates in Hawaiian Spinner Dolphins, Stenella *longirostris*. Reproduction on Whales, Dolphins, and Porpoises. Cambridge: Reports of the International Whaling Commission, 465-472; FOROUHI, NITA G. et al., "Differences in the Prospective Association Between Individual Plasma Phospholipid Saturated Fatty Acids and Incident Type 2 Diabetes: The EPIC-InterAct Case-Cohort Study", Lancet Diabetes Endocrinal 2014: Vol. 2, pp 810-818 (2014); KRACHLER, BENNO et al., "Fatty Acid Profile of the Erythrocyte Membrane Preceding Development of Type 2 Diabetes Mellitus", Nutrition, Metabolism & Cardiovascular Diseases, vol. 18, pp. 503-510 (2008);

MARUYAMA, CHIZUKO et al., "Differences in Serum Phospholipid Fatty Acid Compositions and Estimated Desaturase Activities Between Japanese Men With and Without Metabolic Syndrome", Journal of Atherosclerosis and Thrombosis, Vol. 15, No. 6, pp. 306-313 (2008); MAGNUSDOTTIR, O K et al., "Plasma Alkylresorcinols C 1 7:0/C21:0 Ratio, A Biomarker of Relative Whole-Grain Rye Intake, Is Associated to Insulin Sensistivity: A Randomized Study", European Journal of Clinical Nutrition Vol. 68, pp. 453-458 (2014); LAGERSTEDT, SUSAN A et al., "Quantitative Determination of Plasma C8-C25 Total Fatty Acids for the Biochemical Diagnosis of Nutritional and Metabolic Disorders", Molecular Genetics and Metabolism, vol. 73, pp. 38-45 (2001).

The above description presents the best mode contemplated for carrying out the present invention, and of the manner and process of making and using it, in such full, clear, concise, and exact terms as to enable any person skilled in the art to which it pertains to make and use this invention. This invention is, however, susceptible to modifications and alternate constructions from that discussed above that are fully equivalent. Consequently, this invention is not limited to the particular embodiments disclosed. On the contrary, this invention covers all modifications and alternate constructions coming within the spirit and scope of the invention as generally expressed by the following claims, which particularly point out and distinctly claim the subject matter of the invention. While the disclosure has been illustrated and described in detail in the drawings and foregoing description, such illustration and description are to be considered illustrative or exemplary and not restrictive.

All references cited herein are incorporated herein by reference in their entirety. To the extent publications and patents or patent applications incorporated by reference contradict the disclosure contained in the specification, the specification 1s intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article 'a' or 'an' does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases 'at least one' and "one or more" to introduce claim recitations. However, the use of such phrases should not be construed to imply that the introduction of a claim recitation by the indefinite articles 'a' or 'an' limits any particular claim containing such introduced claim recitation to embodiments containing only one such recitation, even when the same claim includes the introductory phrases 'one or more' or 'at least one' and indefinite articles such as 'a' or 'an' (e.g., 'a' and/or 'an' should typically be interpreted to mean 'at least one' or 'one or more'); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of 'two recitations,' without other modifiers, typically means at least two recitations, or two or more recitations). Furthermore, in those instances where a convention analogous to 'at least one of A, B, and C, etc.' is used, in general such a construction is intended in the sense one having skill in the art would understand the convention (e.g., 'a system having at least one of A, B, and C' would include but not be limited to systems that have A alone, B alone, C alone, A and B together, A and C together, B and C together, and/or A, B, and C together, etc.). In those instances where a convention analogous to 'at least one of A, B, or C, etc.' is used, in general such a construction is intended in the sense one having skill in the art would understand the convention (e.g., 'a system having at least one of A, B, or C' would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase 'A or B' will be understood to include the possibilities of 'A' or 'B' or 'A and B.'

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method comprising:
   using pentadecanoic acid in a supplement to human diet at a level sufficient to treat symptoms of metabolic syndrome, wherein said supplement is selected from the group consisting of food additives, food fortifiers, beverage additives, beverage fortifiers, or pharmaceuticals, and is administered to a subject at a daily dose comprising an approximate minimum of 3 mg per lb (or 6 mg per kg) of body weight.

2. A method comprising:
   administering, to a patient, pentadecanoic acid at a daily dose comprising an approximate minimum of 3 mg per lb (or 6 mg per kg) of the patient's body weight, wherein the pentadecanoic acid is administered in a form selected from the group consisting of a supplement, a food, a food additive, a food fortifier, a beverage additive, a beverage fortifier, and a pharmaceutical.

3. A method comprising:
   administering, to a patient, pentadecanoic acid at a daily dose comprising an approximate minimum of 0.3 mg per kg of the patient's body weight, wherein the pentadecanoic acid is administered in a form selected from the group consisting of a supplement, a food, a food additive, a food fortifier, a beverage additive, a beverage fortifier, and a pharmaceutical.

4. The method of claim 2, wherein the pharmaceutical is in a form selected from the group consisting of a tablet, an encapsulated pill, a gelcap pill, a liquid suspension, a spray, and a powder.

5. The method of claim 2, wherein the patient is a mammal.

6. The method of claim 5, wherein the mammal is a human.

* * * * *

(12) EX PARTE REEXAMINATION CERTIFICATE (12730th)
United States Patent
Venn-Watson

(10) Number: US 11,116,740 C1
(45) Certificate Issued: *Oct. 11, 2024

(54) METHODS FOR USE IN SUPPORT OF PLANNED SUPPLEMENT AND FOOD INGREDIENT PRODUCTS FOR DIAGNOSIS AND TREATMENT OF METABOLIC SYNDROME

(71) Applicant: The United States of America as represented by the Secretary of the Navy, San Diego, CA (US)

(72) Inventor: Stephanie Venn-Watson, San Diego, CA (US)

(73) Assignee: UNITED STATES OF AMERICA AS REPRESENTED BY THE SECRETARY OF THE NAVY, Arlington, VA (US)

Reexamination Request:
No. 90/019,345, Dec. 20, 2023

Reexamination Certificate for:
Patent No.: 11,116,740
Issued: Sep. 14, 2021
Appl. No.: 16/534,382
Filed: Aug. 7, 2019

(*) Notice: This patent is subject to a terminal disclaimer.

Related U.S. Application Data

(63) Continuation of application No. 16/018,922, filed on Jun. 26, 2018, now Pat. No. 10,449,171, which is a continuation of application No. 15/582,433, filed on Apr. 28, 2017, now Pat. No. 10,022,347, which is a continuation of application No. 15/030,031, filed as application No. PCT/US2015/067172 on Dec. 21, 2015, now Pat. No. 9,662,306, which is a continuation-in-part of application No. 14/591,660, filed on Jan. 7, 2015, now Pat. No. 9,561,206.

(51) Int. Cl.
*A61K 31/20* (2006.01)
*A61K 31/201* (2006.01)
*A61K 31/202* (2006.01)
*G01N 33/92* (2006.01)

(52) U.S. Cl.
CPC ............ *A61K 31/20* (2013.01); *A61K 31/201* (2013.01); *A61K 31/202* (2013.01); *G01N 33/92* (2013.01); *G01N 2405/00* (2013.01); *G01N 2800/04* (2013.01); *G01N 2800/042* (2013.01); *G01N 2800/22* (2013.01); *G01N 2800/50* (2013.01)

(58) Field of Classification Search
None
See application file for complete search history.

(56) References Cited

To view the complete listing of prior art documents cited during the proceeding for Reexamination Control Number 90/019,345, please refer to the USPTO's Patent Electronic System.

*Primary Examiner* — Alan D Diamond

(57) ABSTRACT

Compositions including an odd chain fatty acid, and salts and derivatives thereof, and methods for metabolic syndrome treatment and prophylaxis are provided, including compositions and methods for treating diabetes, obesity, hyperferritinemia, elevated insulin, glucose intolerance, dyslipidemia and related conditions. Methods for the diagnosis and monitoring of metabolic syndrome are also provided.

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 4 and 5 are cancelled.

Claims 1-3 and 6 are determined to be patentable as amended.

New claims 7-70 are added and determined to be patentable.

1. A method comprising:
   using pentadecanoic acid in a supplement to human diet at a level sufficient to treat symptoms of metabolic syndrome, wherein said supplement is [selected from the group consisting of food additives, food fortifiers, beverage additives, beverage fortifiers, or pharmaceuticals,] *a food additive, a food fortifier, a beverage additive, or a beverage fortifier,* and is administered to a [subject] *human in need thereof* at a daily dose [comprising] *of the pentadecanoic acid at* an approximate minimum of [3 mg per lb (or 6 mg per kg)] *6 mg per kg up to 20 mg per kg* of *the human's* body weight *for treating symptoms of metabolic syndrome, wherein the symptoms of metabolic syndrome comprise one or more of: oxidative stress, hyperglycemia, dyslipidemia, insulin resistance, non-alcoholic fatty liver disease, obesity, type 2 diabetes, and cardiovascular disease.*

2. A method comprising:
   administering, to a patient, pentadecanoic acid at a daily dose comprising an approximate minimum of [3 mg per lb (or 6 mg per kg)] *6 mg per kg up to 20 mg per kg* of the patient's body weight [,] *for (i) alleviating one or more of: oxidative stress, hyperglycemia, dyslipidemia, insulin resistance, non-alcoholic fatty liver disease, obesity, type 2 diabetes, and cardiovascular disease, (ii) achieving energy homeostasis, (iii) achieving fuel homeostasis, or any combination of (i)-(iii),*
   *wherein the patient is a mammal, and*
   wherein the pentadecanoic acid is administered in a form [selected from the group consisting] of a supplement[, a food, a food additive, a food fortifier, a beverage additive, a beverage fortifier, and a pharmaceutical].

3. A method comprising:
   administering, to a patient, pentadecanoic acid at a daily dose comprising an approximate minimum of 0.3 mg per kg *up to 20 mg per kg* of the patient's body weight [,] *for (i) alleviating one or more of: oxidative stress, hyperglycemia, dyslipidemia, insulin resistance, non-alcoholic fatty liver disease, obesity, type 2 diabetes, and cardiovascular disease, (ii) achieving energy homeostasis, (iii) achieving fuel homeostasis, or any combination of (i)-(iii),*
   *wherein the patient is a mammal, and*
   wherein the pentadecanoic acid is administered in a form [selected from the group consisting] of a supplement[, a food, a food additive, a food fortifier, a beverage additive, a beverage fortifier, and a pharmaceutical].

6. The method of claim [5] *2*, wherein the mammal is a human.

7. *The method of claim 1, wherein the supplement is administered to the human for at least about one month.*

8. *The method of claim 1, wherein the supplement is orally administered to the human.*

9. *The method of claim 1, wherein the supplement is orally administered to the human for at least about one month.*

10. *The method of claim 1, wherein the symptoms of metabolic syndrome comprise one or more of: oxidative stress, hyperglycemia, dyslipidemia, insulin resistance, non-alcoholic fatty liver disease, type 2 diabetes, and cardiovascular disease.*

11. *The method of claim 2, wherein the mammal is a dolphin, a sheep, a goat, a cow, a dog, a cat, or a horse.*

12. *The method of claim 2, wherein the pentadecanoic acid is orally administered at the daily dose.*

13. *The method of claim 2, wherein the pentadecanoic acid is administered for at least about one month.*

14. *The method of claim 2, wherein the pentadecanoic acid is orally administered at the daily dose for at least about one month.*

15. *The method of claim 14, wherein the mammal is a human, a sheep, a goat, a cow, a dog, a cat, a horse, or a dolphin.*

16. *The method of claim 15, wherein the mammal is a human.*

17. *The method of claim 2, wherein the supplement is a food additive, a food fortifier, a beverage additive, or a beverage fortifier.*

18. *The method of claim 2, wherein the pentadecanoic acid is administered at the daily dose for alleviating one or more of: oxidative stress, hyperglycemia, dyslipidemia, insulin resistance, non-alcoholic fatty liver disease, obesity, type 2 diabetes, and cardiovascular disease.*

19. *The method of claim 2, wherein the pentadecanoic acid is administered at the daily dose for achieving energy homeostasis.*

20. *The method of claim 2, wherein the pentadecanoic acid is administered at the daily dose for achieving fuel homeostasis.*

21. *The method of claim 2, wherein the pentadecanoic acid is administered at the daily dose for at least about one month for alleviating one or more of: oxidative stress, hyperglycemia, dyslipidemia, insulin resistance, non-alcoholic fatty liver disease, obesity, type 2 diabetes, and cardiovascular disease.*

22. *The method of claim 2, wherein the pentadecanoic acid is administered at the daily dose for at least about one month for achieving energy homeostasis.*

23. *The method of claim 2, wherein the pentadecanoic acid is administered at the daily dose for at least about one month for achieving fuel homeostasis.*

24. *The method of claim 21, wherein the pentadecanoic acid is administered at the daily dose for at least about one month for alleviating oxidative stress, hyperglycemia, dyslipidemia, insulin resistance, non-alcoholic fatty liver disease, type 2 diabetes, and cardiovascular disease.*

25. *The method of claim 3, wherein the mammal is a human.*

26. *The method of claim 3, wherein the mammal is a dolphin, a sheep, a goat, a cow, a dog, a cat, or a horse.*

27. *The method of claim 3, wherein the pentadecanoic acid is orally administered to the mammal at the daily dose.*

28. *The method of claim 3, wherein the pentadecanoic acid is administered to the mammal for at least about one month.*

29. The method of claim 3, wherein the pentadecanoic acid is orally administered to the mammal at the daily dose for at least about one month.

30. The method of claim 29, wherein the mammal is a human, a dolphin, a sheep, a goat, a cow, a dog, a cat, or a horse.

31. The method of claim 30, wherein the mammal is a human.

32. The method of claim 3, wherein the supplement is a food additive, a food fortifier, a beverage additive, or a beverage fortifier.

33. The method of claim 3, wherein the pentadecanoic acid is administered at the daily dose for alleviating one or more of: oxidative stress, hyperglycemia, dyslipidemia, insulin resistance, non-alcoholic fatty liver disease, obesity, type 2 diabetes, and cardiovascular disease.

34. The method of claim 3, wherein the pentadecanoic acid is administered at the daily dose for achieving energy homeostasis.

35. The method of claim 3, wherein the pentadecanoic acid is administered at the daily dose for achieving fuel homeostasis.

36. The method of claim 3, wherein the pentadecanoic acid is administered at the daily dose for at least about one month for alleviating one or more of: oxidative stress, hyperglycemia, dyslipidemia, insulin resistance, non-alcoholic fatty liver disease, obesity, type 2 diabetes, and cardiovascular disease.

37. The method of claim 3, wherein the pentadecanoic acid is administered at the daily dose for at least about one month for achieving energy homeostasis.

38. The method of claim 3, wherein the pentadecanoic acid is administered at the daily dose for at least about one month for achieving fuel homeostasis.

39. The method of claim 3, wherein the daily dose is an approximate minimum of 0.3 mg per kg up to 9 mg per kg of the mammal's body weight.

40. The method of claim 39, wherein the mammal is a human.

41. The method of claim 36, wherein the pentadecanoic acid is administered at the daily dose for at least about one month for alleviating one or more of: oxidative stress, hyperglycemia, dyslipidemia, insulin resistance, non-alcoholic fatty liver disease, type 2 diabetes, and cardiovascular disease.

42. A method, comprising:
administering to a mammal in need thereof pentadecanoic acid at a daily dose of an approximate minimum of 0.3 mg per kg up to 20 mg per kg of the mammal's body weight for at least about one month, wherein the pentadecanoic acid is administered as a supplement, and wherein the pentadecanoic acid is administered for alleviating one or more of: oxidative stress, hyperglycemia, dyslipidemia, insulin resistance, non-alcoholic fatty liver disease, obesity, type 2 diabetes, and cardiovascular disease.

43. The method of claim 42, wherein the mammal is a human.

44. The method of claim 42, wherein the mammal is a dolphin, a sheep, a goat, a cow, a dog, a cat, or a horse.

45. The method of claim 42, wherein the pentadecanoic acid is orally administered at the daily dose.

46. The method of claim 42, wherein the supplement is a food additive, a food fortifier, a beverage additive, or a beverage fortifier.

47. A method, comprising:
administering to a mammal in need thereof pentadecanoic acid at a daily dose of an approximate minimum of 0.3 mg per kg up to 20 mg per kg of the mammal's body weight for at least about one month, wherein the pentadecanoic acid is administered as a supplement, and wherein the pentadecanoic acid is administered for achieving energy homeostasis.

48. A method, comprising:
administering to a mammal in need thereof pentadecanoic acid at a daily dose of an approximate minimum of 0.3 mg per kg up to 20 mg per kg of the mammal's body weight for at least about one month, wherein the pentadecanoic acid is administered as a supplement, and wherein the pentadecanoic acid is administered for achieving fuel homeostasis.

49. A method, comprising:
administering to a mammal in need thereof pentadecanoic acid at a daily dose of an approximate minimum of 0.3 mg per kg up to 20 mg per kg of the mammal's body weight for at least about one month, wherein the pentadecanoic acid is administered as a supplement, and wherein the pentadecanoic acid is administered for alleviating symptoms of metabolic syndrome.

50. The method of claim 42, wherein the daily dose is an approximate minimum of 0.3 mg per kg up to 9 mg per kg of the mammal's body weight.

51. The method of claim 50, wherein the mammal is a human.

52. A method, comprising:
administering, to a mammal, pentadecanoic acid at a daily dose of an approximate minimum of 0.3 mg per kg up to 20 mg per kg of the mammal's body weight orally administered to the mammal in a capsule, a cachet, a tablet, an oil, a powder, or a liquid suspension, for preventing or alleviating one or more symptoms of metabolic syndrome affecting the mammal.

53. The method of claim 52, wherein the daily dose is 20 mg per kg of the mammal's body weight.

54. The method of claim 52, wherein the mammal is a human or a dolphin.

55. The method of claim 52, wherein the pentadecanoic acid is orally administered to the mammal in the capsule, the cachet, the tablet, the oil, the powder, or the liquid suspension substantially free from other fatty acids.

56. The method of claim 52, wherein the pentadecanoic acid is orally administered to the mammal in the capsule, the cachet, the tablet, the oil, the powder, or the liquid suspension substantially free from even chain fatty acids.

57. The method of claim 52, wherein the pentadecanoic acid is orally administered to the mammal in the capsule, the cachet, the tablet, the oil, the powder, or the liquid suspension substantially free from triglycerides.

58. The method of claim 52, wherein preventing or alleviating the one or more symptoms of metabolic syndrome affecting the mammal comprises increasing a red blood cell membrane concentration of one or more odd chain fatty acids of the mammal.

59. The method of claim 52, wherein preventing or alleviating the one or more symptoms of metabolic syndrome affecting the mammal comprises preventing or alleviating a proinflammatory state affecting the mammal.

60. The method of claim 47, wherein the mammal is a human.

61. The method of claim 47, wherein the mammal is a dolphin, a sheep, a goat, a cow, a dog, a cat, or a horse.

62. The method of claim 47, wherein the pentadecanoic acid is orally administered at the daily dose.

63. The method of claim 47, wherein the supplement is a food additive, a food fortifier, a beverage additive, or a beverage fortifier.

64. The method of claim 48, wherein the mammal is a human.

65. The method of claim 48, wherein the mammal is a dolphin, a sheep, a goat, a cow, a dog, a cat, or a horse.

66. The method of claim 48, wherein the pentadecanoic acid is orally administered at the daily dose.

67. The method of claim 48, wherein the supplement is a food additive, a food fortifier, a beverage additive, or a beverage fortifier.

68. The method of claim 49, wherein the mammal is a human.

69. The method of claim 49, wherein the mammal is a dolphin, a sheep, a goat, a cow, a dog, a cat, or a horse.

70. The method of claim 49, wherein the pentadecanoic acid is orally administered at the daily dose.

71. The method of claim 49, wherein the supplement is a food additive, a food fortifier, a beverage additive, or a beverage fortifier.

72. The method of claim 52, wherein the mammal is a sheep, a goat, a cow, a dog, a cat, or a horse.

\* \* \* \* \*